United States Patent [19]
Torrence et al.

[11] Patent Number: 5,998,602
[45] Date of Patent: Dec. 7, 1999

[54] RNASE L ACTIVATORS AND ANTISENSE OLIGONUCLEOTIDES EFFECTIVE TO TREAT RSV INFECTIONS

[75] Inventors: Paul F. Torrence, Silver Spring, Md.; Robert Hugh Silverman, Beachwood; Nick Mario Cirino, Cleveland Heights, both of Ohio; Guiying Li, Durham, N.C.; Wei Xiao, North Potomac, Md.

[73] Assignee: The Cleveland Clinic Fouindation and Government, Cleveland, Ohio

[21] Appl. No.: 08/801,898

[22] Filed: Feb. 14, 1997

Related U.S. Application Data

[60] Provisional application No. 60/011,725, Feb. 15, 1996.

[51] Int. Cl.$^6$ .................................................. C07H 21/00
[52] U.S. Cl. ............................................................ 536/24.5
[58] Field of Search .............................. 435/6, 199, 91.1, 435/325, 375; 514/44; 536/24.3, 24.5; 935/34

[56] References Cited

U.S. PATENT DOCUMENTS

| | | | |
|---|---|---|---|
| 5,532,130 | 7/1996 | Alul | 435/6 |
| 5,583,032 | 12/1996 | Torrence et al. | 435/91.1 |
| 5,585,479 | 12/1996 | Hoke et al. | 536/24.5 |

FOREIGN PATENT DOCUMENTS

| | | |
|---|---|---|
| 94/09129 | 4/1994 | WIPO . |
| 95/22553 | 8/1995 | WIPO . |

OTHER PUBLICATIONS

Branch. A good antisense molecule is hard to find. Trends Biochem. Sci. 23: 45–50, Feb. 1998.
Gewirtz et al. Facilitating oligonucleotide delivery: Helping antisense deliver on its promise. Proc. Nat. Acad. Sci. USA 93: 3161–3163, Apr. 1996.
Shaw et al. Modified deoxyoligonucleotides stable to exonuclease degredation in serum. Nuc. Acids Res. 19: 747–750, Mar. 1991.
Antisense '97: A roundtable on the state of the industry. Nature Biotechnology 15: 519–524, Jun. 1997.
Gura. Antisense has growing pains. Science 270: 575–577, Oct. 1995.
Stull et al. Antigene, ribozyme and aptamer nucleic acid drugs: Progress and prospects. Pharm. Res. 12: 465–483, Apr. 1995.
Whitton. Antisense treatment of viral infection. Adv. Virus Res. 44: 267–303, 1994.
Cirino et al., 1997, "Targeting RNA Decay with 2',5' Oligoadenylate–Antisense in Respiratory Syncytial Virus–Infected Cells", Proc. Natl. Acad. Sci. USA 94:1937–1942.
Beigelman et al., 1995, "Synthesis and Biological Activities of a Phosphorodithioate Analog of 2',5'–Oligoadenylate", Nucl. Acids. Res. 23:3989–3994.
Maitra et al., 1995, "Catalytic Cleavage of an RNA Target by 2–5A–Antisense and 2–5A Dependent RNase", J. Biol.Chem. 270:15071–15075.

Englund, 1994, "High–Dose, Short Duration Ribavirin Aerosol Therapy Compared with Standard Therapy in Children with Suspected Respiratory Syncytial Virus Infection", J. Pediatrics 125:635–641.
Maran et aL., 1994, "Blockage of NF–kB Signaling by Selective Ablation of an mRNA Target by 2–5A–Antisense Chimeras", Science 265:789–792.
Merolla et al., 1995, "Respiratory Syncytial Virus Replication in Human Lung Epithelial Cells: Inhibition by Tumor NecrosisFfactor–a and Interferon–a8247", Am. J. Rsp. and Crit. Care Med.
Silverman, 1994, "Fascination with 2–5A–Dependent RNase: A Unique Enzyme that Functions in Interferon Action", J. Interferon Res. 14:101–104.
Swiderski et al., 1994, "Polystyrene Reverse–Phase Ion–Pair Chromatography of Chimeric Ribozymes", Analytical Biochemistry 216: 83–88.
Xiao et al., 1994, "Synthesis of 5'–Thiophosphate Analogue of 2–5A, a Phosphatase Resistant Activator of the 2–5A Dependent Ribonuclease", Bioorganic & Med. Chem. Letts 4:2609–2614.
Balotta et al., 1993, "Antisense Phosphorothioate Oligodeoxynucleotides Targeted to the vpr Gene Inhibit Human Immunodeficiency Virus Type 1 Replication in Primary Human Macrophages", J. Virology 67:4409–4414.
Cirino et al., 1993, "Restricted Replication of Respiratory Syncytial Virus in Human Alveolar Macrophages", J. Gen. Virol. 74:1527–1537.
Hassel et al., 1993, "A Dominant Negative Mutant of 2–5A–Dependent RNase Suppresses Antiproliferative and Antiviral Effects of Interferon", The EMBO Journal 12:3297–3304.
Lesiak et al., 1993, "2',5'–Oligoadenylate–Antisense Chimeras–Synthesis and Properties", Bioconjugate Chem 4:467–472.

(List continued on next page.)

*Primary Examiner*—David Guzo
*Assistant Examiner*—Thomas G. Larson
*Attorney, Agent, or Firm*—Pennie & Edmonds LLP

[57] ABSTRACT

The invention concerns a compounds and methods for treating infection with Respiratory Syncytial Virus. The compounds comprise an antisense portion, which is complementary to a normally single stranded portion of the RSV antigenomic strand (the mRNA strand), a linker and a oligonucleotide activator of RNase L, a ubiquitous non-specific RNase. The method comprised forming a complex of an activated RNase L and the antisense molecule. The application teaches methods of determining which portions of the RSV antigenomic strand are normally single-stranded. The application teaches that an antisense oligonucleotide having the sequence of residues 8281–8299 of the RSV genome is particularly useful to practice the invention and provides in vitro results superior to those obtainable with the conventional drug of choice, ribavirin.

7 Claims, 30 Drawing Sheets

OTHER PUBLICATIONS

Midulla et al., 1993, "Concise Communication: Respiratory Syncytial Virus Lung Infection in Infants: Immunoregulatory Role of Infected Alveolar Macrophages", J. Inf. Dis. 168:1515–1519.

Torrence et al., 1993, "Targeting RNA for Degradation with a 2',5'–Oligoadenylate–Antisense Chimera", Proc. Natl. Acad. Sci. USA 90:1300–1304.

Agrawal, 1992, "Antisense Oligonucleotides as Antiviral Agents", Trends Biotechnol. 10:152–158.

Panuska et al., 1992, "Respiratory Syncytial Virus Infection of Alveolar Macrophages in Adult Transplant Patients", Am. Rev. Resp. Dis. 145:934–939.

Gribaudo et al., 1991, "Interferon Action: Binding of Viral RNA to the 40–Kilodalton 2'–5' Oligoadenylate Synthetase in Interferon–Treated HeLa Cells Infected with Encelphalomyocarditis Virus", J. Virol. 65:1748–1757.

McIntosh and Chanock, 1990, "Respiratory Syncytial Virus", In Virology, 2nd edition. Edited by BN Fields, DM Knipe et al., Raven Press, Ltd, New York, pp. 1045–1072.

Letsinger et al., 1989, "Cholesteryl–Conjugated Oligonucleotides: Synthesis, Properties, and Activity as Inhibitors of Replication of Human Immunodeficiency Virus in Cell Culture", Proc. Natl. Acad. Sci. USA 86:6553–6556.

Rysiecki et al., 1989, "Constitutive Expression of a 2',5'–Oligoadenylate Synthetase cDNA Results in Increased Antiviral Activity and Growth Suppression", J. Interferon. Res. 9:649–657.

Zuker, 1989, "Computer Prediction of RNA Structure", Methods in Enzymology 180:262–288.

Zuker, 1989, "On Finding All Suboptimal Foldings of an RNA Molecule", Science 244:48.

Goodchild, 1988, "Inhibition of Human Immunodeficiency Virus Replication by Antisense Oligodeoxynucleotides", Proc. Natl. Acad. Sci. USA. 85:5507–5511.

Gruenert et al., 1988, "Characterization of Human Tracheal Epithelial Cells Transformed by an Origin Defective Simian Virus 40", Proc. Natl. Acad. Sci. USA. 85:5951–5955.

Chebath et al., 1987, "Constitutive Expression of (2'–5') Oligo A Synthetase Confers Resistance to Picornavirus Infection", Nature 330:587–588.

Freier et al., 1986, "Improved Free–Energy Parameters for Predictions of RNA Duplex Stability", Proc. Natl. Acad. Sci. USA 83:9373–9377.

Zamecnik et al., 1986, "Inhibition of Replication and Expression of Human T–Cell Lymphotropic Virus Type III in Cultured Cells by Exogenous Synthetic Oligonucleotides Complementary to Viral RNA", Proc. Natl. Acad. Sci. USA. 83:4143–4146.

Hall et al., 1983, "Aerosolized Ribavirin Treatment of Infants with Respiratory Syncytial Viral Infection", N. Eng. J. Med. 308:1443–1447.

Taber et al., 1983, "Ribavirin Aerosol Treatment of Bronchiolitis Associated with Respiratory Syncytial Virus Infection in Infants", Pediatrics 72:613–618.

Floyd–Smith et al., 1981, "Interferon Action: RNA Cleavage Pattern of a (2'–5') Oligoadenylate–Dependent Endonuclease", Science 212:1020–1032.

Wreschner et al., 1981, "Ribosomal RNA Cleavage, Nuclease Activation and 2–5A(ppp(A2'p)nA) in Interferon–Treated Cells", Nucleic Acids Res. 9:1571–1581.

Wreschner et al., 1981, "Interferon Action–Sequence Specificity of the ppp(A2'p)nA–Dependent Ribonuclease", Nature 289:414–417.

Salser, 1977, "Globin mRna Sequences: Analysis of Base Pairing and Evolutionary Implications", Cold Spring Harbor Symposium on Quantitative Biology 42:985–1002.

Panuska et al., 1995, "Respiratory Syncytial Virus Induces Interleukin–10 by Human Alveolar Macrophages", J. Clin. Invest. 96:2445–2453.

```
   1  acgagaaaaa aagtgtcaaa aactaatatc tcgtaattta gttaatacac
  51  atataaacca attagattag ggtttaaatt tattcctcca agattaaaat
 101  gataacttta ggattagttc actaaaagtt atttaaaaaa ttatatgatt
 151  tttaatttt  aataactata attgaataca gtgttagtgt atagctatgg
 201  gaatttttat tataagatcc ttattcatta ttcattatga aagttgtata
 251  acagactacc tgtgatttta atcagttttt taagttcatt ggttgtcaag
 301  ctgtttaaca attcacttag gtaaggatat gtagattcta ccatatataa
 351  atggttatag tttagttctg ttgatctgaa atttaaaaca tgattgaacc
 401  attttaagat gttcatatgc ttatgattta taagtttatt gctgaaaact
 451  tcattacgtc cagctataga atatgatagt atatctccac taacaacact
 501  ctttagtttt gacaatgcag tattaattcc tttttttgtt atagggtaac
 551  aaagaaaggg tatcaaactt ttaatatttg catcaataga ctctttatca
 601  gctttcttag gcatgatgaa attttt ggtt cttgatagta tcaatttagc
 651  attttgtact acattaaata ctgggaatat attcgcagga cctattgtaa
 701  ggactaagta aacctccgat cccttt aact tactgcctaa gcatacataa
 751  gttttt aata tagttatatt gtctaatttg aaatcaatat catcttgagc
 801  atgatatttt actattaaca tacatttatt aactgaggaa cagtacttgc
 851  actttcttac atgcttgctc cattctatta gttggttgca tctgtagcag
 901  gttacagaca attcggcatc acagacaaaa agactgatag gttcagcaaa
 951  ctttatatgt aaataagacc aatgaatgtt gttggttgca tctgtagcag
1001  gaatggtcaa attttcacca taatcaatgt tgatatgtcc attgtacagc
1051  cttaaaaact caataggtaa actatgatca ttgcaatctt tcagacttct
1101  gtaaatatat cttatgtcag gatgaagttc cactactgta cgcaataata
1151  aattccctgc tccttcacct atgaatgcta tacaattggg atctttaatt
1201  ttaagatctt ttaaaatata ctctatacta attttacaac ctgtagaact
1251  aaatacaaaa ttgaatctat taatatgatg ccaaggaagc atgcagtaaa
1301  gtgatgtgct attgtgcact aaagatattt ggtgggaagt agtagtgtaa
1351  agttggttgg atttggctgt attgcctgaa tgatctataa ttctatcaag
1401  cacaaccata gggaataaat tatacaaatc ttgtttgctg taattggttc
1451  taatcattgc agacgattta ataagcttct tattagataa caatggtaac
1501  attattgagt caacattttt acctatacaa tagtcattca gtgtcttttt
1551  gtcattactt taatcggat  tggctagtat attctctagg gtttctggtg
1601  taggatgata taatttgttg taattatttt ctaattcaga attagcaatc
1651  cttatatgtt tagttaatag atgagtatta tctgagaagt tataattaat
1701  gcagaagaga ttagaagtat aaaattcatc attgaatttg tgtttatttt
1751  taatgtgtat tctatctata tttatcaatc ccattctaac aagatctata
1801  taagttaata ttgctttcat atgtgttgga tgataatcta tgttaacaac
1851  ccaagggcaa actgtgaatt ctgctacatt aagacgttta agaaaccata
1901  atttgaagct atgacatcct tttactctat gtaaacttgc atcttggcta
1951  agaatgtatt tgataacttt ttgttctaaa aataccttag acatagactt
2001  ccaataacta ctgtctatta attccaatac acatagaaga tctgaagtgt
```

FIG. 1A

```
2051  tcatatcaca ctccagcttt gctttgccat aacctttatg aaaacacaag
2101  agataggtct tataagcatt gaagaaaact ttcaaattaa taaacatatg
2151  atcagttata tatccctctc cccaatcttt ttcaaaaata cctttagaat
2201  ctttcataag ttgtataatc agaatccaat gtccagctaa attagtactt
2251  aaaatgtaag tattatgaaa atagtcagat attttatgtg ccaatattaa
2301  attagaatta acatgagatc cagatttgag tgttttatta cttaagaata
2351  attccacata ttgagtcaaa cttattttgt ctggtaaaaa catatgctgt
2401  ttttgtatca cttgttttaa cttgtgaata tcaacatcac ctgtgaatat
2451  gggaggtttc atcaaatgta tctcattaag cttaggtatg agaataattc
2501  tgttaggaca tacattagta aattgttcta ctactgacat taaactaagg
2551  ccaaagctta tacagttttg gaatactatg tcaatatctt catcaccata
2601  cttttctgtt aatatgcgat taatagggct agtgtcaaag tgataatttg
2651  ttgttctata agctggtatt gatgcaggga attcacatgg tctactactg
2701  actgtaaggc gatgcaaata attgacactt aaatattgtg gaaataattt
2751  cttggccttt tcatatgtta acccaagggt tcctatgctg agttcttcca
2801  tgaattcatc cttgttatct atagatgcat acacccaatc caatttgct
2851  aatagatcta tttgatctct ctgttttttg gttaagactt gtctattata
2901  aactaacatt atttttttct cttgtgtaga tgaaccaacc catggtttag
2951  tgggtcctct ctcaccacgt gttaaactgt taacattata tttctctata
3001  attatgccac tagatatagt gcttgtagta tatttgatgt ccattgtata
3051  catgatactg ggtgatgtaa caccaactat attggataaa gaccaagatc
3101  tttccctaac atatttgctt aattcagtaa tacttaggtt ttccatactc
3151  aatatctctc ttttatctct gttacaatcc aatggaagta tccttataag
3201  caaagttatg ttttttcctca tcatctcagt ggctctatca atatctgtta
3251  agtctatggc agaagttttt tccagtatgt tagttataga ttttgtacct
3301  gatataagat ttactatttt ctctgcttta taaagggta aactttcata
3351  aacaactctt agcccatgag gatatgtagg ttctatattt tgcataatat
3401  catttagatc tatctctgta gtagtataat gttgtgcact tttggagaat
3451  attttgtttg gagctgtact caaaacctct gtaactgcca gtctattgat
3501  ttcgctagta attttagctt gtctctcaga ccctaaagct tgaggatctc
3551  tcatcaatgt tacgaattca gcattagggt ttttgtcaaa cgtgattatg
3601  catgttaaga acttattcaa tctatcatct gacagatctt gaagtttatc
3651  ttttaagtca tggtttgtat aataactaag tatgaacaca gagtgaacta
3701  tagcctctgt gaggaagtca ggagttcttc tatagaaact tcgatataac
3751  aagttgggat caccaccacc aaataacatg ggtaaattca tatacaatgt
3801  taatgctgta tcaatattat caagattaaa aaaggttttt aagtgtttca
3851  gaacctttaa tatgtccaaa tatagtttat tgttacataa tgcatgattt
3901  tttaattgta gagcaatctg attatataac catacatttc taaatattaa
3951  actgcataat agactttcac ctctatattc taattcttgt gtcaaactac
4001  ctatagattc tagactcact ttgaaatcat caagtatagt gtttatccac
4051  ggtcccactc ttaggacttt ctttatacta gctgggtaat atacaccgtt
4101  atgttgaatt gttttactca taaattgcat atctcgtgat atataagtct
```

FIG. 1B

```
4151  cagttccttt taatttgtgg cctatgcctg catactcttt atacagtaat
4201  ttaaggctat ttaatgctag caaataatct gcttgagcat gagtttgacc
4251  ttccatgagt ctgattggtt tgcttatatc tattgattga ttgtcaccat
4301  taattaaagc agtaattgag aatttccctt tgagagatat tagatccaat
4351  agtgatatag cttctatggt ccacagtttt tgacaccacc cttcgatgcc
4401  acccatgtga tatctatata atccactttg ttcatctaca ttgttaagat
4451  ctacaatatg atctcctata taggggggtg catgcctata tgtgcatatt
4501  attgtgacat gaggaatagt taaatgtaac caggaaaata gagattgtac
4551  accatgcagt tcatccagca catcactaca aatacatgac gtttcatatc
4601  gaaatgcttg attgaatttg ctgagatctg tgatgataga gcacttacta
4651  atgtaattgt tgtaattatc attgtagcga tttgatttgt tacttattcc
4701  tgctttcaat tctaatattt tttgtagttc tagatcacca tatcttgtaa
4751  gactttcagg aaagaattgt aaaatgtttt cagctatcat tttctctgcc
4801  aatatttgaa cctgtctgaa cattcccggt tgcattgcaa acattctacc
4851  tacactgagt tctctttctt tgcctgtcaa tgataccaca tgattagggt
4901  tgttgagata actttgatta actacacagt tgtataaatc acattcattg
4951  aatttgttat ctcttaaata atactctaat actcttcttg atttatcact
5001  ctcggaaaat tttaattttt catgttctat atagttttgt atgtgtgatg
5051  gcatgtaatt tctagggaaa ctagtccata tcaaattttt aggaggtgat
5101  atagctttat catttataat catttcaaga tccacttttt taggcaaccg
5151  aaactcacga tagaaacgta gtcctgataa cacaatcaaa tctctttctg
5201  taagttccaa caaagaagga taagtgttta gtttatagta agttaaccat
5251  cttaagggta aaacaatagc atttcttaaa gtaggccatc tgttgtaatt
5301  atttacaaac ccttttataa ttctatatat aaaggcacct cttaacatac
5351  tcagactgct taacaagtaa aatttggtct cattgcaatt aattttaaca
5401  gcatccatgg cttgtctttc atctaccatt gggtgtccaa atattctgaa
5451  caaaaaatat agttcactca gattgttaag gttattgtca cctgcaagct
5501  taattaattt aaggaactta cttaatagaa ttatccatct gccatttatt
5551  atattatcgg acactgtctt atctaataat gtatgacata ctcttgatag
5601  cagattttc tgagctttat tagcagcatc tgtgatgttg ttgagcatac
5651  tattataaaa tcgtttctg aattgatctt cttctgttat atttaaaatt
5701  agagacataa taaatccctc tacctctttt attatgtaga acccctcatt
5751  gtgaaatagc tttagtatac aatctccata aaggaatagt tgtgtcaaga
5801  taacattatt gaatccgcat cttaagccta agcttttatt taatgtgttc
5851  aagcagttac taatccatgt aattaaacaa acatttaatc tactaaggct
5901  aatatctttc catgtcaaga attgattata ggttgtcaca gtaattcttt
5951  tgagttcctt atgataaact atacaaccat attggttcaa aataaattga
6001  aatccactaa gagtttgatt atctatcaat gtaaacccat ggtttttac
6051  ctcatttgat cgatactgtg ttaatatgtt gtttaatttt gtgtataagt
6101  taaaccaatg tattaaccat gatggaggat gttgcattga acacatcaat
6151  ttcttcaaga gtgttgtttt gattgtgtct ttttgttttg tagagtgatt
6201  tttgtctgct ttaagatgag attgattatc tttaacagct gaaagtatat
```

FIG. 1C

```
6251  tttgtctgct tatggtcgta ataactgagt tgtcttcatc ttgtccattg
6301  ttggatttaa tcttgtcctt ttctttaagt tgtcttcatc ttgtccattg
6351  atagactttg acatcactta tttctatagc tcttcttatt atcttttaa
6401  gtaaattagt ggtagcaatc tgttctgacg aggtcatact cttgtatgtc
6451  ataagtaatg actgaaaata agtaggttct tctaatttta tttcaccttt
6501  atgatactta gatattaagg actgtgttat atttagtttc tttagattca
6551  tgtgttctat taatggattt tgtctactaa ttaagttggt ataatcattt
6601  ttgagataag gaccattgaa tatgtaactt cctaaagcat tacactctga
6651  gaaagagata acacctttta aataactatc ggttagataa acattagcag
6701  aatttccatt aataatggga tccattttgt cccacaactt gaattgtttg
6751  aattaataat gtaacgatgt ggtgagtgtt agaattgagt gttatgacac
6801  taatatatat attgtatata tatcctcaat aatacctaga tgttgtagaa
6851  aaatttgaat tgtgtcaatc aattcttgag aggtccaatg gatttcattg
6901  aatgtttgat tcggtgagta catatggtta tttgggttgt tttgattgaa
6951  atatagtgtg ttcttttgat tatacatagt aactctacat ctacttgtta
7001  ttagtatgga agttatacta caaggatatt tgtcaggtag tatcattatt
7051  tttggcatgg tcatttgtat cactaacagt tgattctttt gggttgttga
7101  tggttatgct cttatggata tccaatgtgt ttttgatggt tttcttcaat
7151  acgtctgctg gcaatctttt taacagatgg atagtttgtt tattgttttt
7201  cctgttgctt tcaatatatg atatgacagt attgtacact cttatcttgg
7251  gtgaatttag ctcttcattg tccctcagct ttttgatatc atcactattg
7301  agttcagtga ggagtttgct catggcaaca catgctgatt gtttagttat
7351  attgtttatt gatcctatat aactctctag cactccaact acaccaagag
7401  catactcttc tgttctgtcc aactctgcag ctccacttat ttctgataag
7451  gtatctatac ttttatccat agacttaagt attctgttta acataaagtt
7501  ttgtcttaca agcagtgcat ggggtggcca ttcaaaataa ttatgactaa
7551  aatgacacct cttaccattt aagcaatgac ctcgaatttc aaatttgcaa
7601  ggattccttc gtgacatatt tgccccagtt ttcattttta cagatggtaa
7651  gttaatctgg cattcaattg tgttttatat aactataaac taggaatcta
7701  cttaaatagt gtaagtgaga tggtttatag atgagagttt cgatgaagtt
7751  cagattttaa gaaaatccaa tgacagatgg gttgtctatg agcagatagt
7801  aaaccattgt aagaacatga ttaggtgcta ttttatttta gttactaaat
7851  gcaatattat ttataccact cagttgatct ttgcttagtg tgactggtgt
7901  gcttctggcc ttacagtata agagcagtcc aacagcaatt aatgataaca
7951  atattactat aatcactata attatagtag ttatcatgat atttgtggtg
8001  gatttaccag catttacatt atgtaataat tcatcggatt tacgaataaa
8051  tgctaggctc tggttaatct tctcgttgac ttgagatatt gatgcatcaa
8101  attcatcaga ggggaatact aatgggtcat agaaatttat tattggttca
8151  ccttttacat agagactttt accttcttgc ttatttacat aatataatgt
8201  gttacctaca gacacagtgt ccatcccttt atttgataca taatcgcacc
8251  cgttagaaaa tgtctttatg attccacgat ttttattgga tgctgtacat
8301  ttagttttgc catagcatga cacaatggct cctagagatg tgataacgga
```

FIG. 1D

```
 8351   gctgcttaca tctgtttttg aagtcataat tttacaatca tatttggggt
 8401   tgaatatgtc aacattgcag agatttattt cacttggtaa tgttaaactg
 8451   ttcattgtgt cacaaaatac tcgatttgat tgaactttac atgtttcagc
 8501   ttgtgggaag aaagatactg atcctgcatt gtcacagtac catcctctgt
 8551   cagttcttgt taaacagatg ttggacccct cttttgtgtt ggttgtacat
 8601   agaggggatg tgtgtagttt ccaacagggt gtatctataa caccatatag
 8651   tggtaattgt actacatatg ctaagacttc ctcttttatt atggacatga
 8701   tagagtaact ttgctgtcta actatttgaa cattgttgga cattaacttt
 8751   ttctgatcat ttgttatagg catatcattg attaatgaca ataattcact
 8801   attagttaac atgtaagtgc ttacaggtgt agttacacct gcattaacac
 8851   taaattccct ggtaatctct agtagtctgt tgttcttttg ttggaactct
 8901   atcacagttt ctatatttga tatgctgcag ctttgcttgt tcacaatagg
 8951   taacaattgt ttatctatat agttttgag gtctaacact ttgctggtta
 9001   agacactaac tccatttgat aagctgacta gagccttgtt tgtggatagt
 9051   agagcacttt tgatcttgtt cacttcccct tctaggtgca ggaccttaga
 9101   tacagcaacg ccactggcga ttgcagatcc aacacctaac aaaaaaacaa
 9151   gaaatcttct tttccttttc ttgcttaatg ttacattggt ttttttggca
 9201   ttgttgagtg tataattcat aaaccttggt agttctcttc tggctcgatt
 9251   gtttgttggt ggtgtgcttt gcatgagcaa ctgcaattct gttacagcat
 9301   ttttatattt atctaattct tgttttatca attttacctt agcatctgtt
 9351   ccattacact tattttcctt gatattactt aattctatag ttataacact
 9401   ggtataccaa ccagttctca gagcactaag atagcctttg ctaactgcac
 9451   tgcatgttga ttgataaaat tcttcagtga tgttttgacc agaagcaaaa
 9501   caaaatgtga ctgcagtgag gattgtggta attgcatttg ctttgaggat
 9551   tagcaactcc attgttattt gccccagagt ttattttgat tctgtttaag
10001   tggtggtggg tatgctgcag ggtacaaagt tggcgttgtt aaagtgaaaa
10051   tcattattgg gtttgcttgg tggtttgttt tggcgttgtt ttgtggtggg
10101   cttgctgggt tgtgtttgag ttgttgttgt gttttggtc ttgactgttg
10151   tggattgcag ggttgacttg actcctggtg ttgttgaagc tagtatggtg
10201   gtgatttgtg atgtaatttc agacggatta gagggactga ttccaagctg
10251   aggattctgg gtgaggtatg ttggggttgt gttcttgatc tggcttgttg
10301   catcttgtat gattgcagtt gttggtgtga ctttgtggtt tgccgaggct
10351   atgaatatga tggctgcaat tataagtgaa gttgagatta tcattgccag
10401   aatggataat gtgatttgtg ctacagattt aagatttaac ttatataagc
10451   acgatgatat gaataataaa tgattgagag tgtcccaggt cctttctaat
10501   gtcttagcgg tgcgttggtc cttgtttttg gacatgtttg catttgcccc
10551   aatgttattg ttagtcttga tatcctagtt cattgttatg actatttta
10601   attaactact ttatagtatg gatagtggtt tgcatggtgg gatgttaatg
10651   aggtgttgta aagaggtagg ggttgttcat ttttaaatgc aaggttactg
10701   ttttgggctg ttggattgat gaatgctatg tgttgactcg agctcttggt
10751   aactcaaagg ttttgttatg gaatacgtta tattcacaaa gtttgtttag
10801   tattgcaatc atgatggaga ttatgattag caaagagatt attgttgtga
```

FIG. 1E

```
10851  tcatgtgtat tagtgtaaag taaggccaga atttgcttga gaattctatt
10901  gttatggatg tattttccat tggttgattc tgtatggtgt gtggacttgt
10951  ctatgttaac agatattgtg attagttgga tttcctccaa tgattatttg
11001  gaaccacaga atatttttta ttaacttatt tgagtactag atctgataaa
11051  caatgacttg ggatgatctg ggacttcaga taagttttgt ttgattggtt
11101  gaaccacaga gtgtttgtga ttgtgatggt gaagtgaaga atgtaggtag
11151  aaagtttgta tgaattaaca cagtgatgta gaggaaaaag gttaatcttc
11201  catgggtttg attgcaaatc gtgtagctgt gtgcttccaa tttgtggtaa
11251  cataatatat actttctttt tctaggtaag ctccaagatc tactatgaat
11301  tgactttgtg gctttatgta tttgaatgct cctttgttgt cagtcactgt
11351  gatgactaat agtaatcctg agtaagggat gatttttgca tttgtgatag
11401  cattttgaa ttcagtggtt gttatatttt caagtgtgtt cagatcttta
11451  tttctgacac tgatggatct taggtatgtt ggtattatga cttttttga
11501  tgttactatg ttttcaaatt cacataaagc aataatatca tgtgtagggt
11551  tgagtgtctt catagtgaga tctttaactg tagtcaacat attttttgat
11601  tttaggcatg ttagactaca tgccttgatt tcacagggtg tggttacatc
11651  atatgctagt ttgcttcttt catccaagga cacattagcg catatggtaa
11701  atttgctggg catttgtgct agcactgcac ttcttgagtt tatcatgact
11751  cttagtgaag gtcccttggg tgtggatatt tgtttcacta gtatgttgac
11801  attagctagt tcttttataa gtaaatctgc tggcatagat gattggaaca
11851  tgggcaccca tattgtaagt gatgcagggt catcgtcttt ttctaagaca
11901  ttgtattgaa cagcagctgt gtatgtggag ccttcgtgaa gcttgttcac
11951  gtatgtttcc atatttgccc cacccttcc ttttttgta actatattat
12001  agatttttc cgggtggtta gttttggatt ggctggttgt tttgttggct
12051  gtttggctga ttggcggatg gatgtttggt tggatgattg ggttggttag
12101  tttgttggtc ttctgttggt attgtgtgtt gatgtgaaga gtggtaacta
12151  atcagaaatc ttcaagtgat agatcattgt cactatcatt cccttccaat
12201  aggttgttca atttctctga tgttggattg agagacactt catctgatgt
12251  gtcttttgcc atcttttcac tttcctcatt cctgagtctt gccatagctt
12301  ctaatctgtc attggtcatt aatgcttcag ttctgatttt ttctatcatt
12351  tcttctctta aaccaatcat ggcatctctt ataccatccc gagcagatgt
12401  aggtcctgca cttgccacta ctaatgtgtg aagcattcct agtatttcac
12451  ttaattttc atcaatccta tctaatcttg ctgttatatt atcgtttgtc
12501  tgatcattta tttcttcgta tgaatagctg gattcttctt cattgttatc
12551  aaatgtttct atggtttctt tgtatagttt agaaaaggga ttatcacttg
12601  gtgtagggtc ttctttgaaa cttactagag gttttctttg ataattgggc
12651  ttgttccctg cagtatcatc tgtctcattt gttgggttga taatagttga
12701  atttgatgtt atagggcttt ctttggttac ttctatatct attgagttga
12801  ccctttattg attctaggaa tttagtagcc ctgttgtttg catcttctcc
12851  atggaattca ggagcaaact tttccatgat gatttatttg ccccattttt
12901  tattaactca aagctctaca tcattatctt ttggattaag ctgatgtttg
12951  atagcctcta gttcttctgc tgtcaagtct agtacactgt agttaatcac
```

```
13001  accattttct ttgagttgtt cagcatatgc ctttgctgca tcatatagat
13051  cttgattcct cggtgtacct ctgtactctc ccattatgcc taggccagca
13101  gcattgccta atactacact ggagaagtga ggaaattgag tcaaagataa
13151  taatgatgct tttgggttgt tcaatatatg gtagaatcct gcttcaccac
13201  ccaattttg ggcatattca taaacctcaa caacttgttc catttctgct
13251  tgcacactag catgtcctaa cataatattt ttaactgatt ttgctaagac
13301  tccccaccgt aacatcactt gccctgcacc ataggcattc ataaacaatc
13351  ctgcaaaaat cccttcaact ctactgccac ctctggtaga agattgtgct
13401  ataccaaaat gaacaaaaac atctataaag tggggatgtt tttcaaacac
13451  ttcatagaag ctgttggcta tgtccttggg tagtaagcct ttgtaacgtt
13501  tcatttcatt ttttaggaca ttattagctc tcctaatcac ggctgtaaga
13551  ccagatctgt cccctgctgc taatttagtt attactaatg ctgctataca
13601  taatattatc atcccacaat caggagagtc atgcctgtat tctggagcta
13651  cctctcccat ttcttttagc attttttgt aggattttct agattctatc
13701  tcaatgttga tttgaatttc agttgttaag cttgccaatg ttaacacttc
13751  aaatttcatt tcttttccat taatgtcttg acgatgtgtt gttacatcta
13801  ctccatttgc ttttacatga tatcccgcat ctctgagtat ttttatggtg
13851  tcttctcttc ctaacctaga catcgcatat aacataccta ttaacccagt
13901  gaatttatga ttagcatctt ctgtgattaa taacatgcca cataacttat
13951  tgatgtgttt ctgcacatca taattaggag tatcaatact atctcctgtg
14001  ctccgttgga tggtgtattt gctggatgac agaagttgat ctttgttgag
14051  tgtatcattc aacttgactt tgctaagagc catctttgta tttgccccat
14101  cttctatctt atatctctcc ttaattttaa attactataa ttttcaggct
14151  ccatctggac tatggagtat agttatgcat agagttgttg ttttagattg
14201  tgtgaatatt gtgttgaaat ttatggattg agatcatact tgtatattat
14251  gggagtatgc tttgtaggct taatgccaat gcattctaag aacccatcat
14301  gattgatgaa tattggcata gggaaagtgc catattttgt gttgtattca
14351  gtatattttt tatatttagt gcttcctact ttgtgtaata gtttcatttc
14401  atagttgacc aggaatgtaa atgtggcctg tttttcatca agttttctca
14451  ctatgcattc atgatttatc aagtatataa atttgtgtgt tatgatgtct
14501  ctggttagtg atgttattat ggtctcaagt gacaacggtc tcatgtctgt
14551  gatcatcagt ctttgtggtg tattatcatt gtgggttgtg tccatggttg
14601  ggttggctga attgatttat ttgccccatt tttgtcttct gttaagtttt
14651  atattaacta atggtgttag tgacattgat ttgctagttg atattaatta
14701  taatttatgg attaagatca aatccaagta attcagataa ttgattcata
14751  taattggtca ttgttgaatc acttagtttt ttggagaatt taatttcaca
14801  attgtcatct agtagaccat taggttgaga gcaatgtgtt aattccatca
14851  tttcccatat ataacctcca ttttgtagta ctggcattgt tgtgaaattg
14901  gattttacta caatattatt attagggcaa atatcactac ttgtaataac
```

FIG. 1G

```
14951  atgcacaaac acaatgccat tcaatttgat tgtatgtatc actgccttag
15001  ccaaagcgtt agttaaatgt attaatttat cagtatagca tgttattttt
15051  aacaatgcta cttcatcatt gtcaaacaaa ttttgtaatc taacttttat
15101  catactcaat gaattgctgc ccatctctaa ccaagggagt taaatttaag
15151  tggtacttat caaattctta tttgccccat tttttggtt tatgcaagtt
15201  tgttgtacgc attttttcgc gt
```

FIG. 1H

SEQUENCE LISTING (1) GENERAL INFORMATION:

(iii) NUMBER OF SEQUENCES: 29

(2) INFORMATION FOR SEQ ID NO:1:

(i) SEQUENCE CHARACTERISTICS:
      (A) LENGTH: 19 base pairs
      (B) TYPE: nucleic acid
      (C) STRANDEDNESS: single
      (D) TOPOLOGY: linear (ii) MOLECULE TYPE: DNA (ix) FEATURE:
      (A) NAME/KEY: RSV (L )
      (B) LOCATION: 1...19
      (D) OTHER INFORMATION:

(xi) SEQUENCE DESCRIPTION: SEQ ID NO:1:

TCAATGGTCC TTATCTCAA                                        19

(2) INFORMATION FOR SEQ ID NO:2:

(i) SEQUENCE CHARACTERISTICS:
      (A) LENGTH: 19 base pairs
      (B) TYPE: nucleic acid
      (C) STRANDEDNESS: single
      (D) TOPOLOGY: linear (ii) MOLECULE TYPE: DNA (ix) FEATURE:
      (A) NAME/KEY: RSV (L-)
      (B) LOCATION: 1...19
      (D) OTHER INFORMATION:

(xi) SEQUENCE DESCRIPTION: SEQ ID NO:2:

GAGCTTTATT AGCAGCATC                                        19

(2) INFORMATION FOR SEQ ID NO:3:

(i) SEQUENCE CHARACTERISTICS:
      (A) LENGTH: 19 base pairs
      (B) TYPE: nucleic acid
      (C) STRANDEDNESS: single
      (D) TOPOLOGY: linear (ii) MOLECULE TYPE: DNA (ix) FEATURE:
      (A) NAME/KEY: GAPDH ( )
      (B) LOCATION: 1...19
      (D) OTHER INFORMATION:

(xi) SEQUENCE DESCRIPTION: SEQ ID NO:3:

AAATCCCATC ACCATCTTC                                        19

(2) INFORMATION FOR SEQ ID NO:4:

(i) SEQUENCE CHARACTERISTICS:
      (A) LENGTH: 19 base pairs
      (B) TYPE: nucleic acid
      (C) STRANDEDNESS: single
      (D) TOPOLOGY: linear (ii) MOLECULE TYPE: DNA (ix) FEATURE:

(A) NAME/KEY: GAPDH (-)
        (B) LOCATION: 1...19
        (D) OTHER INFORMATION:

(xi) SEQUENCE DESCRIPTION: SEQ ID NO:4:

CACCACCCTG TTGCTGTAG                                                        19

(2) INFORMATION FOR SEQ ID NO:5:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: RSV (M2 )
        (B) LOCATION: 1...19
        (D) OTHER INFORMATION:

(xi) SEQUENCE DESCRIPTION: SEQ ID NO:5:

AAACAATCAG CATGTGTTG                                                        19

(2) INFORMATION FOR SEQ ID NO:6:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: RSV (M2-)
        (B) LOCATION: 1...19
        (D) OTHER INFORMATION:

(xi) SEQUENCE DESCRIPTION: SEQ ID NO:6:

AATGTAACGA TGTGGTGAG                                                        19

(2) INFORMATION FOR SEQ ID NO:7:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: Activator-antisense complex
        (B) LOCATION: 1...19
        (D) OTHER INFORMATION: spA4-antiRSV3'-3'T/(1-19)

(xi) SEQUENCE DESCRIPTION: SEQ ID NO:7:

TTGTACGCAT TTTTTCGCG                                                        19

(2) INFORMATION FOR SEQ ID NO:8:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (ix) FEATURE:

(A) NAME/KEY: Activator-antisense complex
            (B) LOCATION: 1...19
            (D) OTHER INFORMATION: spA4-antiRSV3'-3'T/(51-69)

(xi) SEQUENCE DESCRIPTION: SEQ ID NO:8:

GTACTTATCA AATTCTTAT                                                          19

(2) INFORMATION FOR SEQ ID NO:9:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: Activator-antisense complex
            (B) LOCATION: 1...18
            (D) OTHER INFORMATION: spA4-antiRSVGe3'-3'T/(1-18)

(xi) SEQUENCE DESCRIPTION: SEQ ID NO:9:

ACGCGAAAAA ATGCGTAC                                                           18

(2) INFORMATION FOR SEQ ID NO:10:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: Activator-antisense complex
            (B) LOCATION: 1...18
            (D) OTHER INFORMATION: spA4-antiRSVGe3'-3'T/(84-101)

(xi) SEQUENCE DESCRIPTION: SEQ ID NO:10:

CTCCCTTGGT TAGAGATG                                                           18

(2) INFORMATION FOR SEQ ID NO:11:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: Activator-antisense complex
            (B) LOCATION: 1...18
            (D) OTHER INFORMATION: spA4-antiRSVGe3'T/(369-386)

(xi) SEQUENCE DESCRIPTION: SEQ ID NO:11:

GAAATGATGG AATTAACA                                                           18

(2) INFORMATION FOR SEQ ID NO:12:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (ix) FEATURE:

(A) NAME/KEY: Oligonucleotide
            (B) LOCATION: 1...19
            (D) OTHER INFORMATION: A4-antiRSV3'-3C/(8490-8509)

(xi) SEQUENCE DESCRIPTION: SEQ ID NO:12:

AATGGGATCC ATTTTGTCC                                                       19

(2) INFORMATION FOR SEQ ID NO:13:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: Oligonucleotide
            (B) LOCATION: 1...20
            (D) OTHER INFORMATION: pA4-antiRSV/(8490-8509)

(xi) SEQUENCE DESCRIPTION: SEQ ID NO:13:

AATGGGATCC ATTTTGTCCC                                                      20

(2) INFORMATION FOR SEQ ID NO:14:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: Oligonucleotide
            (B) LOCATION: 1...20
            (D) OTHER INFORMATION: pA4-3'antiRSV5'/(8490-8509)

(xi) SEQUENCE DESCRIPTION: SEQ ID NO:14:

AATGGGATCC ATTTTGTCCC                                                      20

(2) INFORMATION FOR SEQ ID NO:15:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: Oligonucleotide
            (B) LOCATION: 1...19
            (D) OTHER INFORMATION: pA4-antiRSV3'-3'C/(8490-8509)

(xi) SEQUENCE DESCRIPTION: SEQ ID NO:15:

AATGGGATCC ATTTTGTCC                                                       19

(2) INFORMATION FOR SEQ ID NO:16:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (ix) FEATURE:

(A) NAME/KEY: Oligonucleotide
        (B) LOCATION: 1...20
        (D) OTHER INFORMATION: spA4-antiRSV/(8490-8509)

(xi) SEQUENCE DESCRIPTION: SEQ ID NO:16:

AATGGGATCC ATTTTGTCCC                                                    20

(2) INFORMATION FOR SEQ ID NO:17:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: Oligonucleotide
        (B) LOCATION: 1...17
        (D) OTHER INFORMATION: spA4-antiRSV3'-3'A/(8530-8547)

(xi) SEQUENCE DESCRIPTION: SEQ ID NO:17:

CTATCGGTTA GATAAAC                                                       17

(2) INFORMATION FOR SEQ ID NO:18:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: Oligonucleotide
        (B) LOCATION: 1...19
        (D) OTHER INFORMATION: spA4-antiRSV3'-3'G/(8599-
            8618)

(xi) SEQUENCE DESCRIPTION: SEQ ID NO:18:

GATAAGGACC ATTGAATAT                                                     19

(2) INFORMATION FOR SEQ ID NO:19:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: Oligonucleotide
        (B) LOCATION: 1...17
        (D) OTHER INFORMATION: spA4-antiRSV3'-3'C/(8561-8578)

(xi) SEQUENCE DESCRIPTION: SEQ ID NO:19:

CTCTGAGAAA GAGATAA                                                       17

(2) INFORMATION FOR SEQ ID NO:20:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:
    (A) NAME/KEY: Oligonucleotide
    (B) LOCATION: 1...18
    (D) OTHER INFORMATION: spA4-antiRSV3'-3'T/(8261-8279)

(xi) SEQUENCE DESCRIPTION: SEQ ID NO:20:

GATTGAAATA TAGTGTGT                                                    18

(2) INFORMATION FOR SEQ ID NO:21:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: Other
        (B) LOCATION: 1...19
        (D) OTHER INFORMATION: Oligonucleotide spA4-anti
            RSV3'-3'A/(8251-8270)

(xi) SEQUENCE DESCRIPTION: SEQ ID NO:21:

ATAGTGTGTT CTTTTGATT                                                   19

(2) INFORMATION FOR SEQ ID NO:22:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: Oligonucleotide
        (B) LOCATION: 1...18
        (D) OTHER INFORMATION: spA4-antiRSV3'-3'T/(8281-8299)

(xi) SEQUENCE DESCRIPTION: SEQ ID NO:22:

ATGGTTATTT GGGTTGTT                                                    18

(2) INFORMATION FOR SEQ ID NO:23:

(i) SEQUENCE CHARACTERISTICS:
        (A) LENGTH: 15222 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: RSV-A2
        (B) LOCATION: 1...15222
        (D) OTHER INFORMATION:

(xi) SEQUENCE DESCRIPTION: SEQ ID NO:23:

ACGCGAAAAA ATGCGTACAA CAAACTTGCA TAAACCAAAA AAATGGGGCA AATAAGAATT      60

TGATAAGTAC CACTTAAATT TAACTCCCTT GGTTAGAGAT GGGCAGCAAT TCATTGAGTA     120

TGATAAAAGT TAGATTACAA AATTTGTTTG ACAATGATGA AGTAGCATTG TTAAAAATAA     180

CATGCTATAC TGATAAATTA ATACATTTAA CTAACGCTTT GGCTAAGGCA GTGATACATA     240

CAATCAAATT GAATGGCATT GTGTTTGTGC ATGTTATTAC AAGTAGTGAT ATTTGCCCTA     300

ATAATAATAT TGTAGTAAAA TCCAATTTCA CAACAATGCC AGTACTACAA AATGGAGGTT     360

```
ATATATGGGA AATGATGGAA TTAACACATT GCTCTCAACC TAATGGTCTA CTAGATGACA    420

ATTGTGAAAT TAAATTCTCC AAAAAACTAA GTGATTCAAC AATGACCAAT TATATGAATC    480

AATTATCTGA ATTACTTGGA TTTGATCTTA ATCCATAAAT TATAATTAAT ATCAACTAGC    540

AAATCAATGT CACTAACACC ATTAGTTAAT ATAAAACTTA ACAGAAGACA AAAATGGGGC    600

AAATAAATCA ATTCAGCCAA CCCAACCATG GACACAACCC ACAATGATAA TACACCACAA    660

AGACTGATGA TCACAGACAT GAGACCGTTG TCACTTGAGA CCATAATAAC ATCACTAACC    720

AGAGACATCA TAACACACAA ATTTATATAC TTGATAAATC ATGAATGCAT AGTGAGAAAA    780

CTTGATGAAA AACAGGCCAC ATTTACATTC CTGGTCAACT ATGAAATGAA ACTATTACAC    840

AAAGTAGGAA GCACTAAATA TAAAAAATAT ACTGAATACA ACACAAAATA TGGCACTTTC    900

CCTATGCCAA TATTCATCAA TCATGATGGG TTCTTAGAAT GCATTGGCAT TAAGCCTACA    960

AAGCATACTC CCATAATATA CAAGTATGAT CTCAATCCAT AAATTTCAAC ACAATATTCA   1020

CACAATCTAA AACAACAACT CTATGCATAA CTATACTCCA TAGTCCAGAT GGAGCCTGAA   1080

AATTATAGTA ATTTAAAATT AAGGAGAGAT ATAAGATAGA AGATGGGCA AATACAAAGA    1140

TGGCTCTTAG CAAAGTCAAG TTGAATGATA CACTCAACAA AGATCAACTT CTGTCATCCA   1200

GCAAATACAC CATCCAACGG AGCACAGGAG ATAGTATTGA TACTCCTAAT TATGATGTGC   1260

AGAAACACAT CAATAAGTTA TGTGGCATGT TATTAATCAC AGAAGATGCT AATCATAAAT   1320

TCACTGGGTT AATAGGTATG TTATATGCGA TGTCTAGGTT AGGAAGAGAA GACACCATAA   1380

AAATACTCAG AGATGCGGGA TATCATGTAA AAGCAAATGG AGTAGATGTA ACAACACATC   1440

GTCAAGACAT TAATGGAAAA GAAATGAAAT TTGAAGTGTT AACATTGGCA AGCTTAACAA   1500

CTGAAATTCA AATCAACATT GAGATAGAAT CTAGAAAATC CTACAAAAAA ATGCTAAAAG   1560

AAATGGGAGA GGTAGCTCCA GAATACAGGC ATGACTCTCC TGATTGTGGG ATGATAATAT   1620

TATGTATAGC AGCATTAGTA ATAACTAAAT TAGCAGCAGG GGACAGATCT GGTCTTACAG   1680

CCGTGATTAG GAGAGCTAAT AATGTCCTAA AAAATGAAAT GAAACGTTAC AAAGGCTTAC   1740

TACCCAAGGA CATAGCCAAC AGCTTCTATG AAGTGTTTGA AAAACATCCC CACTTTATAG   1800

ATGTTTTTGT TCATTTTGGT ATAGCACAAT CTTCTACCAG AGGTGGCAGT AGAGTTGAAG   1860

GGATTTTTGC AGGATTGTTT ATGAATGCCT ATGGTGCAGG GCAAGTGATG TTACGGTGGG   1920

GAGTCTTAGC AAAATCAGTT AAAAATATTA TGTTAGGACA TGCTAGTGTG CAAGCAGAAA   1980

TGGAACAAGT TGTTGAGGTT TATGAATATG CCCAAAAATT GGGTGGTGAA GCAGGATTCT   2040

ACCATATATT GAACAACCCA AAAGCATCAT TATTATCTTT GACTCAATTT CCTCACTTCT   2100

CCAGTGTAGT ATTAGGCAAT GCTGCTGGCC TAGGCATAAT GGGAGAGTAC AGAGGTACAC   2160

CGAGGAATCA AGATCTATAT GATGCAGCAA AGGCATATGC TGAACAACTC AAAGAAAATG   2220

GTGTGATTAA CTACAGTGTA CTAGACTTGA CAGCAGAAGA ACTAGAGGCT ATCAAACATC   2280

AGCTTAATCC AAAAGATAAT GATGTAGAGC TTTGAGTTAA TAAAAAATGG GGCAAATAAA   2340

TCATCATGGA AAAGTTTGCT CCTGAATTCC ATGGAGAAGA TGCAAACAAC AGGGCTACTA   2400

AATTCCTAGA ATCAATAAAG GGCAAATTCA CATCACCCAA AGATCCCAAG AAAAAAGATA   2460

GTATCATATC TGTCAACTCA ATAGATATAG AAGTAACCAA AGAAAGCCCT ATAACATCAA   2520

ATTCAACTAT TATCAACCCA ACAAATGAGA CAGATGATAC TGCAGGGAAC AAGCCCAATT   2580

ATCAAAGAAA ACCTCTAGTA AGTTTCAAAG AAGACCCTAC ACCAAGTGAT AATCCCTTTT   2640

CTAAACTATA CAAAGAAACC ATAGAAACAT TTGATAACAA TGAAGAAGAA TCCAGCTATT   2700

CATACGAAGA AATAAATGAT CAGACAAACG ATAATATAAC AGCAAGATTA GATAGGATTG   2760
```

-continued

```
ATGAAAAATT AAGTGAAATA CTAGGAATGC TTCACACATT AGTAGTGGCA AGTGCAGGAC    2820

CTACATCTGC TCGGGATGGT ATAAGAGATG CCATGATTGG TTTAAGAGAA GAAATGATAG    2880

AAAAAATCAG AACTGAAGCA TTAATGACCA ATGACAGATT AGAAGCTATG GCAAGACTCA    2940

GGAATGAGGA AAGTGAAAAG ATGGCAAAAG ACACATCAGA TGAAGTGTCT CTCAATCCAA    3000

CATCAGAGAA ATTGAACAAC CTATTGGAAG GGAATGATAG TGACAATGAT CTATCACTTG    3060

AAGATTTCTG ATTAGTTACC ACTCTTCACA TCAACACACA ATACCAACAG AAGACCAACA    3120

AACTAACCAA CCCAATCATC CAACCAAACA TCCATCCGCC AATCAGCCAA CAGCCAACA     3180

AAACAACCAG CCAATCCAAA ACTAACCACC CGGAAAAAAT CTATAATATA GTTACAAAAA    3240

AAGGAAAGGG TGGGGCAAAT ATGGAAACAT ACGTGAACAA GCTTCACGAA GGCTCCACAT    3300

ACACAGCTGC TGTTCAATAC AATGTCTTAG AAAAAGACGA TGACCCTGCA TCACTTACAA    3360

TATGGGTGCC CATGTTCCAA TCATCTATGC CAGCAGATTT ACTTATAAAA GAACTAGCTA    3420

ATGTCAACAT ACTAGTGAAA CAAATATCCA CACCCAAGGG ACCTTCACTA AGAGTCATGA    3480

TAAACTCAAG AAGTGCAGTG CTAGCACAAA TGCCCAGCAA ATTTACCATA TGCGCTAATG    3540

TGTCCTTGGA TGAAAGAAGC AAACTAGCAT ATGATGTAAC CACACCCTGT GAAATCAAGG    3600

CATGTAGTCT AACATGCCTA AAATCAAAAA ATATGTTGAC TACAGTTAAA GATCTCACTA    3660

TGAAGACACT CAACCCTACA CATGATATTA TTGCTTTATG TGAATTTGAA AACATAGTAA    3720

CATCAAAAAA AGTCATAATA CCAACATACC TAAGATCCAT CAGTGTCAGA AATAAAGATC    3780

TGAACACACT TGAAAATATA ACAACCACTG AATTCAAAAA TGCTATCACA AATGCAAAAA    3840

TCATCCCTTA CTCAGGATTA CTATTAGTCA TCACAGTGAC TGACAACAAA GGAGCATTCA    3900

AATACATAAA GCCACAAAGT CAATTCATAG TAGATCTTGG AGCTTACCTA GAAAAAGAAA    3960

GTATATATTA TGTTACCACA AATTGGAAGC ACACAGCTAC ACGATTTGCA ATCAAACCCA    4020

TGGAAGATTA ACCTTTTTCC TCTACATCAG TGTGTTAATT CATACAAACT TTCTACCTAC    4080

ATTCTTCACT TCACCATCAC AATCACAAAC ACTCTGTGGT TCAACCAATC AAACAAAACT    4140

TATCTGAAGT CCCAGATCAT CCCAAGTCAT TGTTTATCAG ATCTAGTACT CAAATAAGTT    4200

AATAAAAAAT ATACACATGG GGCAAATAAT CATTGGAGGA AATCCAACTA ATCACAATAT    4260

CTGTTAACAT AGACAAGTCC ACACACCATA CAGAATCAAC CAATGGAAAA TACATCCATA    4320

ACAATAGAAT TCTCAAGCAA ATTCTGGCCT TACTTTACAC TAATACACAT GATCACAACA    4380

ATAATCTCTT TGCTAATCAT AATCTCCATC ATGATTGCAA TACTAAACAA ACTTTGTGAA    4440

TATAACGTAT TCCATAACAA AACCTTTGAG TTACCAAGAG CTCGAGTCAA CACATAGCAT    4500

TCATCAATCC AACAGCCCAA AACAGTAACC TTGCATTTAA AAATGAACAA CCCCTACCTC    4560

TTTACAACAC CTCATTAACA TCCCACCATG CAAACCACTA TCCATACTAT AAAGTAGTTA    4620

ATTAAAAATA GTCATAACAA TGAACTAGGA TATCAAGACT AACAATAACA TTGGGGCAAA    4680

TGCAAACATG TCCAAAAACA AGGACCAACG CACCGCTAAG ACATTAGAAA GGACCTGGGA    4740

CACTCTCAAT CATTTATTAT TCATATCATC GTGCTTATAT AAGTTAAATC TTAAATCTGT    4800

AGCACAAATC ACATTATCCA TTCTGGCAAT GATAATCTCA ACTTCACTTA TAATTGCAGC    4860

CATCATATTC ATAGCCTCGG CAAACCACAA AGTCACACCA ACAACTGCAA TCATACAAGA    4920

TGCAACAAGC CAGATCAAGA ACACAACCCC AACATACCTC ACCCAGAATC CTCAGCTTGG    4980

AATCAGTCCC TCTAATCCGT CTGAAATTAC ATCACAAATC ACCACCATAC TAGCTTCAAC    5040

AACACCAGGA GTCAAGTCAA CCCTGCAATC CACAACAGTC AAGACCAAAA ACACAACAAC    5100

AACTCAAACA CAACCCAGCA AGCCCACCAC AAAACAACGC CAAAACAAAC CACCAAGCAA    5160
```

-continued

```
ACCCAATAAT GATTTTCACT TTGAAGTGTT CAACTTTGTA CCCTGCAGCA TATGCAGCAA    5220
CAATCCAACC TGCTGGGCTA TCTGCAAAAG AATACCAAAC AAAAAACCAG GAAAGAAAAC    5280
CACTACCAAG CCCACAAAAA AACCAACCCT CAAGACAACC AAAAAAGATC CCAAACCTCA    5340
AACCACTAAA TCAAAGGAAG TACCCACCAC CAAGCCCACA GAAGAGCCAA CCATCAACAC    5400
CACCAAAACA AACATCATAA CTACACTACT CACCTCCAAC ACCACAGGAA ATCCAGAACT    5460
CACAAGTCAA ATGGAAACCT TCCACTCAAC TTCCTCCGAA GGCAATCCAA GCCCTTCTCA    5520
AGTCTCTACA ACATCCGAGT ACCCATCACA ACCTTCATCT CCACCCAACA CACCACGCCA    5580
GTAGTTACTT AAAAACATAT TATCACAAAA AGCCATGACC AACTTAAACA GAATCAAAAT    5640
AAACTCTGGG GCAAATAACA ATGGAGTTGC TAATCCTCAA AGCAAATGCA ATTACCACAA    5700
TCCTCACTGC AGTCACATTT TGTTTTGCTT CTGGTCAAAA CATCACTGAA GAATTTTATC    5760
AATCAACATG CAGTGCAGTT AGCAAAGGCT ATCTTAGTGC TCTGAGAACT GGTTGGTATA    5820
CCAGTGTTAT AACTATAGAA TTAAGTAATA TCAAGGAAAA TAAGTGTAAT GGAACAGATG    5880
CTAAGGTAAA ATTGATAAAA CAAGAATTAG ATAAATATAA AAATGCTGTA ACAGAATTGC    5940
AGTTGCTCAT GCAAAGCACA CCACCAACAA ACAATCGAGC CAGAAGAGAA CTACCAAGGT    6000
TTATGAATTA TACACTCAAC AATGCCAAAA AAACCAATGT AACATTAAGC AAGAAAAGGA    6060
AAAGAAGATT TCTTGTTTTT TTGTTAGGTG TTGGATCTGC AATCGCCAGT GGCGTTGCTG    6120
TATCTAAGGT CCTGCACCTA GAAGGGGAAG TGAACAAGAT CAAAAGTGCT CTACTATCCA    6180
CAAACAAGGC TCTAGTCAGC TTATCAAATG GAGTTAGTGT CTTAACCAGC AAAGTGTTAG    6240
ACCTCAAAAA CTATATAGAT AAACAATTGT TACCTATTGT GAACAAGCAA AGCTGCAGCA    6300
TATCAAATAT AGAAACTGTG ATAGAGTTCC AACAAAAGAA CAACAGACTA CTAGAGATTA    6360
CCAGGGAATT TAGTGTTAAT GCAGGTGTAA CTACACCTGT AAGCACTTAC ATGTTAACTA    6420
ATAGTGAATT ATTGTCATTA ATCAATGATA TGCCTATAAC AAATGATCAG AAAAAGTTAA    6480
TGTCCAACAA TGTTCAAATA GTTAGACAGC AAAGTTACTC TATCATGTCC ATAATAAAAG    6540
AGGAAGTCTT AGCATATGTA GTACAATTAC CACTATATGG TGTTATAGAT ACACCCTGTT    6600
GGAAACTACA CACATCCCCT CTATGTACAA CCAACACAAA AGAAGGGTCC AACATCTGTT    6660
TAACAAGAAC TGACAGAGGA TGGTACTGTG ACAATGCAGG ATCAGTATCT TTCTTCCCAC    6720
AAGCTGAAAC ATGTAAAGTT CAATCAAATC GAGTATTTTG TGACACAATG AACAGTTTAA    6780
CATTACCAAG TGAAATAAAT CTCTGCAATG TTGACATATT CAACCCCAAA TATGATTGTA    6840
AAATTATGAC TTCAAAAACA GATGTAAGCA GCTCCGTTAT CACATCTCTA GGAGCCATTG    6900
TGTCATGCTA TGGCAAAACT AAATGTACAG CATCCAATAA AAATCGTGGA ATCATAAAGA    6960
CATTTTCTAA CGGGTGCGAT TATGTATCAA ATAAAGGGAT GGACACTGTG TCTGTAGGTA    7020
ACACATTATA TTATGTAAAT AAGCAAGAAG GTAAAAGTCT CTATGTAAAA GGTGAACCAA    7080
TAATAAATTT CTATGACCCA TTAGTATTCC CCTCTGATGA ATTTGATGCA TCAATATCTC    7140
AAGTCAACGA GAAGATTAAC CAGAGCCTAG CATTTATTCG TAAATCCGAT GAATTATTAC    7200
ATAATGTAAA TGCTGGTAAA TCCACCACAA ATATCATGAT AACTACTATA ATTATAGTGA    7260
TTATAGTAAT ATTGTTATCA TTAATTGCTG TTGGACTGCT CTTATACTGT AAGGCCAGAA    7320
GCACACCAGT CACACTAAGC AAAGATCAAC TGAGTGGTAT AAATAATATT GCATTTAGTA    7380
ACTAAATAAA AATAGCACCT AATCATGTTC TTACAATGGT TTACTATCTG CTCATAGACA    7440
ACCCATCTGT CATTGGATTT TCTTAAAATC TGAACTTCAT CGAAACTCTC ATCTATAAAC    7500
CATCTCACTT ACACTATTTA AGTAGATTCC TAGTTTATAG TTATATAAAA CACAATTGAA    7560
```

```
TGCCAGATTA ACTTACCATC TGTAAAAATG AAAACTGGGG CAAATATGTC ACGAAGGAAT    7620

CCTTGCAAAT TTGAAATTCG AGGTCATTGC TTAAATGGTA AGAGGTGTCA TTTTAGTCAT    7680

AATTATTTTG AATGGCCACC CCATGCACTG CTTGTAAGAC AAAACTTTAT GTTAAACAGA    7740

ATACTTAAGT CTATGGATAA AAGTATAGAT ACCTTATCAG AAATAAGTGG AGCTGCAGAG    7800

TTGGACAGAA CAGAAGAGTA TGCTCTTGGT GTAGTTGGAG TGCTAGAGAG TTATATAGGA    7860

TCAATAAACA ATATAACTAA ACAATCAGCA TGTGTTGCCA TGAGCAAACT CCTCACTGAA    7920

CTCAATAGTG ATGATATCAA AAAGCTGAGG GACAATGAAG AGCTAAATTC ACCCAAGATA    7980

AGAGTGTACA ATACTGTCAT ATCATATATT GAAAGCAACA GGAAAAACAA TAAACAAACT    8040

ATCCATCTGT TAAAAAGATT GCCAGCAGAC GTATTGAAGA AAACCATCAA AACACATTG     8100

GATATCCATA AGAGCATAAC CATCAACAAC CCAAAAGAAT CAACTGTTAG TGATACAAAT    8160

GACCATGCCA AAAATAATGA TACTACCTGA CAAATATCCT TGTAGTATAA CTTCCATACT    8220

AATAACAAGT AGATGTAGAG TTACTATGTA TAATCAAAAG AACACACTAT ATTTCAATCA    8280

AAACAACCCA AATAACCATA TGTACTCACC GAATCAAACA TTCAATGAAA TCCATTGGAC    8340

CTCTCAAGAA TTGATTGACA CAATTCAAAT TTTTCTACAA CATCTAGGTA TTATTGAGGA    8400

TATATATACA ATATATATAT TAGTGTCATA ACACTCAATT CTAACACTCA CCACATCGTT    8460

ACATTATTAA TTCAAACAAT TCAAGTTGTG GGACAAAATG GATCCCATTA TTAATGGAAA    8520

TTCTGCTAAT GTTTATCTAA CCGATAGTTA TTTAAAAGGT GTTATCTCTT TCTCAGAGTG    8580

TAATGCTTTA GGAAGTTACA TATTCAATGG TCCTTATCTC AAAAATGATT ATACCAACTT    8640

AATTAGTAGA CAAAATCCAT TAATAGAACA CATGAATCTA AGAAACTAA ATATAACACA     8700

GTCCTTAATA TCTAAGTATC ATAAAGGTGA AATAAAATTA GAAGAACCTA CTTATTTTCA    8760

GTCATTACTT ATGACATACA AGAGTATGAC CTCGTCAGAA CAGATTGCTA CCACTAATTT    8820

ACTTAAAAAG ATAATAAGAA GAGCTATAGA AATAAGTGAT GTCAAAGTCT ATGCTATATT    8880

GAATAAACTA GGGCTTAAAG AAAAGGACAA GATTAAATCC AACAATGGAC AAGATGAAGA    8940

CAACTCAGTT ATTACGACCA TAATCAAAGA TGATATACTT TCAGCTGTTA AAGATAATCA    9000

ATCTCATCTT AAAGCAGACA AAAATCACTC TACAAAACAA AAAGACACAA TCAAACAAC     9060

ACTCTTGAAG AAATTGATGT GTTCAATGCA ACATCCTCCA TCATGGTTAA TACATTGGTT    9120

TAACTTATAC ACAAAATTAA ACAACATATT AACACAGTAT CGATCAAATG AGGTAAAAAA    9180

CCATGGGTTT ACATTGATAG ATAATCAAAC TCTTAGTGGA TTTCAATTTA TTTTGAACCA    9240

ATATGGTTGT ATAGTTTATC ATAAGGAACT CAAAAGAATT ACTGTGACAA CCTATAATCA    9300

ATTCTTGACA TGGAAAGATA TTAGCCTTAG TAGATTAAAT GTTTGTTTAA TTACATGGAT    9360

TAGTAACTGC TTGAACACAT TAAATAAAAG CTTAGGCTTA AGATGCGGAT TCAATAATGT    9420

TATCTTGACA CAACTATTCC TTTATGGAGA TTGTATACTA AAGCTATTTC ACAATGAGGG    9480

GTTCTACATA ATAAAAGAGG TAGAGGGATT TATTATGTCT CTAATTTTAA ATATAACAGA    9540

AGAAGATCAA TTCAGAAAAC GATTTTATAA TAGTATGCTC AACAACATCA CAGATGCTGC    9600

TAATAAAGCT CAGAAAAATC TGCTATCAAG AGTATGTCAT ACATTATTAG ATAAGACAGT    9660

GTCCGATAAT ATAATAAATG GCAGATGGAT AATTCTATTA AGTAAGTTCC TTAAATTAAT    9720

TAAGCTTGCA GGTGACAATA ACCTTAACAA TCTGAGTGAA CTATATTTTT TGTTCAGAAT    9780

ATTTGGACAC CCAATGGTAG ATGAAAGACA AGCCATGGAT GCTGTTAAAA TTAATTGCAA    9840

TGAGACCAAA TTTTACTTGT TAAGCAGTCT GAGTATGTTA AGAGGTGCCT TTATATATAG    9900

AATTATAAAA GGGTTTGTAA ATAATTACAA CAGATGGCCT ACTTTAAGAA ATGCTATTGT    9960
```

```
TTTACCCTTA AGATGGTTAA CTTACTATAA ACTAAACACT TATCCTTCTT TGTTGGAACT 10020

TACAGAAAGA GATTTGATTG TGTTATCAGG ACTACGTTTC TATCGTGAGT TTCGGTTGCC 10080

TAAAAAAGTG GATCTTGAAA TGATTATAAA TGATAAAGCT ATATCACCTC CTAAAAATTT 10140

GATATGGACT AGTTTCCCTA GAAATTACAT GCCATCACAC ATACAAAACT ATATAGAACA 10200

TGAAAAATTA AAATTTTCCG AGAGTGATAA ATCAAGAAGA GTATTAGAGT ATTATTTAAG 10260

AGATAACAAA TTCAATGAAT GTGATTTATA CAACTGTGTA GTTAATCAAA GTTATCTCAA 10320

CAACCCTAAT CATGTGGTAT CATTGACAGG CAAAGAAAGA GAACTCAGTG TAGGTAGAAT 10380

GTTTGCAATG CAACCGGGAA TGTTCAGACA GGTTCAAATA TTGGCAGAGA AAATGATAGC 10440

TGAAAACATT TTACAATTCT TTCCTGAAAG TCTTACAAGA TATGGTGATC TAGAACTACA 10500

AAAAATATTA GAATTGAAAG CAGGAATAAG TAACAAATCA AATCGCTACA ATGATAATTA 10560

CAACAATTAC ATTAGTAAGT GCTCTATCAT CACAGATCTC AGCAAATTCA ATCAAGCATT 10620

TCGATATGAA ACGTCATGTA TTTGTAGTGA TGTGCTGGAT GAACTGCATG GTGTACAATC 10680

TCTATTTTCC TGGTTACATT TAACTATTCC TCATGTCACA ATAATATGCA CATATAGGCA 10740

TGCACCCCCC TATATAGGAG ATCATATTGT AGATCTTAAC AATGTAGATG AACAAAGTGG 10800

ATTATATAGA TATCACATGG GTGGCATCGA AGGGTGGTGT CAAAAACTGT GGACCATAGA 10860

AGCTATATCA CTATTGGATC TAATATCTCT CAAAGGGAAA TTCTCAATTA CTGCTTTAAT 10920

TAATGGTGAC AATCAATCAA TAGATATAAG CAAACCAATC AGACTCATGG AAGGTCAAAC 10980

TCATGCTCAA GCAGATTATT TGCTAGCATT AAATAGCCTT AAATTACTGT ATAAAGAGTA 11040

TGCAGGCATA GGCCACAAAT TAAAAGGAAC TGAGACTTAT ATATCACGAG ATATGCAATT 11100

TATGAGTAAA ACAATTCAAC ATAACGGTGT ATATTACCCA GCTAGTATAA AGAAAGTCCT 11160

AAGAGTGGGA CCGTGGATAA ACACTATACT TGATGATTTC AAAGTGAGTC TAGAATCTAT 11220

AGGTAGTTTG ACACAAGAAT TAGAATATAG AGGTGAAAGT CTATTATGCA GTTAATATT 11280

TAGAAATGTA TGGTTATATA ATCAGATTGC TCTACAATTA AAAAATCATG CATTATGTAA 11340

CAATAAACTA TATTTGGACA TATTAAAGGT TCTGAAACAC TTAAAAACCT TTTTTAATCT 11400

TGATAATATT GATACAGCAT TAACATTGTA TATGAATTTA CCCATGTTAT TTGGTGGTGG 11460

TGATCCCAAC TTGTTATATC GAAGTTTCTA TAGAAGAACT CCTGACTTCC TCACAGAGGC 11520

TATAGTTCAC TCTGTGTTCA TACTTAGTTA TTATACAAAC CATGACTTAA AAGATAAACT 11580

TCAAGATCTG TCAGATGATA GATTGAATAA GTTCTTAACA TGCATAATCA CGTTTGACAA 11640

AAACCCTAAT GCTGAATTCG TAACATTGAT GAGAGATCCT CAAGCTTTAG GGTCTGAGAG 11700

ACAAGCTAAA ATTACTAGCG AAATCAATAG ACTGGCAGTT ACAGAGGTTT TGAGTACAGC 11760

TCCAAACAAA ATATTCTCCA AAAGTGCACA ACATTATACT ACTACAGAGA TAGATCTAAA 11820

TGATATTATG CAAAATATAG AACCTACATA TCCTCATGGG CTAAGAGTTG TTTATGAAAG 11880

TTTACCCTTT TATAAAGCAG AGAAAATAGT AAATCTTATA TCAGGTACAA AATCTATAAC 11940

TAACATACTG GAAAAAACTT CTGCCATAGA CTTAACAGAT ATTGATAGAG CCACTGAGAT 12000

GATGAGGAAA AACATAACTT TGCTTATAAG GATACTTCCA TTGGATTGTA ACAGAGATAA 12060

AAGAGAGATA TTGAGTATGG AAAACCTAAG TATTACTGAA TTAAGCAAAT ATGTTAGGGA 12120

AAGATCTTGG TCTTTATCCA ATATAGTTGG TGTTACATCA CCCAGTATCA TGTATACAAT 12180

GGACATCAAA TATACTACAA GCACTATATC TAGTGGCATA ATTATAGAGA AATATAATGT 12240

TAACAGTTTA ACACGTGGTG AGAGAGGACC CACTAAACCA TGGGTTGGTT CATCTACACA 12300

AGAGAAAAAA ACAATGCCAG TTTATAATAG ACAAGTCTTA ACCAAAAAAC AGAGAGATCA 12360
```

```
AATAGATCTA TTAGCAAAAT TGGATTGGGT GTATGCATCT ATAGATAACA AGGATGAATT   12420

CATGGAAGAA CTCAGCATAG GAACCCTTGG GTTAACATAT GAAAAGGCCA AGAAATTATT   12480

TCCACAATAT TTAAGTGTCA ATTATTTGCA TCGCCTTACA GTCAGTAGTA GACCATGTGA   12540

ATTCCCTGCA TCAATACCAG CTTATAGAAC AACAAATTAT CACTTTGACA CTAGCCCTAT   12600

TAATCGCATA TTAACAGAAA AGTATGGTGA TGAAGATATT GACATAGTAT TCCAAAACTG   12660

TATAAGCTTT GGCCTTAGTT TAATGTCAGT AGTAGAACAA TTTACTAATG TATGTCCTAA   12720

CAGAATTATT CTCATACCTA AGCTTAATGA GATACATTTG ATGAAACCTC CCATATTCAC   12780

AGGTGATGTT GATATTCACA AGTTAAAACA AGTGATACAA AAACAGCATA TGTTTTTACC   12840

AGACAAAATA AGTTTGACTC AATATGTGGA ATTATTCTTA AGTAATAAAA CACTCAAATC   12900

TGGATCTCAT GTTAATTCTA ATTTAATATT GGCACATAAA ATATCTGACT ATTTTCATAA   12960

TACTTACATT TTAAGTACTA ATTTAGCTGG ACATTGGATT CTGATTATAC AACTTATGAA   13020

AGATTCTAAA GGTATTTTTG AAAAGATTG GGGAGAGGGA TATATAACTG ATCATATGTT   13080

TATTAATTTG AAAGTTTTCT TCAATGCTTA TAAGACCTAT CTCTTGTGTT TTCATAAAGG   13140

TTATGGCAAA GCAAAGCTGG AGTGTGATAT GAACACTTCA GATCTTCTAT GTGTATTGGA   13200

ATTAATAGAC AGTAGTTATT GGAAGTCTAT GTCTAAGGTA TTTTTAGAAC AAAAAGTTAT   13260

CAAATACATT CTTAGCCAAG ATGCAAGTTT ACATAGAGTA AAAGGATGTC ATAGCTTCAA   13320

ATTATGGTTT CTTAAACGTC TTAATGTAGC AGAATTCACA GTTTGCCCTT GGGTTGTTAA   13380

CATAGATTAT CATCCAACAC ATATGAAAGC AATATTAACT TATATAGATC TTGTTAGAAT   13440

GGGATTGATA AATATAGATA GAATACACAT TAAAAATAAA CACAAATTCA ATGATGAATT   13500

TTATACTTCT AATCTCTTCT ACATTAATTA TAACTTCTCA GATAATACTC ATCTATTAAC   13560

TAAACATATA AGGATTGCTA ATTCTGAATT AGAAAATAAT TACAACAAAT TATATCATCC   13620

TACACCAGAA ACCCTAGAGA ATATACTAGC CAATCCGATT AAAAGTAATG ACAAAAAGAC   13680

ACTGAATGAC TATTGTATAG GTAAAAATGT TGACTCAATA ATGTTACCAT TGTTATCTAA   13740

TAAGAAGCTT ATTAAATCGT CTGCAATGAT TAGAACCAAT TACAGCAAAC AAGATTGTA    13800

TAATTTATTC CCTATGGTTG TGATTGATAG AATTATAGAT CATTCAGGCA ATACAGCCAA   13860

ATCCAACCAA CTTTACACTA CTACTTCCCA CCAAATATCT TTAGTGCACA ATAGCACATC   13920

ACTTTACTGC ATGCTTCCTT GGCATCATAT TAATAGATTC AATTTTGTAT TTAGTTCTAC   13980

AGGTTGTAAA ATTAGTATAG AGTATATTTT AAAAGATCTT AAAATTAAAG ATCCCAATTG   14040

TATAGCATTC ATAGGTGAAG GAGCAGGGAA TTTATTATTG CGTACAGTAG TGGAACTTCA   14100

TCCTGACATA AGATATATTT ACAGAAGTCT GAAAGATTGC AATGATCATA GTTTACCTAT   14160

TGAGTTTTTA AGGCTGTACA ATGGACATAT CAACATTGAT TATGGTGAAA ATTTGACCAT   14220

TCCTGCTACA GATGCAACCA ACAACATTCA TTGGTCTTAT TTACATATAA AGTTTGCTGA   14280

ACCTATCAGT CTTTTTGTCT GTGATGCCGA ATTGTCTGTA ACAGTCAACT GGAGTAAAAT   14340

TATAATAGAA TGGAGCAAGC ATGTAAGAAA GTGCAAGTAC TGTTCCTCAG TTAATAAATG   14400

TATGTTAATA GTAAAATATC ATGCTCAAGA TGATATTGAT TTCAAATTAG ACAATATAAC   14460

TATATTAAAA ACTTATGTAT GCTTAGGCAG TAAGTTAAAG GGATCGGAGG TTTACTTAGT   14520

CCTTACAATA GGTCCTGCGA ATATATTCCC AGTATTTAAT GTAGTACAAA ATGCTAAATT   14580

GATACTATCA AGAACCAAAA ATTTCATCAT GCCTAAGAAA GCTGATAAAG AGTCTATTGA   14640

TGCAAATATT AAAAGTTTGA TACCCTTTCT TTGTTACCCT ATAACAAAAA AAGGAATTAA   14700

TACTGCATTG TCAAAACTAA AGAGTGTTGT TAGTGGAGAT ATACTATCAT ATTCTATAGC   14760
```

```
TGGACGTAAT GAAGTTTTCA GCAATAAACT TATAAATCAT AAGCATATGA ACATCTTAAA    14820

ATGGTTCAAT CATGTTTTAA ATTTCAGATC AACAGAACTA AACTATAACC ATTTATATAT    14880

GGTAGAATCT ACATATCCTT ACCTAAGTGA ATTGTTAAAC AGCTTGACAA CCAATGAACT    14940

TAAAAAACTG ATTAAAATCA CAGGTAGTCT GTTATACAAC TTTCATAATG AATAATGAAT    15000

AAAGATCTTA TAATAAAAAT TCCCATAGCT ATACACTAAC ACTGTATTCA ATTATAGTTA    15060

TTAAAAATTA AAAATCATAT AATTTTTTAA ATAACTTTTA GTGAACTAAT CCTAAAGTTA    15120

TCATTTTAAT CTTGGAGGAA TAAATTTAAA CCCTAATCTA ATTGGTTTAT ATGTGTATTA    15180

ACTAAATTAC GAGATATTAG TTTTTGACAC TTTTTTTCTC GT                       15222
```

(2) INFORMATION FOR SEQ ID NO:24:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: Oligonucleotide
        (B) LOCATION: 1...47
        (D) OTHER INFORMATION: spA4-antiRSV3'-3'T/(617-663)

(xi) SEQUENCE DESCRIPTION: SEQ ID NO:24:

```
TCTTTGTGGT GTATTATCAT TGTGGGTTGT GTCCATGGTT GGGTTGG                     47
```

(2) INFORMATION FOR SEQ ID NO:25:

(i) SEQUENCE CHARACTERISTICS:
        (A) LENGTH: 55 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: Oligonucleotide
        (B) LOCATION: 1...55
        (D) OTHER INFORMATION: spA4-antiRSV3'-3'T/(718-772)

(xi) SEQUENCE DESCRIPTION: SEQ ID NO:25:

```
CTATGCATTC ATGATTTATC AAGTATATAA ATTTGTGTGT TATGATGTCT CTGGT            55
```

(2) INFORMATION FOR SEQ ID NO:26:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: Oligonucleotide
        (B) LOCATION: 1...41
        (D) OTHER INFORMATION: spA4-antiRSV3'-3'T/(2490-2530)

(xi) SEQUENCE DESCRIPTION: SEQ ID NO:26:

```
ATAGTTGAAT TTGATGTTAT AGGGCTTTCT TTGGTTACTT C                           41
```

(2) INFORMATION FOR SEQ ID NO:27:

(i) SEQUENCE CHARACTERISTICS:

(A) LENGTH: 49 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: Oligonucleotide
        (B) LOCATION: 1...49
        (D) OTHER INFORMATION: spA4-antiRSV3'-3'T/(8251-8299)

(xi) SEQUENCE DESCRIPTION: SEQ ID NO:27:

ATGGTTATTT GGGTTGTTTT GATTGAAATA TAGTGTGTTC TTTTGATTA                49

(2) INFORMATION FOR SEQ ID NO:28:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: Oligonucleotide
        (B) LOCATION: 1...36
        (D) OTHER INFORMATION: spA4-antiRSV3'-3'T/(3212-3247)

(xi) SEQUENCE DESCRIPTION: SEQ ID NO:28:

TTTCCTTTTT TTGTAACTAT ATTATAGATT TTTTCC                              36

(2) INFORMATION FOR SEQ ID NO:29:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: Oligonucleotide
        (B) LOCATION: 1...49
        (D) OTHER INFORMATION: spA4-antiRSV3'-3'T/(8251-8299)

(xi) SEQUENCE DESCRIPTION: SEQ ID NO:29:

TGGTAGTGGT TTTCTTTGCT GGTTTTTTGT TTGGTATTCT TTTGCAGAT                49

RNASE L ACTIVATORS AND ANTISENSE OLIGONUCLEOTIDES EFFECTIVE TO TREAT RSV INFECTIONS

This application claims benefit of U.S. provisional application Ser. No. 60/011,725, filed Feb. 15, 1996.

FIELD OF THE INVENTION

The present invention concerns compounds useful for treating humans infected by Respiratory Syncytial Virus, a negative strand RNA virus, and methods of their use. Particularly, the invention concerns a complex of an oligonucleotide that is complementary to some portion of the anti-genomic strand of RSV and a covalently linked activator of RNase L (henceforth, "activator-antisense complexes"). More particularly, the invention concerns activator-antisense complexes, in which the oligonucleotide is selected to bind to a portion of the RSV anti-genomic strand that normally has no self-hybridizing secondary structure.

BACKGROUND TO THE INVENTION

Respiratory syncytial virus (RSV), a non-segmented, negative-strand RNA virus in the pneumovirus subfamily of Paramyxoviridae, is a widespread human pathogen accounting for over 1 million deaths per year worldwide (McIntosh and Chanock 1990). While the majority of serious cases are children from developing countries, there are estimated to be 300,000 hospitalized cases per year in the United States (Zisson, 1993). It is also believed that of childhood deaths from pneumonia caused by respiratory viral infections, 62% are due to RSV (Heilman, 1994). The only approved treatment for RSV is aerosolized ribavirin (1-b-D-ribofuranosyl-1,2,3-triazole-3-carboxamide). Ribavirin is administered as an aerosol which is inhaled. Ribavirin therapy has several limitations including minimal efficacy in clinical use, the requirement of a tent around the patient, the potential to clog ventilating units, and the observation of some teratogenicity in animal models (Froelich, 1994), significant side effects and high cost.

RSV replicates in several alveolar cell types including macrophage and epithelial lineages (Panuska et al., 1992, Midulla et al., 1993). Accordingly, ribavirin is administered to RSV infected individuals by inhalation of an aerosol. Taber et al., 1983, Pediatrics 72:613–18; Hall et al., 1983, N. Eng. J. Med. 308:1443–7; Englund et al., 1994, J. Pediatrics 125:635–41.

Activator-antisense complexes (termed therein "2-5A:AS") have been described previously (Torrence et al., 1993, WO 94/09129 by Torrence et al.). Although antisense oligonucleotides have been used as antiviral agents, e.g.: to inhibit HIV replication, see Zamecnik et al, 1986; Goodchild et al., 1988; Letsinger et al., 1989; Balotta et al., 1993; to inhibit RSV infection, WO95/22553 by Kilkuskie et al., no examples of the successful use of activator-antisense complexes as an antiviral therapy have been reported.

The mechanism of action of activator-antisense complexes is different than the mechanism of action of other antisense oligonucleotides. The activator portion of the activator-antisense complexes activates RNase L and the antisense domain serves as a specific, high affinity binding site for the target RNA. The result is the selective cleavage of the target RNA by RNase L.

Physiologically, RNase L functions as part of the interferon system in restricting virus replication in cells of higher vertebrates (reviewed in Silverman, 1994). Interferon treatment of cells activates genes encoding 2-5A synthetases, double-stranded RNA (dsRNA)-dependent enzymes that produce 5'-triphosphorylated, 2',5'-linked oligoadenylates (2',5'A) from ATP. Viral dsRNAs are potential activators of these enzymes (Gribaudo et al., 1991). The 2',5'A binds to and activates RNase L resulting in the general cleavage of cellular and viral RNA; thus restricting the replication of some picornaviruses (Chebath et al., 1987; Rysiecki et al., 1989; and Hassel et al., 1994).

RNase L is not specific for cleaving viral RNA. For instance, in interferon-treated, encephalomyocarditis virus infected cells, RNase L causes degradation of ribosomal RNA (Wreschner et al., 1981). Through the activator-antisense approach, RNase L is converted from a non-specific nuclease to a highly specific endoribonuclease that selectively cleaves mRNA targets. This has been demonstrated in a cell-free system from Daudi cells, a human lymphoblastoid cell line, in which a modified HIV-1 vif mRNA was targeted for cleavage by an activator-antisense complex (Torrence et al., 1993). Subsequently, purified RNase L has been directed by an activator-antisense complex to cleave selectively an mRNA target encoding the protein kinase PKR in the presence of a nontargeted mRNA (Maran et al., 1994). Furthermore, in HeLa cells, the use of activator-antisense complexes, which were directed to a sequence in PKR mRNA, resulted in the ablation of PKR mRNA and enzyme activity (Maran et al., 1994) such that the dsRNA-mediated activation of transcription factor, NF-kB was ablated. More recently, it was shown that the activation of RNase L by an activator-antisense complex results in the catalytic degradation of PKR mRNA ($k_{cat}$, of about 7 $sec^{-1}$) (Maitra et al., 1995).

SUMMARY OF THE INVENTION

The present invention provides a complex that is useful for the treatment of infection by RSV. The essential components of the complex are an antisense oligonucleotide which has a sequence that is complementary to between about 10 and about 30 nucleotides of the antigenomic RNA strand, i.e., the template strand for genome synthesis, of a strain of RSV and an activator of RNase L (henceforth, "activator-antisense complexes"). The elements of the activator-antisense complex are preferably covalently linked by a linker.

In an alternative embodiment, the invention consists of a non-covalently linked complex comprising one or two activated RNase L molecules and at least one antisense oligonucleotide complementary to between about 10 and 30 nucleotides of the antigenomic RNA strand of RSV (henceforth, "enzyme-antisense complexes"). In a further alternative embodiment the invention consists of an antisense oligonucleotide having a sequence of at least 10–30 nucleotides and preferably 15–25 nucleotides, and more preferably which is 18 or 19 nucleotides.

The activator-antisense complexes of the invention are transported across the cell membrane without the use of carriers or permeabilizing agents. Once internalized the activator-antisense complexes lead to the formation of enzyme-antisense complexes, which causes destruction of the antisense targeted RNA. To treat RSV infection the antisense complexes can be administered by inhalation of an aerosol, the same method as is used to administer ribavirin. Ribavirin and the antisense complexes of the invention can, therefore, be administered in a common pharmaceutical composition.

BRIEF DESCRIPTION OF THE FIGURES

FIGS. 1A–1J. The sequence of Respiratory Syncytial Virus strain A2, positions numbered in the 5'→3' direction (SEQ ID NO:23.

DETAILED DESCRIPTION OF THE INVENTION

Figure 2:
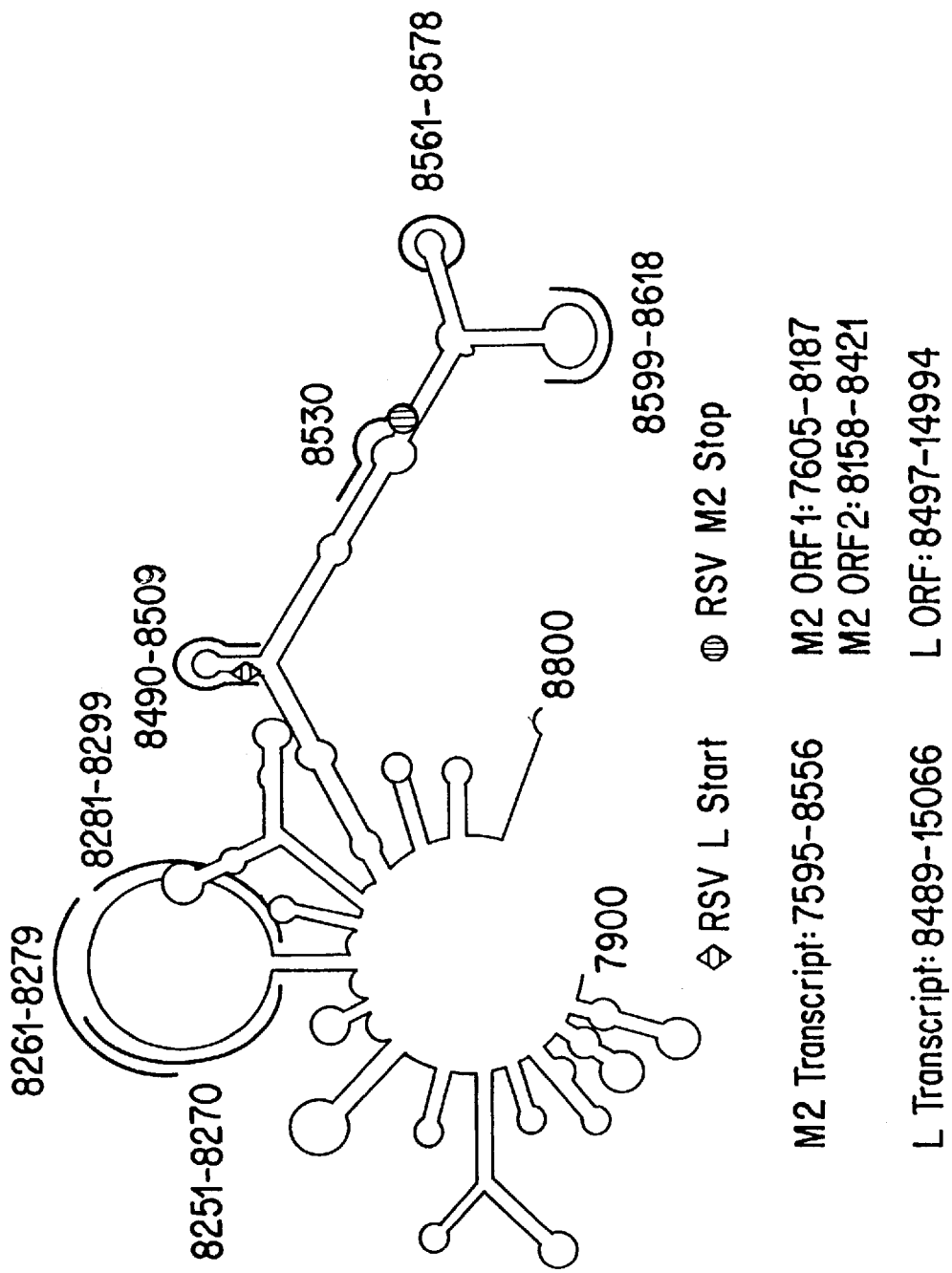
FIG. 2. Squiggle plot output of MFOLD calculations of the secondary structure of portions of the RSV antigenomic RNA, positions numbered in 5'→3' order. Squiggle plot of residues 7900–8800 of RSV antigenomic RNA.

The invention in one embodiment consists of the covalently-linked complex of an activator of RNase L and an oligonucleotide that is capable of binding to the antigenomic template RNA strand of RSV and/or binding to an mRNA of an RSV protein (an "RSV antisense oligonucleotide"). In an alternative embodiment the invention consists of the non-covalently linked complex of an activated RNase L and an RSV antisense oligonucleotide.

In a preferred embodiment the antisense oligonucleotide is complementary to a portion of the RSV antigenome that is normally single stranded. The activator is attached through a linker to either the 3' or the 5' terminus of the antisense oligonucleotide by a linker. In one embodiment, a blocker is attached to the 3' terminus of antisense oligonucleotide and the linker is attached to the 5' terminus of the antisense oligonucleotide. In an alternative embodiment the linker is attached to the 3' end of the antisense oligonucleotide and serves as both linker and blocker. The antisense oligonucleotide is between about 15 and about 20 nucleotides in length and preferably 18 or 19 nucleotides in length. Those skilled in the art will understand that oligonucleotides with high GC content can be shorter than those with low GC content.

According to the invention, the portion of the antigenome of a strain of RSV to which the antisense oligonucleotide is complementary can be determined from the sequence of the strain of RSV and secondary structure determining algorithms such as MFOLD. A suitable portion of the RSV antigenome is one that is normally in a single stranded conformation, e.g., forms a loop of the stem and loop secondary structure of RNA.

Because RSV is a negative strand virus, the antisense oligonucleotides are complementary not only to the antigenomic RNA but also to the MRNA that directs translation of the viral proteins.

The internucleotide phosphodiester bonds of the antisense oligonucleotide can be any bonds that are compatible with the formation of Watson-Crick base pairs with complementary RNA. These include as non-limiting examples phosphodiesters, phosphorothiodiesters, methylphosphonodiesters and methylphosphonothiodiesters, which provide for increased resistance to degradation after administration. The nucleotides of the antisense oligonucleotide can be 2'-deoxynucleotides or 2'O-methyl nucleotides.

DETERMINATION OF THE SEQUENCE OF THE ANTI-SENSE OLIGONUCLEOTIDE

The sequence of RSV strain A is given in FIGS. 1:1–1:10, in the 5'→3' orientation. The present invention is exemplified by oligonucleotides directed towards strain A2, but the invention can be practiced with any other strain of RSV, having a known genomic sequence. The sequence of the RSV antigenome RNA can be derived therefrom by routine techniques. RSV is a negative strand RNA virus having multiple genes, i.e., the virion contains the complement of the coding strand. On entry into a host cell the genome is transcribed to produce the various mRNA encoding the viral proteins and also to produce an entire complementary RNA, the RSV antigenome, from which the genomic strands of the progeny virus are transcribed. According to the invention the sequence of the antisense oligonucleotide is selected so that the activator-antisense complex binds to and thereby causes the catalytic destruction of the RSV antigenome or alternatively an mRNA. As used herein the terms "antigenomic strand," "RSV antigenome" and "RSV mRNA" are synonyms.

Thus, in an embodiment of the invention the sequence of the antisense oligonucleotide of the invention is selected so that the antisense oligonucleotide is complementary to a portion of the RSV antigenome and will bind to it, i.e., the activator-antisense complex targets activated RNase L to the portion of the RSV antigenome complementary to the antisense oligonucleotide. Single stranded RNA molecules have regions in which the polymer "folds back" by self hybridizing. These regions of self hybridizing duplex RNA ("stems") are separated by single-stranded "loops" and "bubbles." Thus, not all portions of the RSV antigenome are susceptible to binding to the antisense oligonucleotide with equal affinity and, thus, not all portions of the RSV antigenome are suitable as targets of the activator-antisense complexes.

Which portions of an RNA molecule are in stems and which are in loops or bubbles for the purposes of the invention is determined by a computer modeling program such as "FoldRNA" or "MFOLD", which are in the public domain (e.g., through the Biocomputing Office, Biology Department, Indiana University, Bloomington, Ind.). Such programs systematically assess all possible conformations and determine the conformation that is the most thermodynamically favored, i.e., has the lowest "free energy." Routinely, conformations that have a free energy within 5% or 10% of the optimal conformation are also determined. Most often these nearly optimal conformations are closely related to each other, for example the position of a small bubble can differ by one or two nucleotides. As used herein a RNA strand is said to be "normally single stranded" when it is single stranded in the conformation having the lowest free energy or a free energy equivalent to the lowest free energy.

The algorithm that is implemented by these programs is described in Zuker et al., 1989, SCIENCE 244:48. The number of steps needed to calculate the lowest free energy state of a polynucleotide, according to the algorithm of Zuker is proportional to the cube of length of the polynucleotide. At present, conformations of 2 KB polynucleotides can be routinely calculated while the calculations of polynucleotides that are the length of the entire RSV antigenome ($\approx$5 KB) are burdensome.

However, because of the kinetics of the intramolecular hybridization of polynucleotides, it is unlikely that conformations involving hybridization between widely separated portions of the polynucleotide do in fact occur even if the modeling programs indicate that they would yield a lower free energy state. Thus, no practical purpose is served by calculating the thermodynamically most stable conformation of the entire RSV antigenome. Rather, for the purposes of the invention, the conformation of the RSV antigenome can be calculated using fragments that are about 1–2 KB in length. If the predicted conformation of a particular portion of the RSV antigenome is dependent upon the length or the boundaries of the nucleotide fragment that is modeled, then the modeling program of the shorter fragment, greater than 1 KB in length, and the fragment wherein the portion is located closest to the middle of the fragment is considered to be the "normally" occurring conformation.

There are several major considerations in selecting which portions of the antisense genome are suitable as targets.

1. Since the RNase L is active only on single-stranded sequences and not on double-stranded sequences, it is important that there be significant stretches of non-base-paired or minimally base-paired nucleotides near the chosen RNA target sequence.

2. Since the RNase L prefers cleavage after UNp sequences, it is preferred that the single-stranded region where cleavage may occur should contain uridine. This is preferred but not essential as it has been shown that the activator-antisense complex can direct cleavage to other nucleotides. Maran et al., 1994.

3. Since cleavage occurs on the 5'-side of the RNA target sequence, it is preferred that such uridine-containing single-stranded regions should be on the 5'-side of the target sequence.

4. Since the antisense domain of the activator-antisense complex must form a double-helical complex with an RNA target sequence, it is preferable that such a targeted sequence be located in a single-stranded or predominantly singly-stranded region of the target RNA. This is due to the consideration that such complex formation is an equilibrium process, and the magnitude of association constant for the process is reduced according to the degree and stability of secondary structure within the specific target sequence.

5. For the reasons expressed in (4) above, Zuker's MFOLD algorithm is used to generate a group of plausible RNA secondary structures. A set of structures can be generated using this program which differ only slightly in energy. Typically the folding program generates secondary structures differing in increments of 0.1 Kcal/mol, and are therefore are energetically very similar.

6. Consideration of (1–5) above leads to a search for the most preferred target sequence in an RNA target. This target ideally should be single-stranded throughout the entire sequence that serves as the antisense binding site as well as a region upstream on the RNA of at least 16 and preferable at least 21 nucleotides. Thus in the ideal situation the preferred target site should be the length of the antisense domain (e.g., 18) plus 16 equals 34 nucleotide in length. Thus, a search would be made for regions in a potential target RNA for single-stranded regions at least 34 nucleotides long and more preferably at least 45 nucleotides long.

7. One additional preference in the design of the activator-antisense complex relates to the composition of the antisense oligonucleotide. Because the activator-antisense complex operates catalytically, there must exist a necessary mechanism for the dissociation of the complex from its complementary sequence in the target RNA. Thus, it is to be expected that duplexes with a large fraction of GC base pairs would undergo dissociation with more difficulty than those having a large fraction dA-rU or dT-rA pairings. This consideration would also be a preferred design consideration.

FIG. 2A shows the results of the modeling of residues 7900–8800 of the mRNA or antigenomic strand. FIG. 2A also contains indications of the locations of the antisense oligonucleotides that were tested in the Examples below. FIGS. 2B:1–2H:3 show alternative results of modeling residues segments of the RSV antisgenome from 1 to 7999, 1100 to 2400 and 2200 to 3300, respectively. Two or three different models of each region, with virtually equivalent energies, are shown. These plots indicate, for example, that preferred embodiments the invention target residues 2490–2530, which is single stranded in all three models, residues 617–663, 3212–3247 and 5240–5288 which are single stranded in at least two of the models shown, and residues 718–772, which is single stranded in one of the three models. It must be remembered that the entire family of generated models differ only by 1.1 kcal/mol, and, therefore, each model represents conformations that can be assumed by the RSV antigenome.

THE STRUCTURE OF THE ACTIVATOR

Examples of the structure of the activator are described in patent publication WO94/09129, at pages 10, 45 and 46–51, which is hereby incorporated by reference. Briefly, the activator can contain at least three riboadenylate residues, linked by 2'-5'phosphodiester bonds, having a free 5' mono-, di- or triphosphate or thiophosphate. The 5' thiophosphate-tetra-adenylate activator (sp5'A2'(p5'A2')$_3$—O—) is the preferred activator. Other activators include p5'A2'(p5'A2')$_2$—O—, sp5'A2'(p5'A2')$_2$—O—, and p5'A2'(p5'A2')$_3$—O—.

Phosphorothioate and phosphorodithioate linkages between adenine nucleosides can be used as well as phosphodiester. The use of these linkages results in decreased degradation but also decreased activity. Beigelmann, L., et al., 1995, Nucleic Acid Research 23:3989–94. The use of a 5'-thiophosphate results in greatly improved activity and stability. Those skilled in the art appreciate that other nucleotides can be attached to the 3'hydroxyl or 2'hydroxyl of the 2'-5'tri- or tetra-adenylate without changing its activity as an RNase L activator. Thus, these embodiments are also included in the scope of the term "activator of RNase L." Those skilled in the art will further recognize that oligonucleotides containing bases other than adenine, such as inosine at the second nucleotide (counting 5'→3') can also be used. Those skilled in the art also recognize that non-nucleotide activators of RNase L can be used in the invention and are equivalents of nucleotide activators. As used herein the term "2-5A" refers to any nucleotide activator of RNase L and the term "activator of RNase L" refers to any activator of RNase L including 2-5A. The term 2',5'A refers specifically to 2',5'-linked oligoadenylates.

THE STRUCTURE OF THE ANTISENSE OLIGONUCLEOTIDES

The antisense oligonucleotide can have any structure now known or to be developed in the antisense art. These include phosphodiesters, phosphorothiodiesters, methylphosphonodiesters and methylphosphonothiodiesters, which provide for increased resistance to degradation after administration. The nucleotides of the antisense oligonucleotide can be 2'-deoxynucleotides or 2'O-methyl nucleotides.

The preparation of modified and unmodified oligonucleotides is well known in the art (reviewed in Agrawal et al. (1992) Trends Biotechnol. 10:152–158; Agrawal in Protocols for Oligonucleotides and Analogs, Synthesis and Properties (Agrawal, ed.), Humana Press, Totowa, N.J. (1993), Chapter 20). For example, nucleotides can be covalently linked using art-recognized techniques such as phosphoramidate, H-phosphonate chemistry, or methylphosphoramidate chemistry (see, e.g., Uhlmann et al. (1990) Chem. Rev. 90:543–584; Agrawal et al. (1987) Tetrahedron. Lett. 28:(31):3539–3542); Caruthers et al. (1987) Meth. Enzymol. 154:287–313; U.S. Pat. No. 5,149,798). Oligomeric phosphorothioate analogs can be prepared using methods well known in the field such as methoxyphosphoramidite (see, e.g., Agrawal et al. (1988) Proc. Natl. Acad. Sci. (USA) 85:7079–7083) or H-phosphonate (see, e.g., Froehler (1986) Tetrahedron Lett. 27:5575–5578) chemistry. The synthetic methods described in Bergot et al. (J. Chromatog. (1992) 559:35–42) can also be used.

THE STRUCTURE OF THE LINKER

Any linker that covalently connects an activator of RNase L and the antisense oligonucleotide and does not prevent the activator from activating RNase L can used. In a preferred embodiment the linker is attached to the 3' or 2' terminus of a 2-5A activator. In a further preferred embodiment the linker consists of a bis-1,4-butanediol-phosphodiester which connects the 3' or 2' terminus of a 2-5A activator and the 5' or the 3' terminus of the antisense oligonucleotide. Attachment to a terminus of the antisense oligonucleotide is selected for the convenience of synthesis. Those skilled in the art appreciate that attachment to an internal 2' hydroxyl or to a portion of the nucleotide base that is not critical to base pairing are alternative embodiments of the invention.

USE OF THE ACTIVATOR-ANTISENSE COMPLEXES

The activator-antisense complexes of the invention can be administered to a subject having an RSV infection by any route effective to deliver the activator-antisense complexes to the epithelium of the bronchi, bronchioles and alveoli of the subject. In one embodiment the activator-antisense complexes are delivered by use of an inhaled aerosol, according to the techniques well known in the art for the delivery of ribavirin. In a further embodiment of the invention a mixture of ribavirin and an activator-antisense complex of the invention can be administered in a common pharmaceutical carrier.

In an alternative embodiment the activator-antisense complex can be administered parenterally, e.g., by intravenous infusion. When delivered by intravenous administration, the dose of activator-antisense complex can be determined by routine methods well known to pharmacologists so that the serum concentration approximates the concentration at which antiviral activity is seen in the in vitro examples described below, e.g., a concentration of about 10 $\mu$M of spA$_4$-antiRSV3'-3'T/(8281–8299). When delivered by aerosol administration the dose should be selected so that the tissue concentration in the lung approximates the concentration at which antiviral activity is seen in the in vitro examples.

EXAMPLES

MATERIALS AND METHODS

Sequence conventions. The practice of the RSV literature, position 1 of the RSV genome (the virion RNA) is the 3' terminus; position 1 of the RSV antigenome (mRNA) is the 5' terminus. Thus, for example, the antisense oligonucleotide labeled antiRSV/(8490–8509) has the sequence (5'→3') of residues 8509 to 8490 of the RSV genome and is complementary to residues 8490–8509 of the RSV antigenome. Note, however, that the RSV strain A2 genome sequence of FIGS. 1:1–1:10 is in conventional 5' to 3' order. Hereinafter activator-antisense complexes wherein the activator is a 2',5'A are termed "2-5A antisense chimeras."

Synthesis and Purification of 2-5A Antisense Chimeras.

Oligonucleotide Structural Types Synthesized. The following generic oligonucleotide types were prepared for this study.

I. p5'A2'p(5'A2'p)$_3$—[O(CH$_2$)$_4$Op]2-5'dB3'p(5'dN3'p)$_n$5'dN

II. A2'p(5'A2'p)$_3$—[O(CH2)$_4$Op]$_2$—5'dN3'p(5'dN3'p)$_n$5'dN

III. dN3'p(5'dN3'p)$_n$5'dN

IV. p5'A2'p(5'A2'p)$_3$—[O(CH$_2$)$_4$Op]$_2$—5'dN3'p(5'dN3'p)$_m$5'dN3'p-3'pdN5'

V. sp5'A2'p(5'A2'p)$_3$—[O(CH$_2$)$_4$Op]$_2$-5'dN3'p(5'dN3'p)$_m$5'dN3'p-3'pdN5'

VI. A2'p(5'A2'p)$_3$—[O(CH$_2$)$_4$Op]$_2$-5'dN3'p(5'dN3'p)$_m$5'dN3'p-3'pdN5'

VII. sp5'A2'p(5'A2'p)$_3$—[O(CH$_2$)$_4$Op]$_2$-5'dN3'p(5'dN3'p)$_n$5'dN

VIII. p5'A2'p(5'A2'p)$_3$—[O(CH$_2$)$_4$Op]$_2$-3'dN5'(p3'dN5')$_n$p3'dN

The following procedures are illustrative of those employed to synthesize the 2-5A-antisense chimeric oligonucleotides in classes I–VIII above. In general, they follow the synthetic strategy developed in Lesiak et al., 1993.

Reagents and Chemicals Employed.

1. For initiation of synthesis on solid support:

dA-3'-lcaa-CPG (500 Å)
5'-O-dimethoxytrityl-N6-benzoyl-2'-deoxyadenosine-3'-lcaa-CPG
dC-3' lcaa-CPG (500 Å)
5'-O-dimethoxytrityl-N4-benzoyl-2'-deoxycytidine-3'-lcaa-CPG
dG-3' lcaa-CPG (500 Å)
5'-O-dimethoxytrityl-N2-isobutyryl-2'-deoxyguanosine-3'-lcaa-CPG
dT-3'-lcaa-CPG (500 Å)
5'-O-dimethoxytritylthymidine-3'-lcaa-CPG These solid supports were used to synthesize oligonucleotides with the normal 3'→5' phosphodiester bonds. All were 1 μmole size. These DMT protected nucleosides are attached to controlled pore glass (CPG) through a succinyl group and a long chain alkyl amine (lcaa) linker are commercially available products of Applied Biosystems (Foster City, Calif.). These supports were employed in the synthesis of generic oligonucleotide types I, II, III, and VII.

dA-5'-lcaa-CPG (500 Å)
3'-O-dimethoxytrityl-N6-benzoyl-2'-deoxyadenosine-5'-lcaa-CPG
dC-5' lcaa-CPG (500 Å)
3'-O-dimethoxytrityl-N4-benzoyl-2'-deoxycytidine-5'-lcaa-CPG
dG-5' lcaa-CPG (500 Å)
3'-O-dimethoxytrityl-N2-isobutyryl-2'-deoxyguanosine-5'-lcaa-CPG
dT-5'-lcaa-CPG (500 Å)
3'-O-dimethoxytritylthymidine-5'-lcaa-CPG These solid supports were obtained form Glen Research (Sterling, Va.) and were used to synthesize oligonucleotides with the reversed polarity 5'→3' phosphodiester bonds. All were 1 μmole size. These supports were employed for the synthesis of generic oligonucleotide types IV, V, VI, and VIII.

2. Elongation of the DNA antisense chain.

For normal 3'→5' phosphodiester bond oligonucleotides, a total of 500 mg of each of the following phosphoramidites (Applied Biosystems) was dissolved in the indicated amount of anhydrous acetonitrile to make a 0.1 M phosphoramidite solution:

5'-O-dimethoxytrityl-N6-benzoyl-2'-deoxyadenosine-3'-(2-cyanoethyl-N,N-diisopropyl)phosphoramidite (5.6 mL)
5'-O-dimethoxytrityl-N4-benzoyl-2'-deoxycytidine-3'(2-cyanoethyl-N,N-diisopropyl)phosphoramidite (5.9 mL)
5'-O-dimethoxytrityl-N2-isobutyryl-2'-deoxyguanosine-3'-(2-cyanoethyl-N,N-diisopropyl)phosphoramidite (5.8 mL)
5'-O-dimethoxytrityl-2'-deoxythymidine-3'-(2-cyanoethyl-N,N-diisopropyl)phosphoramidite (6.6 mL)

The foregoing were used in the preparation of generic oligonucleotide types I, II, III, IV, V, VI, and VII.

For the synthesis of oligonucleotides with all DNA phosphodiester bonds with reversed polarity, the following phosphoramidites were obtained from Glen Research (Sterling, Va.).

3'-O-dimethoxytrityl-N6-benzoyl-2'-deoxyadenosine-5'-(2-cyanoethyl-N,N-diisopropyl)phosphoramidite (5.6 mL)
3'-O-dimethoxytrityl-N4-benzoyl-2'-deoxycytidine-5'(2-cyanoethyl-N,N-diisopropyl)phosphoramidite (5.9 mL)
3'-O-dimethoxytrityl-N2-isobutyryl-2'-deoxyguanosine-5'-(2-cyanoethyl-N,N-diisopropyl)phosphoramidite (5.8 mL)
3'-O-dimethoxytrityl-2'-deoxythymidine-5'-(2-cyanoethyl-N,N-diisopropyl)phosphoramidite (6.6 mL)

The above intermediates were employed to synthesize generic oligonucleotide type VIII.

3. Linker to join chimeric domains.

The linker, (2-cyanoethyl-N,N-diisopropyl)—[4-O-(4,4'-dimethoxytrityl) butyl]phosphoramidite, was synthesized by a modification of an earlier described procedure (Lesiak et al., 1993), and a 0.1 M solution was made by dissolving 100 mg linker in 1.7 mL of anhydrous acetonitrile.

4. For synthesis of 2',5'-oligoadenylate domain of the chimera.

5'-O-dimethoxytrityl-N6-benzoyl-3'-O-t-butyldimethylsilyladenosine-2'-N,N-diisopropylcyanoethylphosphoramidite (ChemGenes Corp., Waltham, Mass., cat no. ANP 5681). A 0.1 M solution was made by dissolving 500 mg of monomer in 5.0 mL of anhydrous acetonitrile.

5. Phosphorylation Reagent for 5'-terminus of 2',5'-oligoadenylate domain of chimera.

2-[2-(4,4'-dimethoxytrityl)ethylsulfonyl]ethyl-(2-cyanoethyl)-(N,N-diisopropyl)-phosphoramidite (Glen Research, Sterling, Va. cat no. 10-1900-90) was used at a concentration of 0.2 M in anhydrous tetrazole/acetonitrile (ABI) for semi-automated synthesis.

6. Other Reagents.

All other DNA synthesis reagents were obtained from Applied Biosystems Inc. which includes diluent (acetonitrile), activator solution (tetrazole/acetonitrile), capping solutions (A: acetic anhydride solution and B: N-methylimidazole solution), deblocking reagent (trichloroacetic acid solution), oxidizer (iodine solution), and tetraethylthiuram disulfide sulfurization reagent.

Tetrabutylammonium fluoride in tetrahyrofuran (Aldrich, Milwaukee, Wis.) was used to deblock the t-butyldimethylsilyl group used for protection of the 3'-hydroxyls of (2',5')-oligoriboadenylate domain.

SYNTHESIS PROCEDURE

The 2',5'-oligoadenylate/antisense chimeras were synthesized by modified automated or semi-automated procedure.

All of the chemicals were dried over $P_2O_5$ in vauco overnight before use. The 1 μmole deoxynucleoside-lcaa-CPG column was used.

The core (2',5')-oligoadenylate/antisense chimera refers to the complete 2',5'A-antisense chimera minus the 5'-terminal monophosphate group and has three regions defined for synthetic purposes: an antisense region, a linker region, and (2',5')-oligoadenylate region. The 2',5'A-antisense chimera was synthesized by the automated method listed in Table 1.

1 μmole scale standard synthesis cycle was used. The cycle was modified by changing the coupling time (coupling of monomer) for each different region. The monomer/acetonitrile solution was installed on the DNA synthesizer by a double change procedure to avoid contaminants. After the synthesis of each region, the column was dried completely by Argon for at least 3 min. and the synthesis cycle, trityl mode, and sequence were edited for the synthesis of next region of the desired oligonucleotide.

For preparation of core 2',5'A-antisense chimeras without a 5'-monophosphate group, the final step was omitted in Table 1. For semi-automated preparation of the 5'-monophosphate terminating chimeras, the core oligonucleotide was synthesized with the trityl group on, and the column was dried and removed from the DNA synthesizer. The 5'-end phosphorylation was performed manually according to the procedure presented in Table 2.

Cleavage and Deprotection

1. The oligonucleotide was cleaved from the CPG support by concentrated ammonium hydroxide/ethanol (3:1 v/v) at room temperature for 2 hours.

2. The ammonium hydroxide/ethanol solution of crude oligonucleotide was removed into a 3 mL vial and sealed tightly. The solution was incubated at 55° C. for 8 hours to remove the protecting groups on the bases.

3. The resulting ammonium hydroxide/ethanol solution of oligonucleotide was transferred to a glass tube, and cooled completely in a ice-bath. The solution was then evaporated to dryness in a speedvac concentrator and a solution of tetrabutylammonium fluoride (2 mL, 1.0 M) in THF was added, and the entire mixture was vortexed for at least 1 min. This reaction mixture was allowed to incubate at room temperature for at least 10 hours.

An equivalent volume of 0.1 M TEAA (tetraethylammonium acetate) (pH 7.0) buffer was added, mixed and evaporated to half volume to remove THF. The residue was subjected to purification by HPLC.

Purification of the oligonucleotides

1. Polystyrene Reverse-Phase Ion-Pair Chromatography (PRP-IPC) Protocol (a modification of the method of Swiderski, et al., 1994).

The oligonucleotide was dissolved in about 4–5 mL water to make a clear solution (centrifuged if necessary), and the clear solution was directly injected into the PRP-1 HPLC column (300×7 mm). The reaction mixture was thus simultaneously desalted and purified.

Solvent A: 10 mM tetrabutyl ammonium phosphate (TBAP), pH 7.5 in water.
Solvent B: 10 mM TBAP, pH 7.5 in acetonitrile/water (8:2 v/v).

The sample was eluted with a convex gradient of 5–90% solvent B in A in 60 min. at a flow rate of 1.5 mL/min.

Fractions containing desired oligo were pooled and evaporated to about 1–2 mL. The oligo-TBA ion-pair was converted into its sodium salt form by the following procedure:

1 mL of Dowex 50W ion exchange wet resin (Na$^+$ form) was added into oligonucleotide/water solution. The solution was stirred for at least 30 min. in the cold room. The resin was removed by passing the solution through a Poly-Prep chromatography column (Bio-Rad, Cat. #731-1550). The resin was washed with extra water until no oligonucleotide remained on the resin.

Alternately, prior to Dowex treatment the oligonucleotide was passed through a C-18 Sep-Pak cartridge according to the following procedure.

a. The C-18 cartridge was pre-washed with 10 mL methanol and 10 mL water.
b. The oligo solution was loaded onto the cartridge.
c. The cartridge was washed with 20 mL water to remove salt from the column.
d. The oligonucleotide was eluted with 10 mL of 50% methanol in water.
e. The desalted oligonucleotide was detected by UV spectrophotometer and the fractions containing oligo were combined and concentrated.

Dialysis of (2',5')-Oligoadenylate/antisense Chimeras

After Purification by HPLC and ion exchange, the oligonucleotide (sodium salt) was dialyzed to remove small molecules and excess salt. The dialysis was carried out at 4° C. The oligonucleotide was dialyzed against 0.02 M NaCl first for 4–6 hours and then against water for 48 hours. If the oligonucleotide was desalted on C-18 sep-pak cartridges after HPLC purification, the time of dialysis can be shortened to 6–10 hours.

Post-treatment of Oligoadenylate/antisense Chimeras

The oligonucleotide, after dialysis, was passed through a 0.22$\mu$ millex-GV filter unit (Millipore, Cat. No. SLGV025LS) for sterilization. The resulting solution was quantitated as O.D. A260 by UV/Vis spectrophotometry.

Nucleotide composition analysis of (2',5')-oligoadenylate/antisense Chimeras

1. Nucleotide Composition Analysis

The nucleotide composition of the chimeric oligonucleotide were analyzed by enzymatic digestion with snake venom phosphodiesterase (*Crotallus durissus*) (Pharmacia, cat #27,0821-01).

A purified oligonucleotide (0.2 A260 O.D.U.) is incubated with snake venom phosphodiesterase (0.15 units) in 50 mM Tris/HCl, pH 8.0, 0.5 mM MgCl$_2$, pH 8.0. The 100 $\mu$L mixture was incubated at 37° C. for at least 3 hours. For chimeric oligonucleotides containing a 3'-3'dN, such as Oligonucleotide Structural Type IV (section 6), the incubation time was extended to 10 hours.

After digestion, the solution was treated with Microcon-10 (Amicon, Inc. product No. 42406). The microcon was first spin-rinsed with water before addition of 100 $\mu$L sample solution. The centrifuge time was typically 45 min. The clear solution was used for HPLC analysis.

An aliquot (5–10 $\mu$L) of the hydrolysate was analyzed by reverse phase HPLC using a Beckman Ultrasphere C-18 ODS column (0.46×25 cm). Separation of the digestion products was accomplished under the following conditions: 2% B isocratically for 20 min. linear gradient 2–50% B for 15 min. and held isocratically 10 min where solvent A was 100 mM ammonium phosphate, pH 5.5 and solvent B was methanol/water (1:1 v/v). The flow rate was 0.5 mL/min. The standard markers dCMP, TMP, dGMP, AMP and dAMP (Aldrich Chem. Co.) were used to compare retention times and elution orders of the hydrolysis products. Typically, the peaks obtained from the enzymatic hydrolysis of an oligonucleotide had retention times of 9.7 min. (dCMP), 27.3 min. (TMP), 29.6 min. (dGMP), 31.7 min. (AMP), 39.5 min. (Alinker) and 41.2 min. (dAMP). The retention times varied depending on the column, pH value of mobile phase and the equilibrium times of the column. The integrated peak areas provided the relative content of each nucleotide. The extinction coefficients of 7610 (dCMP), 8158 (TMP), 9969

(dGMP), 12342 (AMP & Alinker), 14361 (dAMP) measured at 260 nm in 100 mM ammonium phosphate, pH 5.5 were used in the analysis.

Oligonucleotide Purity Confirmation

The purities of (2',5')-oligoadenylate/antisense chimeras were checked by HPLC or gel capillary electrophoresis (GCE). The purity was obtained by the integration of peak area detected at 260 nm.

1. Gel Capillary Electrophoresis (GCE) Method

The measurement of oligonucleotide purity was performed on an Applied Biosystems 270A-HT capillary electrophoresis instrument using MICRO-GEL100 (Applied Biosystems Inc.) gel filled capillaries (50 uM i.d., effective length 27 cm, running buffer, 75 mM Tris phosphate (pH 7.6), 10% methanol). Detection was at 260 nm. A typical electrophoregram of (2',5')-oligoadenylate/antisense chimera was obtained by the following conditions: sample concentration was approx. 0.1 O.D./mL, electrokinetic injection was 2 s at −5kv. Voltage was −14 mA (19 mA) and the operation temperature was 30° C. Under this condition, the (2',5')-oligoadenylate/antisense chimera had about 1 min. earlier elution time than that of its core analogue.

2. Dionex PA-100 Ion Exchange HPLC Method

The purities of oligonucleotides could also be measured by a Dionex Ion exchange HPLC. Usually, the dionex PA-100 ion exchange column could provided higher resolution and better peak shape compared with other HPLC chromatographic method for the analysis of (2',5')-oligoadenylate/antisense chimera.

A typical chromatogram of (2',5')-oligoadenylate/antisense was obtained by the following conditions: Dionex PA-100 (4×250 mm) column (Dionex, cat #43010). Solvent A was 25 mM Tris/HCl and 0.5% acetonitrile (pH 7.0), solvent B was 25 mM Tris/HCl, 0.5% acetonitrile and 1 M ammonium chloride (pH 7.0). The sample was eluted in linear gradient of 10–70% B in A during 30 min. and held isocratically for 10 min. at a flow rate of 1 mL/min. Detection was at 260 nm.

Cell culture, RSV propagation and infection, and viral titer assays.

The human tracheal epithelial cell line, 9HTE, (Gruenert et al., 1988) and CV-1 cells, (American Type Culture Collection, Rockville, Md., CCI#70) a green monkey kidney cell line which is highly permissive to RSV infection, were cultured in minimal essential medium (MEM) supplemented with 10% (v/v) fetal bovine serum (FBS), 2 mM L-glutamine, 1×MEM amino acids solution, 1×MEM non-essential amino acids solution, 100 U/ml penicillin, 100 µg/ml streptomycin and 0.25 µg/ml amphotericin B ("culture medium") (all reagents from Gibco BRL, Bethesda, Md.). RSV strain $A_2$ (ATCC No. VR1302) was propagated in CV-1 cells. CV-1 monolayers were infected at a multiplicity of infection (M.O.I.) of 0.2 and cultured 46 h in MEM, 2% FBS, 1×Penicillin/Streptomycin (PS) in 5% $CO_2$, 95% $O_2$ at 37° C. Cells were then washed 2 times in MEM and subsequently covered in MEM, 2% FBS, 1×PS, 50 mM HEPES (pH7.5), 100 mM $Mg(SO_4)$. After 2 h at 37° C., cells were scraped and sonicated as previously described (Panuska et al., 1995). Aliquots (1 ml each) of cell sonicates were flash frozen in ethanol/dry ice within 20 min of scraping. Several aliquots were then thawed and titered by a plaque assay on CV-1 cells as previously described (Cirino et al., 1993). The range of virus yield from this procedure was 2 to $7×10^6$ plaque forming units (pfu) per ml.

Oligonucleotide, interferon α and ribavirin treatments of 9HTE cells before and after RSV infection.

Infection of 9HTE cells was performed as previously described (Merolla et al., 1994). Briefly, confluent monolayers were exposed to RSV diluted in MEM, 2% FBS, for 2 h at 37° C. in 5% $CO_2$, 95% $O_2$. After exposure, cells were washed two times with serum-free MEM media and then fresh culture media (with 10% FBS) was added. Oligonucleotides were either added 4 h prior to infection ($t_{-4}$) or immediately after infection ($t_{+2}$) and also at $t_{+14}$ and $t_{+26}$. Cells were harvested for plaque assays at 36 h post-infection to determine viral titers as previously described (Cirino et al., 1993). Cells were washed twice to remove any residual antisense and were then scraped in MEM containing 2% FBS, 1×PS. 9HTE cells were sonicated for 20 sec on ice then the extracts were serially diluted and transferred to a confluent monolayer of CV-1 for quantitation of infectious viral particles. CV-1 were exposed to sonicated 9HTE for 2 h then washed once in MEM and overlaid with Eagle's minimal essential medium (EMEM, BioWhittaker, Walkersville, Md.) containing 2% FBS, 200 U/ml penicillin, 200 µg/ml streptomycin, 0.5 µg/ml amphotericin B, and 0.4% agarose. Five days later, cells were fixed in 10% formalin for 1 h, the agarose plugs removed, and 0.2% crystal violet in 10% formalin was added for 2 min. CV-1 were subsequently washed in water to remove excess dye and the number of syncytia (plaques) were quantified under a microscope.

In certain experiments (data not shown), interferon α (Schering, Intron A, interferon α-2B, $10^5$ U/ml) or Ribavirin (ICN Pharmaceuticals, Costa Mesa, Calif., 100 µg/ml) were also added after infection. Interferon α was added to a final concentration of 50 U/ml when chimeric antisense was added, i.e. $t_{+2}$, $t_{+14}$ and $t_{+26}$. In contrast, ribavirin, which has a half-life of 40 days in vivo, was added only at $t_{+2}$ to a final concentration of $10^{-13}$ M.

Reverse transcriptase-coupled polymerase chain reaction (RT-PCR)

RNA was collected from $2×10^5$ 9HTE cells at 8 h post-infection (M.O.I.=10) by RNAzol treatment as described by the manufacturer (Tel-Test, Inc, Freindswood, Tex.). RNA was isolated after 8 h to limit RSV replication to a single cycle. Isolated RNA (≈1 µg) was incubated with 100 pmoles of the appropriate downstream (−) primer listed below or 100 pmoles of random hexamer (used for glyceraldehyde-3-phosphate dehydrogenase, GAPDH, mRNA only). RNA and primers were heated to 70° C. for 10 min then cooled rapidly on ice for 5 min. A final reaction volume of 30 ml contained: 300 µM each dNTP, 200 U SuperScript reverse transcriptase (GibcoBRL, Bethesda, Md.), 50 mM Tris-HCl (pH 8.3), 75 mM KCl, 3 mM MgCl2, and 10 mM DTT. Reverse transcription was allowed to proceed for 1 h at 37° C.

PCR reactions were performed using 50 µl Hot-Start tubes (Molecular Bio-Products, San Diego, Calif.) with 25 µl lower buffer containing 40 mM Tris-HCl (pH=8.4), 100 mM KCl, 2 mM MgCl2, 600 µM each dNTP, and 100 pmoles each of the appropriate primer pairs;

| TARGET | SEQUENCE | ANNEALING TEMP |
|---|---|---|
| RSV(L+) (Seq ID NO: 1) | [5'-TCAATGGTCCTTATCTCAA-3'] | 46° C. |
| RSV(L−) (Seq ID NO: 2) | [5'-GAGCTTTATTAGCAGCATC-3'] | |
| GAPDH(+) (Seq ID NO: 3) | [5'-AAATCCCATCACCATCTTC-3'] | 57° C. |
| GAPDH(−) (Seq ID NO: 4) | [5'-CACCACCCTGTTGCTGTAG-3'] | |
| RSV(M2+) (Seq ID NO: 5) | [5'-AAACAATCAGCATGTGTTG-3'] | 46° C. |
| RSV(M2−) (Seq ID NO: 6) | [5'-AATGTAACGATGTGGTGAG-3'] | |

25 μl Hot-Start upper buffer contained 5 U Taq DNA polymerase (GibcoBRL) and ⅟₁₀th of the cDNA from the RT reaction. 30 cycles of PCR were performed with 1 min at 92° C., 1.5 min at the annealing temperature indicated above, and 2 min at 72° C. Aliquots of the RT/PCR mixtures were analyzed on 1% agarose/TBE gels.

EXAMPLE 8
RESULTS 2-5A antisense inhibits RSV replication in previously infected human tracheal epithelial cells.

To develop 2-5A antisense chimeras with the potential to block RSV replication, we first selected an oligonucleotide binding site in the viral RNA polymerase (RSV L) mRNA, which encodes a low abundance message that is absolutely required for RSV replication. The first chimera synthesized and evaluated was pA$_4$-antiRSV/(8490–8509). The binding sites for the chimeric oligonucleotide's antisense domain are to the transcripts of nucleotides 8490–8509 in the RSV genome, which spans the translation start codon for the L protein, and to nucleotides 8490–8509 of the antigenomic strand (the template for reproduction of the genome). Since to function as an effective treatment, a candidate agent must be able to inhibit viral replication subsequent to diagnosis, the anti-RSV effect of the 2-5A antisense chimera was determined on human tracheal epithelial cells, 9HTE, with treatments beginning either 4 h before RSV infection (pre-/post-infection treatments) or 2 h following infection (post-infection treatments). In the post-infection treatments, pA$_4$-antiRSV/(8490–8509) at (10 μM final concentration), was added at t$_{+2}$, t$_{+14}$ and t$_{+26}$, (numbers represent time in h relative to time of infection, t$_0$). For pre-infection treatment, pA$_4$-antiRSV/(8490–8509) (10 μM final concentration), was added at t$_{-4}$, and t$_0$ in addition to t$_{+2}$, t$_{+14}$ and t$_{+26}$. Virus harvested from control and oligonucleotide-treated 9HTE cells was measured by infecting CV-1 cells and subsequently counting viral plaques (see Materials and Methods). Post-infection treatment of 9HTE cells with pA$_4$-antiRSV/(8490–8509) was found to be just as effective as pre-/post-infection treatment; both resulted in about 70% inhibition of RSV replication. On the basis of these experiments, all subsequent experiments were performed with post-infection treatments only. Additionally, these experiments indicate the potential use of these compounds as a treatment for active infection as compared to a prophylactic measure.

Antiviral activities of 2-5A antisense and control chimeric oligonucleotides directed against the viral L polymerase mRNA translation start site.

An initial series of oligonucleotides included various controls and additional modifications designed to stabilize the chimeras against enzymatic decay in the cell culture (Table 3). To compare the antiviral effects of these oligonucleotides, 9HTE cells were infected with RSV and subsequently treated three times (t$_{+2}$, t$_{+14}$, and t$_{+26}$ h) with three concentrations of oligonucleotides (3.3, 6.6 and 9.9 μM) and virus was harvested after 36 h. Chimeric antisense lacking only the 5'-phosphate, in A$_4$-antiRSV3'-3'C/(8490–8509), deficient in the ability to activate RNase L (Maran et al., 1994), was used as a control. This derivative showed only minimal anti-RSV activity (28.3% inhibition at 9.9 μM/treatment as compared to 64.8% inhibition by the 5'-phosphorylated derivative, pA$_4$-antiRSV3'-3'C/(8490–8509)). To stabilize the 3' termini of the chimeras, these ends were masked. In one derivative, pA$_4$-3'antiRSV5'/(8490–8509), the 2-5A portion of the chimera was linked to the 3' end of the antisense moiety instead of to the 5' end of the oligonucleotide. In this way, the 3' terminus of the antisense is protected from exonuclease digestion though its attachment to the linker (G.L., W.X., & P.F.T., unpublished observations). This analog produced a 69% inhibition of virus production at the highest concentration tested (9.9 μM) (Table 3). In another chimera, pA$_4$-antiRSV3'-3'C/(8490–8509), the 3' terminal deoxynucleotide was connected by a 3'-3' phosphodiester linkage to the penultimate deoxynucleotide thereby slowing 3' exonuclease digestion (G.L., W.X., & P.F.T., unpublished observations). This compound produced a 1.6-fold enhanced antiviral activity at 6.6 μM (64.3% inhibition) compared with the standard, unmodified chimera, pA4-antiRSV3'-3'C/(8490–8509) tested at the same concentration (38.8% inhibition). Alternately, a 5'-thiophosphate was used to stabilized the 2-5A domain of the chimera against phosphatase. Such thiophosphorylated derivatives of 2-5A and 2-5A antisense were previously shown to be fully capable of activating RNase L when compared to standard, 5'-phosphorylated, 2-5A and 2-5A antisense (Xiao et al., 1994 and Maran et al., 1994). spA$_4$-antiRSV/(8490–8509) showed a substantially increased anti-RSV effect with 71% and 94% inhibition of viral growth at treatment concentrations of 6.6 and 9.9 μM, respectively (Table 3).

EXAMPLE 9
SELECTION OF TARGET

Selection of highly effective 2-5A antisense chimera based on a computer analysis of the RNA secondary structure.

A computer-assisted analysis of the secondary structure of the RSV mRNA was performed to identify single-stranded regions as oligonucleotide binding sites. Computer prediction of the secondary structure of RSV antigenomic strand, nucleotides 7900 to 9079, including a 3' portion of the M2 gene, encoding a viral envelope protein, and a 5' region of the L gene, was performed using the program MFOLD which finds a secondary structure of minimum free energy for an RNA molecule based on published values of stacking and loop destabilizing energies. MFOLD is the program of Michael Zuker (Zuker, 1989). The energies used by Zuker's program were first described by Salser (1977) and are now defined by Turner and colleagues (Freier et al., 1986). The analysis showed a large loop from positions 8250 to 8299. This loop was present in a 90 codon open reading frame of unknown function downstream (3') of the major M2 open reading frame. Three chimeric compounds were synthesized which were complementary to sequences in the loop, spA$_4$-antiRSV3'-'3A/(8251–8270), spA$_4$-antiRSV3'-3'T/(8261–8279), and spA$_4$-antiRSV3'-3'T/(8281–8299). In addition, three oligonucleotides were synthesized to other regions in RNA that included a bulge, a hair-pin and a small loop, spA$_4$-antiRSV3'-3'A/(8530–8547), spA$_4$-antiRSV3'-3'C/(8561–8578), and spA$_4$-antiRSV3'-3'G/(8599–8618), respectively. When added to the infected 9HTE cells at concentrations of 3.3 μM, the three oligonucleotide directed to the large loop had the greatest level of antiviral activity (78 to 91% inhibition) (Table 4). These three oligonucleotides had very substantially improved anti-RSV activity compared to the previously described 2-5A antisense molecules (3 to 16.5% inhibition at 3.3 μM, see Table 3). The chimera with the greatest anti-RSV effect was spA$_4$-antiRSV3'-3'T/(8281–8299), which produced 97 and 99.6% inhibition of RSV replication at doses of 6.6 and 9.9 μM, respectively. The oligonucleotide directed to the region in the RNA with the bulge, spA$_4$-antiRSV3'-3'A/(8530–8547), showed almost no antiviral effect at 3.3 μM (Table 4). The 2-5A antisense molecules to the hairpin and small loop, spA$_4$-antiRSV3'-3'C/(8561–8578), and spA$_4$-antiRSV3'-3'G/(8599–8618), had intermediate activities, 57 and 43% inhibition of RSV replication at concentrations of 3.3 μM.

Figure 3A:
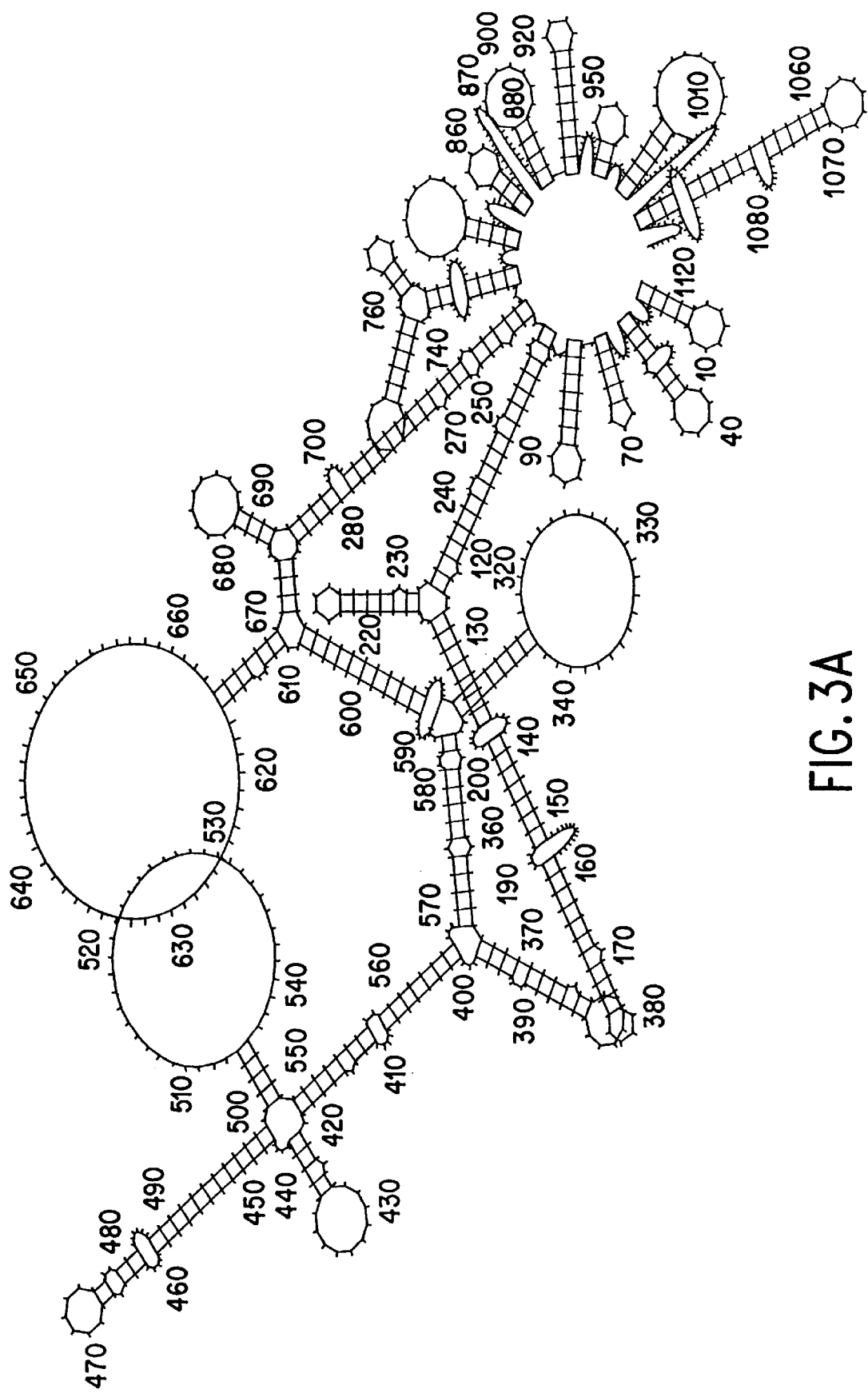
FIGS. 3A–3C. Three alternative squiggle plots of residues 1–1124 of RSV antigenomic RNA.
Figure 3B:
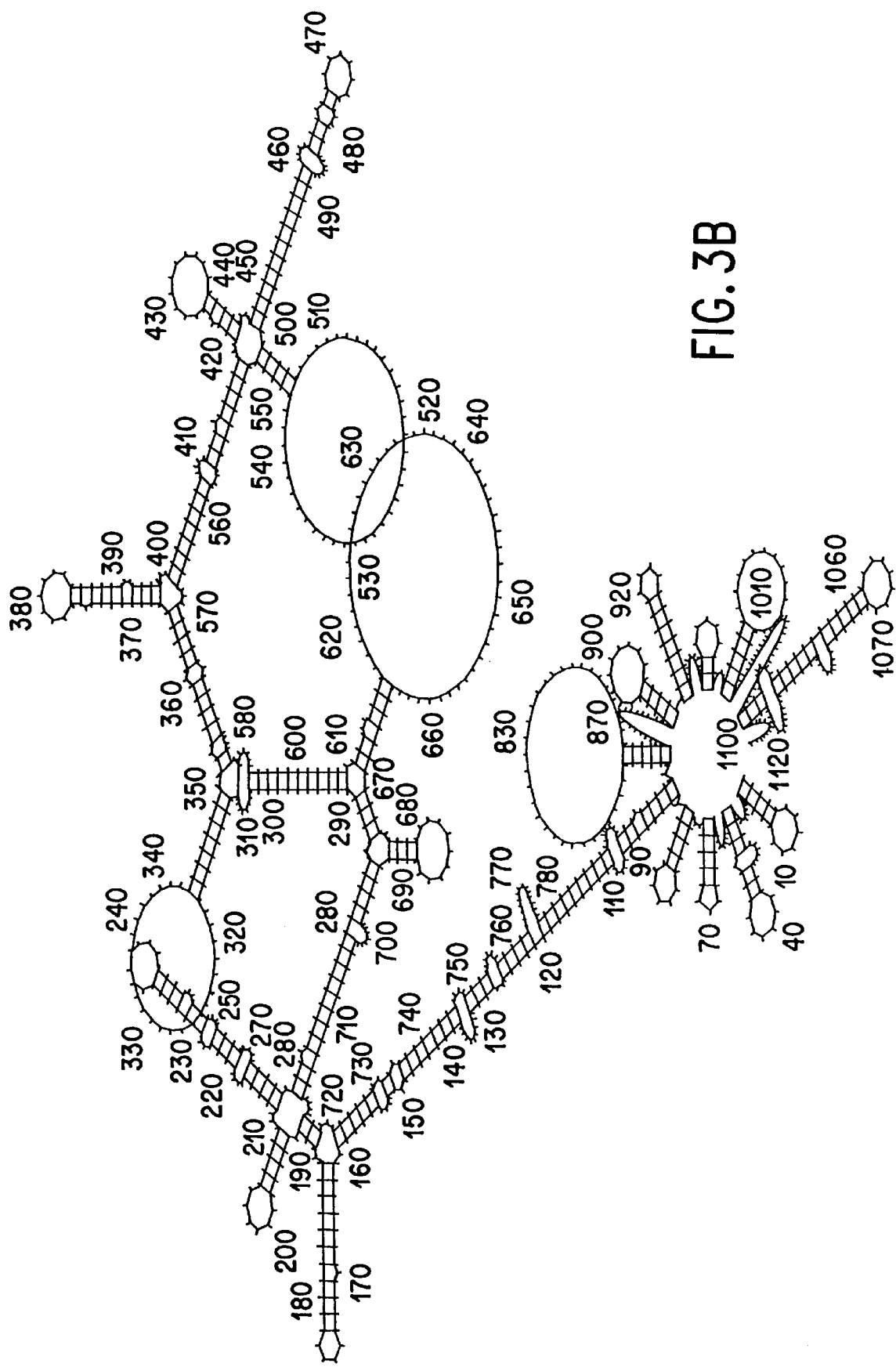
Figure 3C:
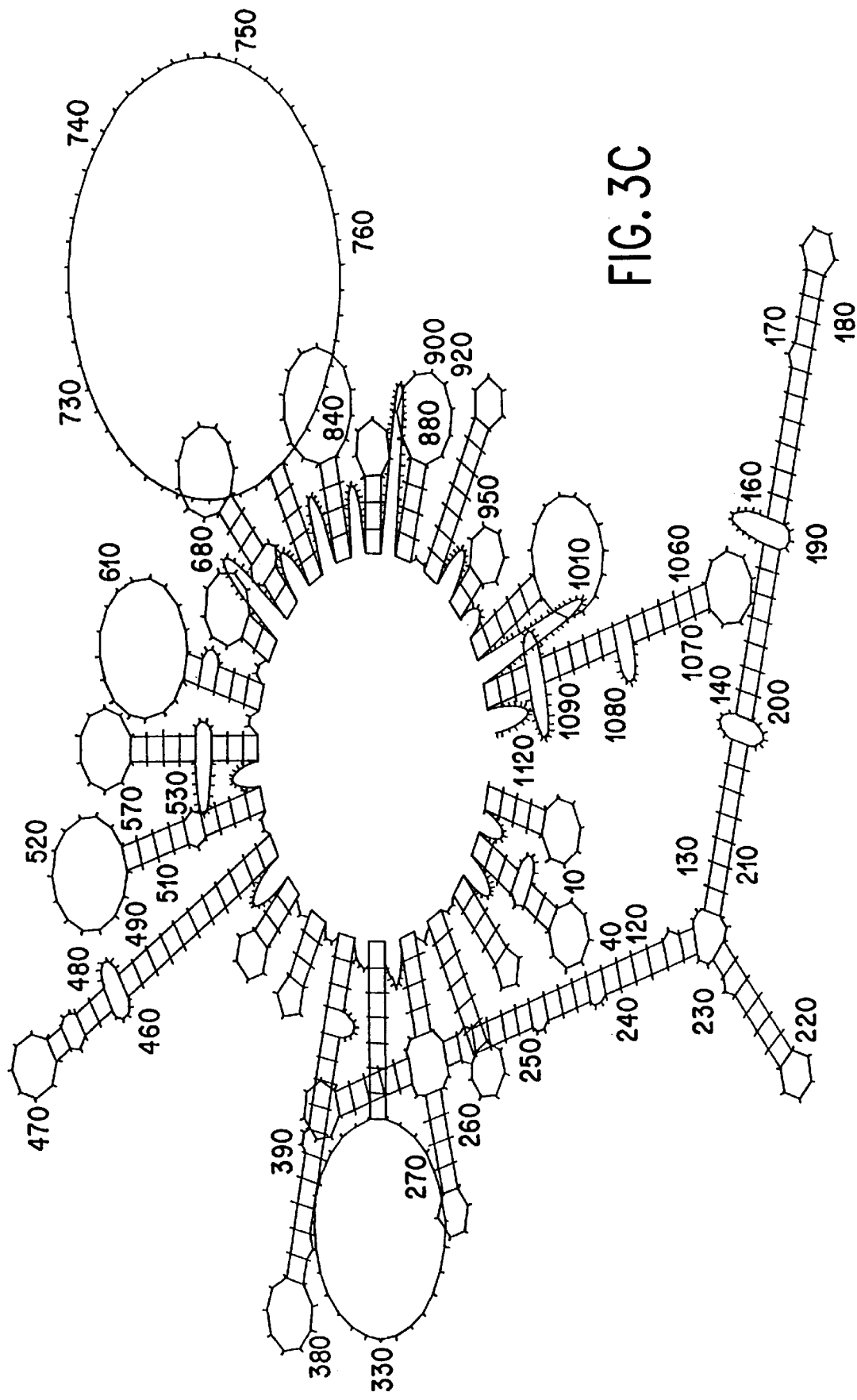
Figure 4A:
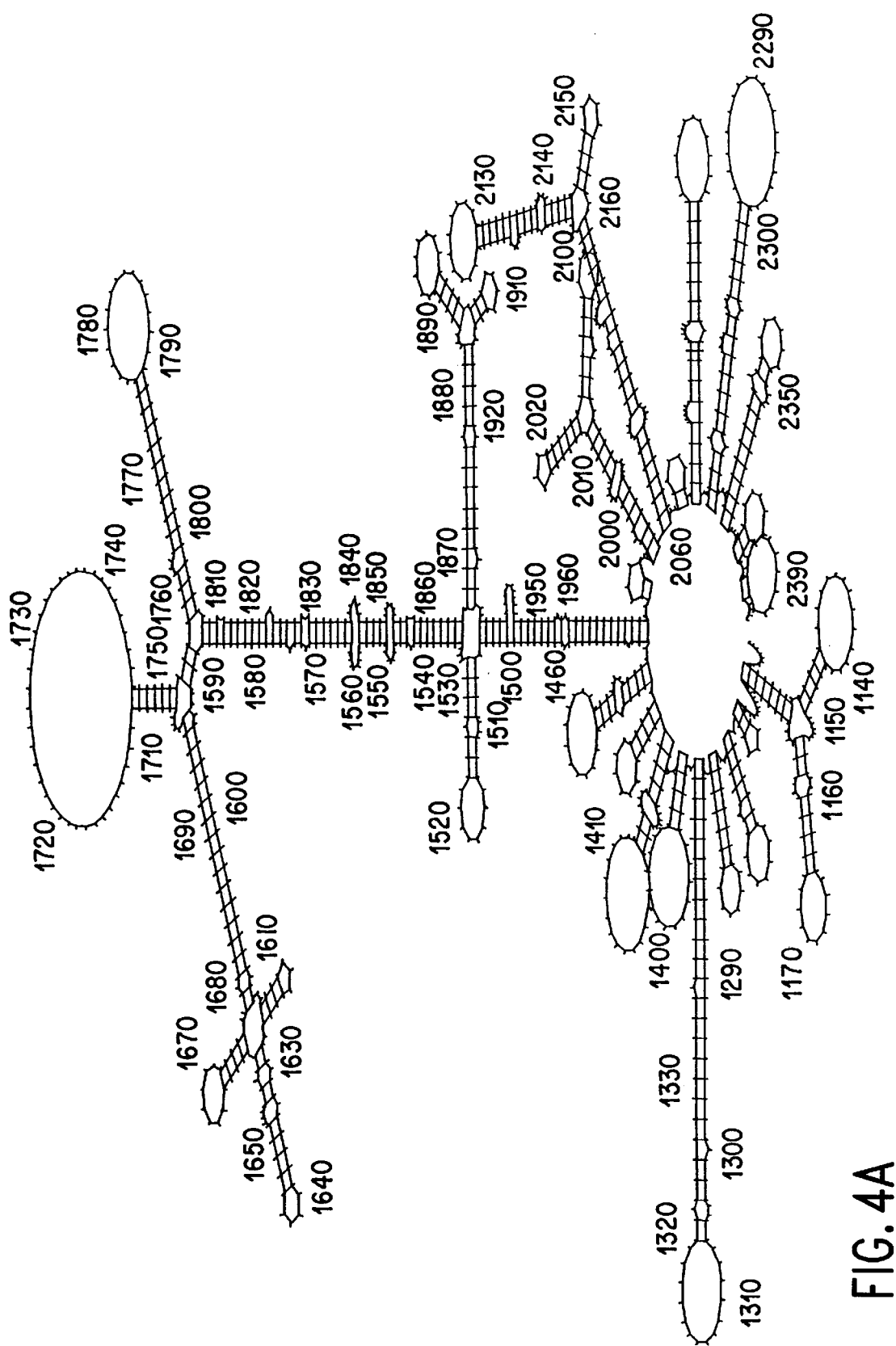
FIGS. 4A–4C. Three alternative squiggle plots of residues 1100–2400 of RSV.
Figure 4B:
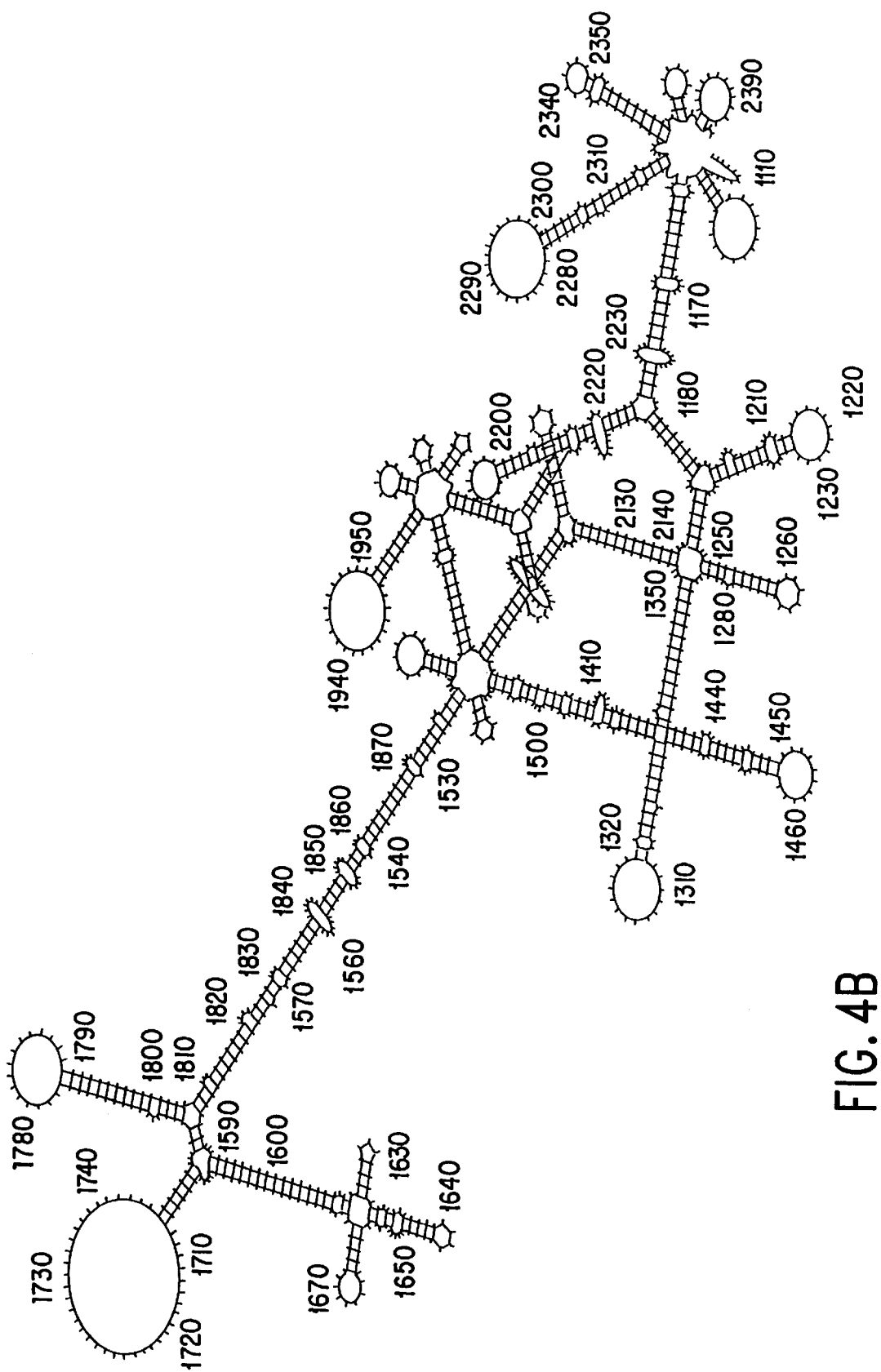
Figure 4C:
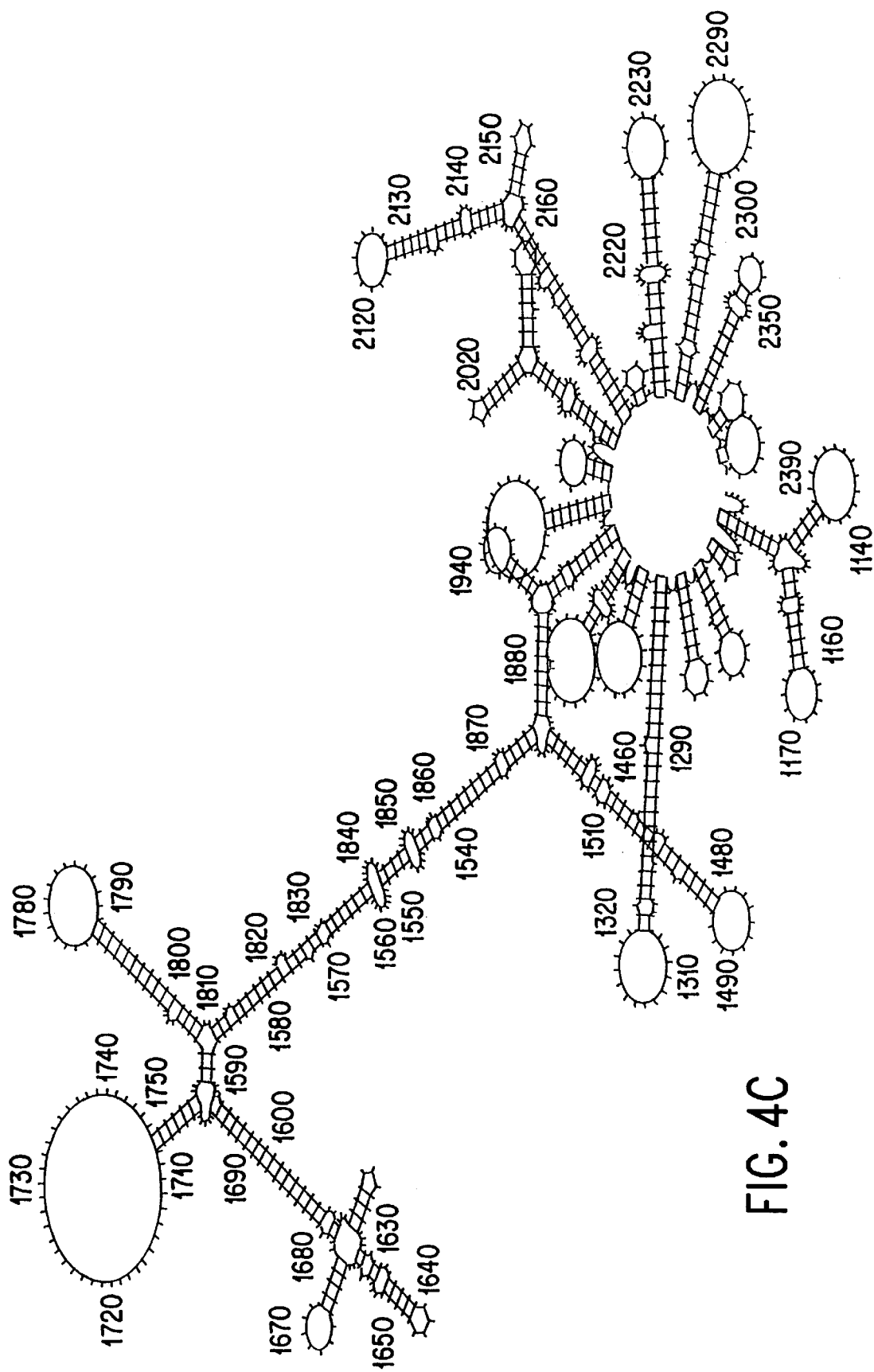
Figure 5A:
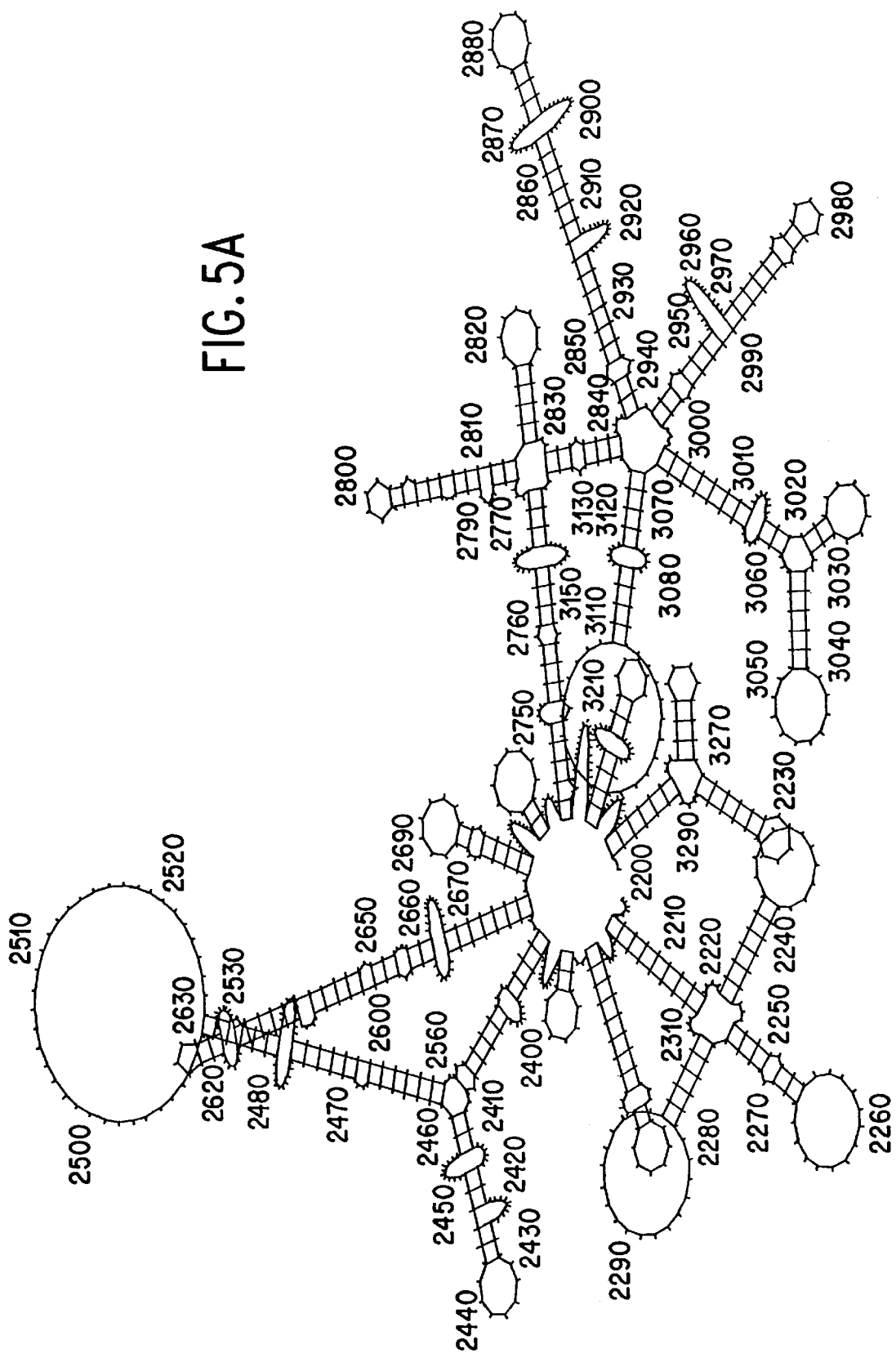
FIGS. 5A–5C. Three alternative squiggle plots of residues 2200–3300 of RSV antigenomic RNA.
Figure 5B:
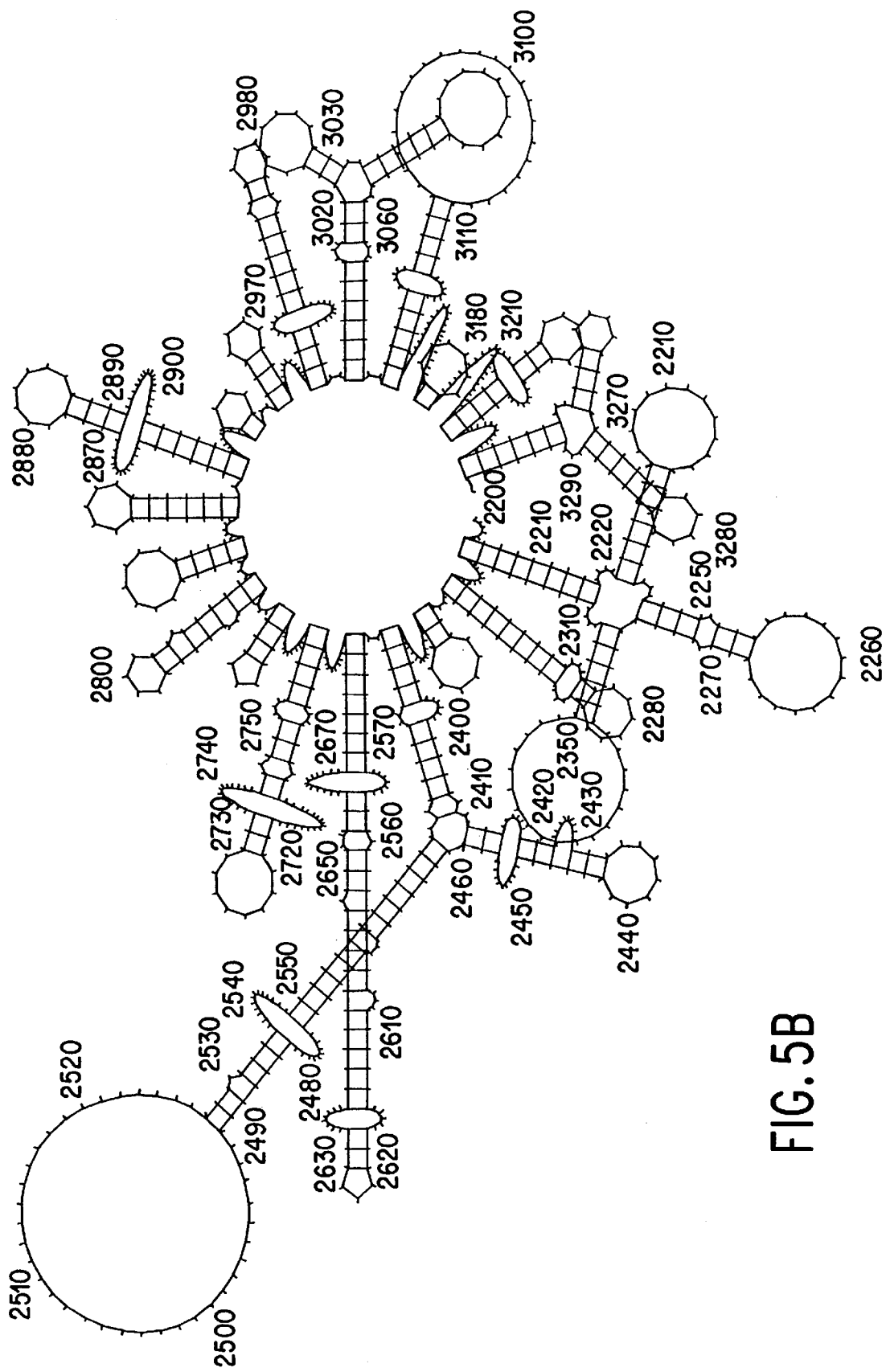
Figure 5C:
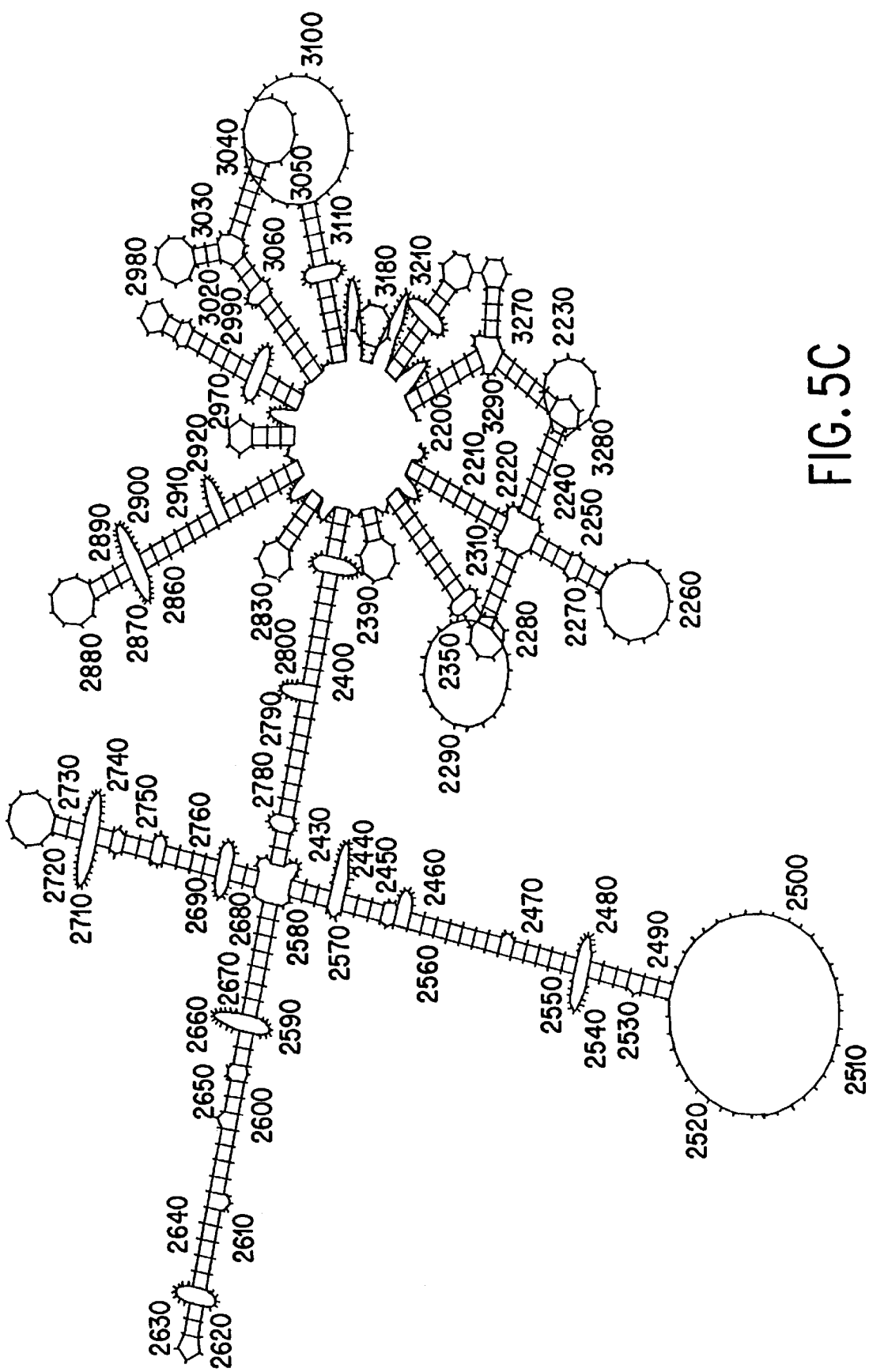
Figure 6A:
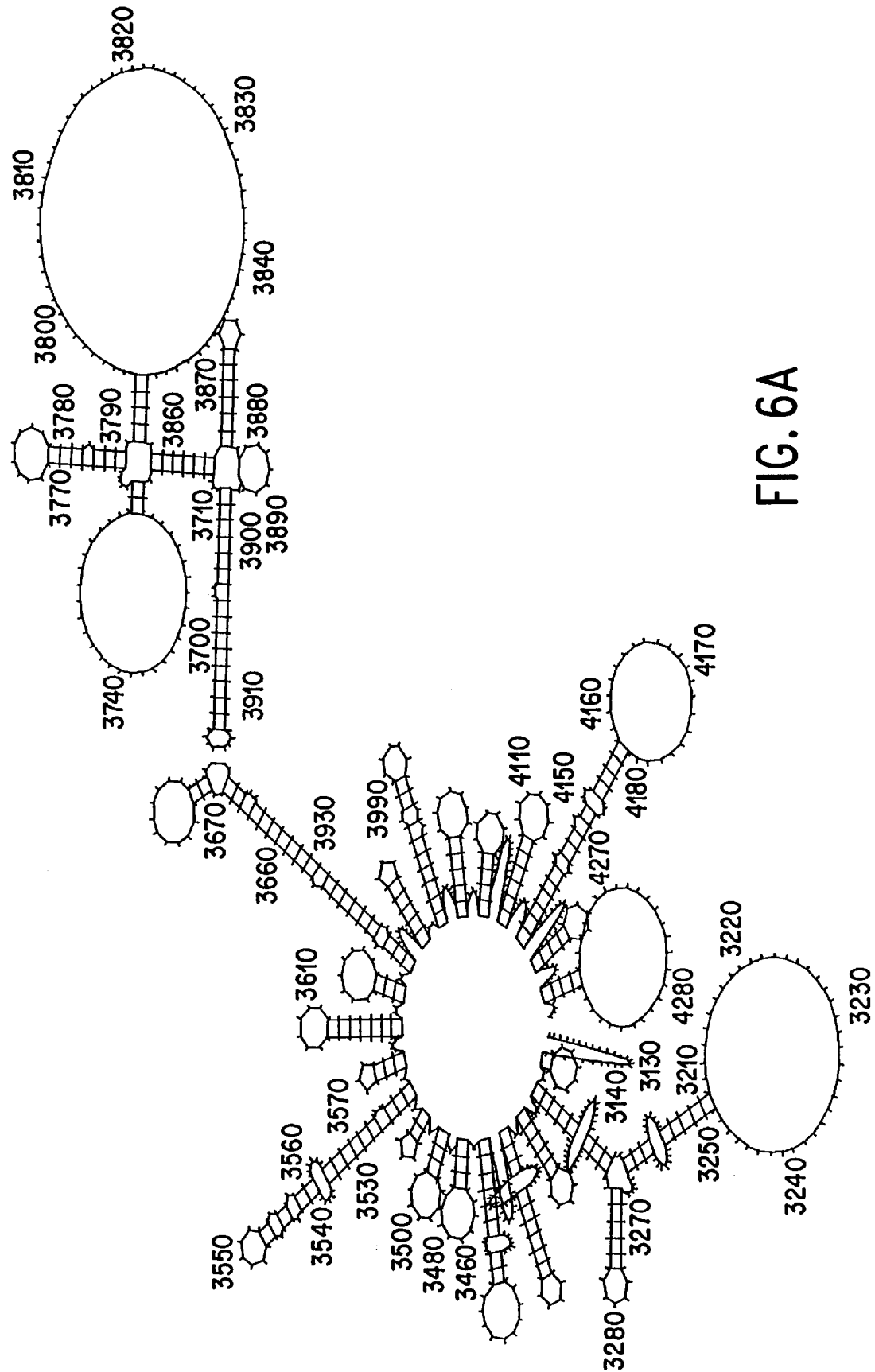
FIGS. 6A–6B. Two alternative squiggle plots of residues 3100–4300 of RSV antigenomic RNA.
Figure 6B:
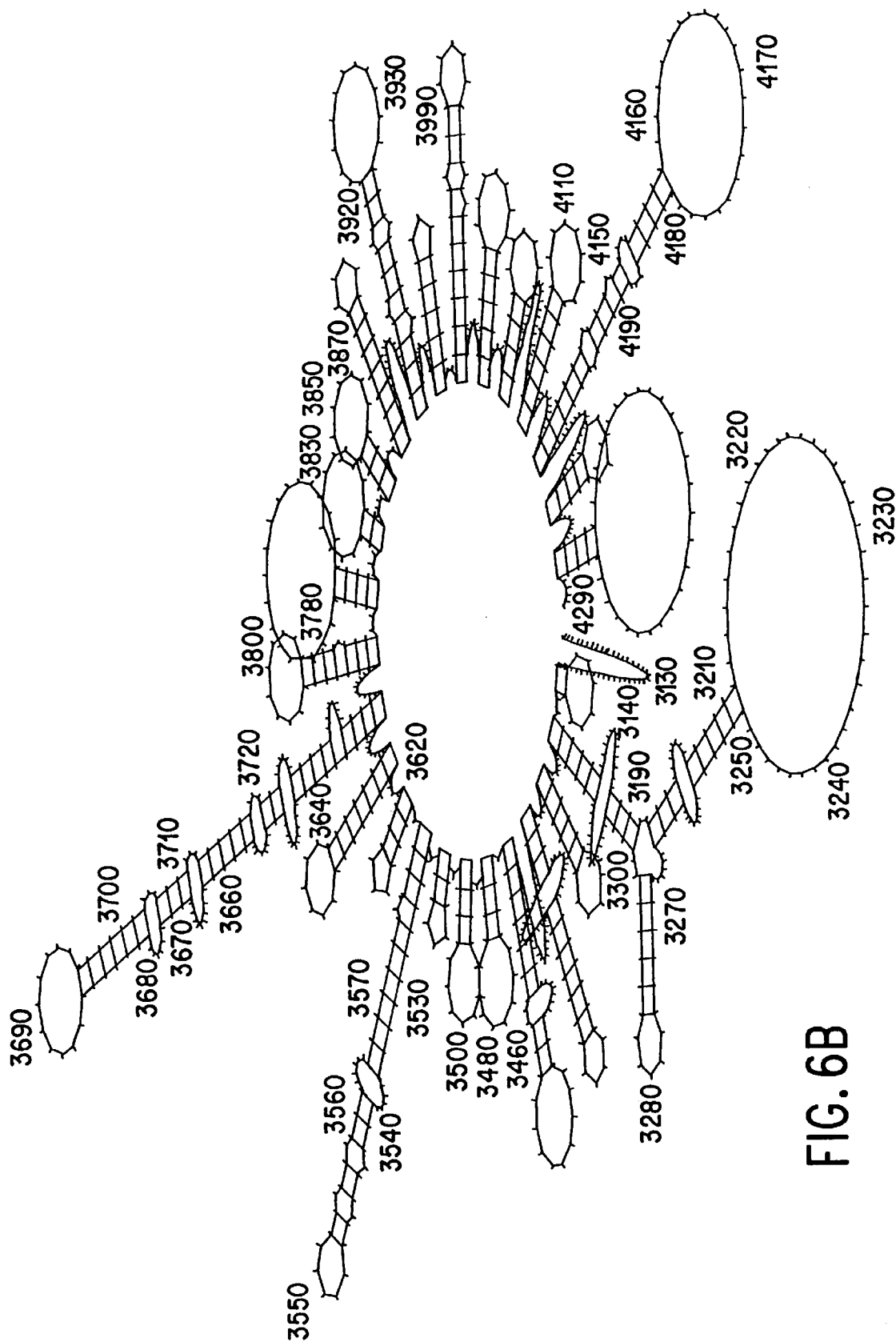
Figure 7A:
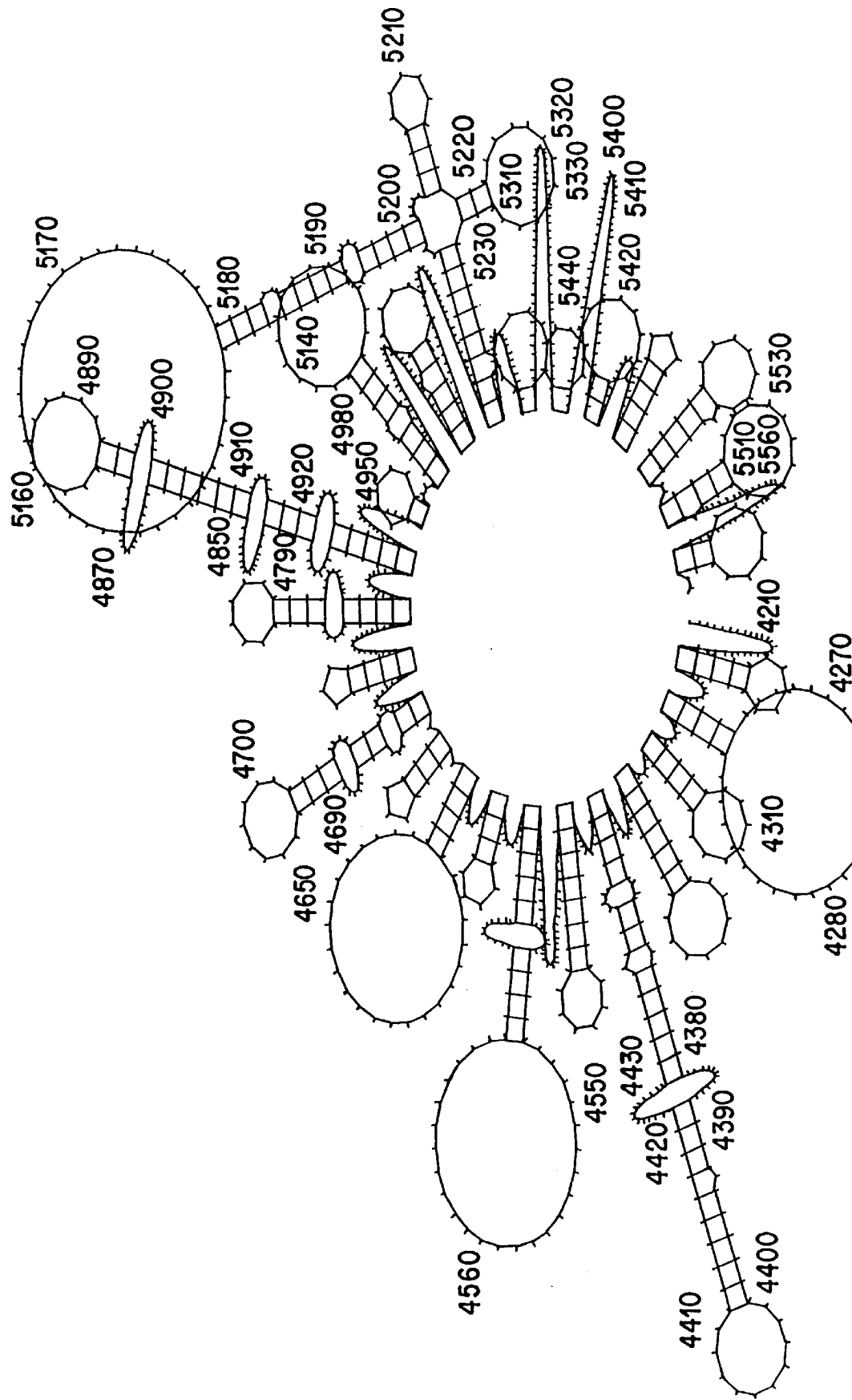
FIGS. 7A–7C. Three alternative squiggle plots of residues 4200–5599 of RSV.
Figure 7B:
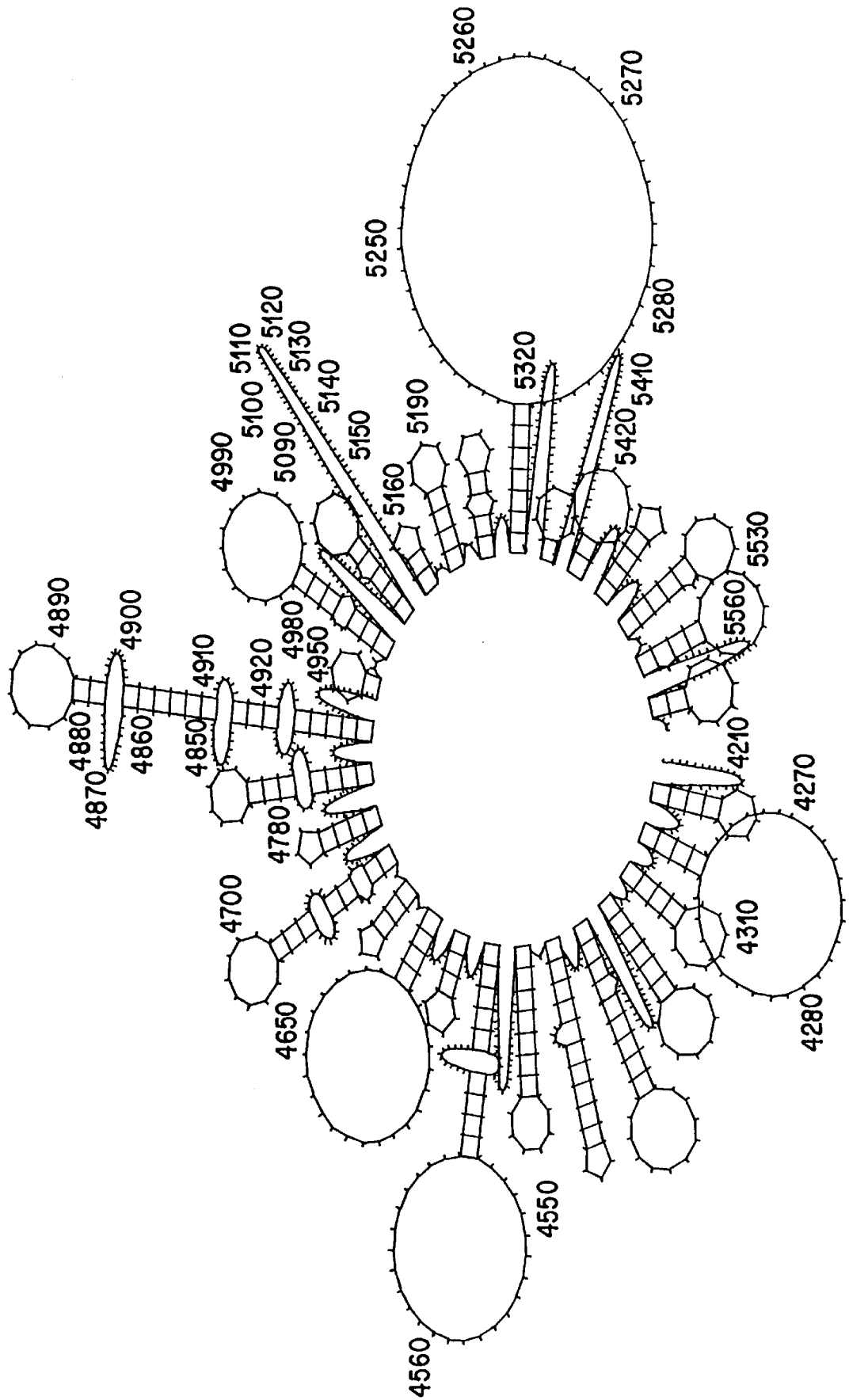
Figure 7C:
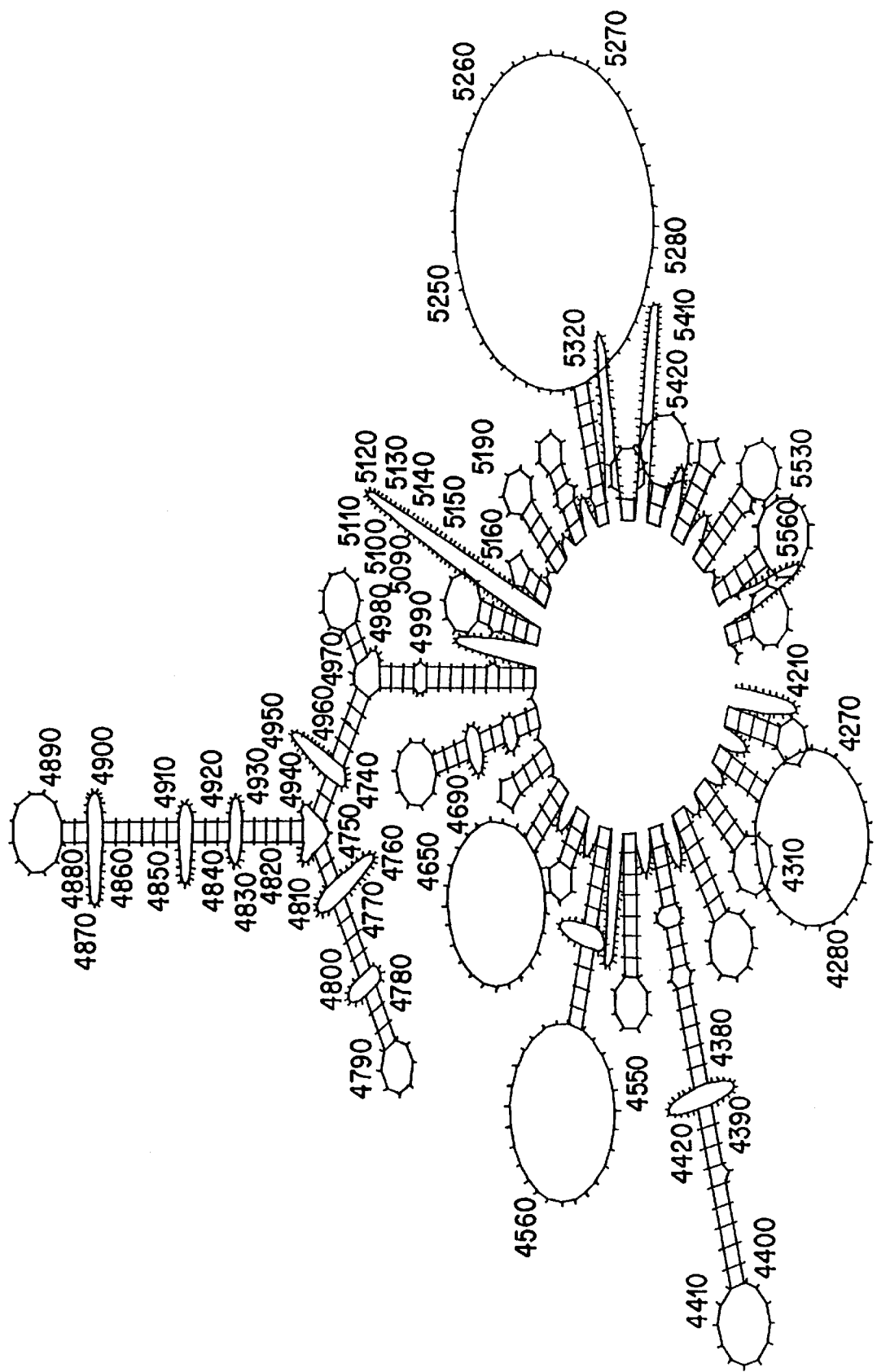
Figure 8A:
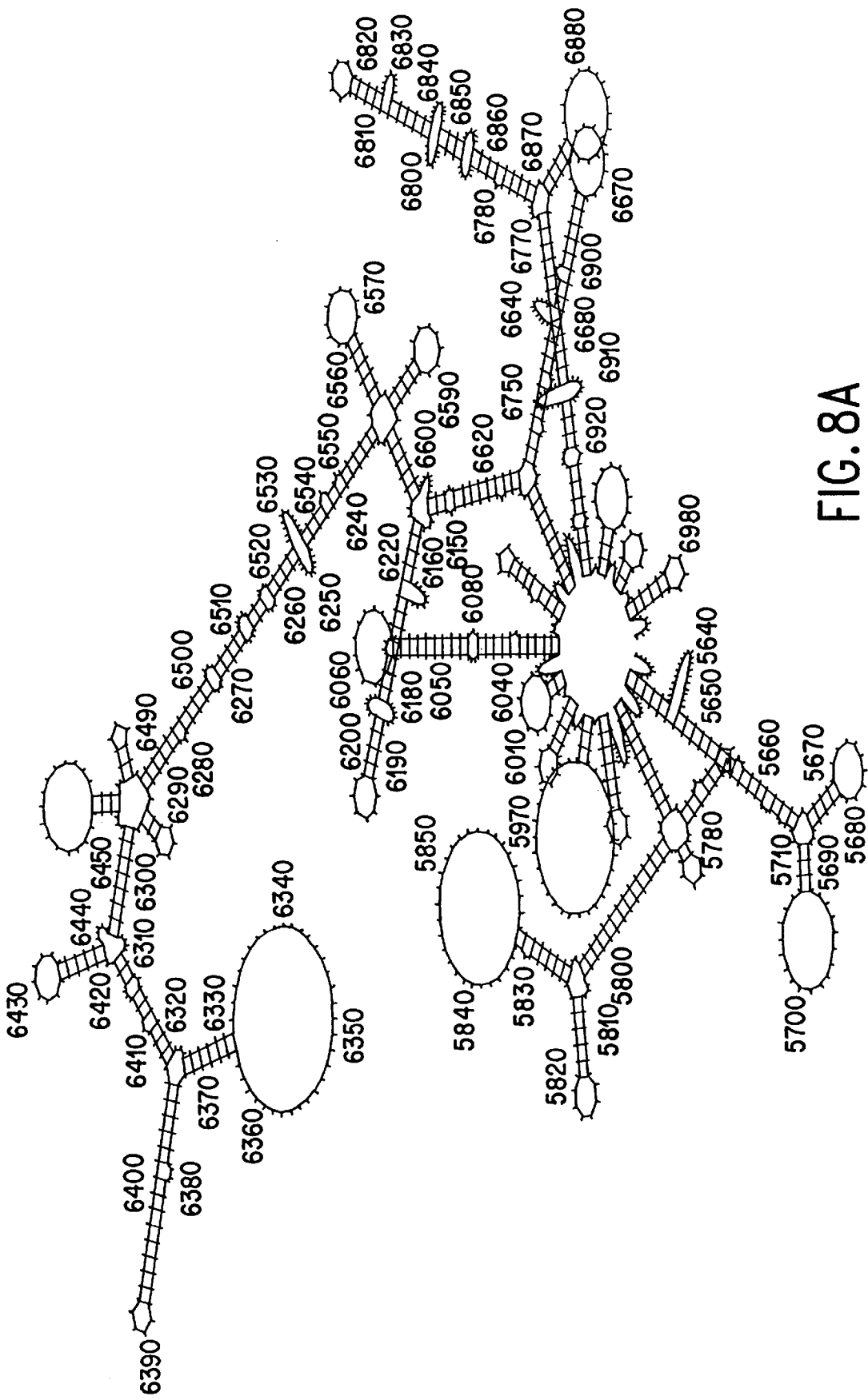
FIGS. 8A–8C. Three alternative squiggle plots of residues 5600–6999 of RSV antigenomic RNA.
Figure 8B:
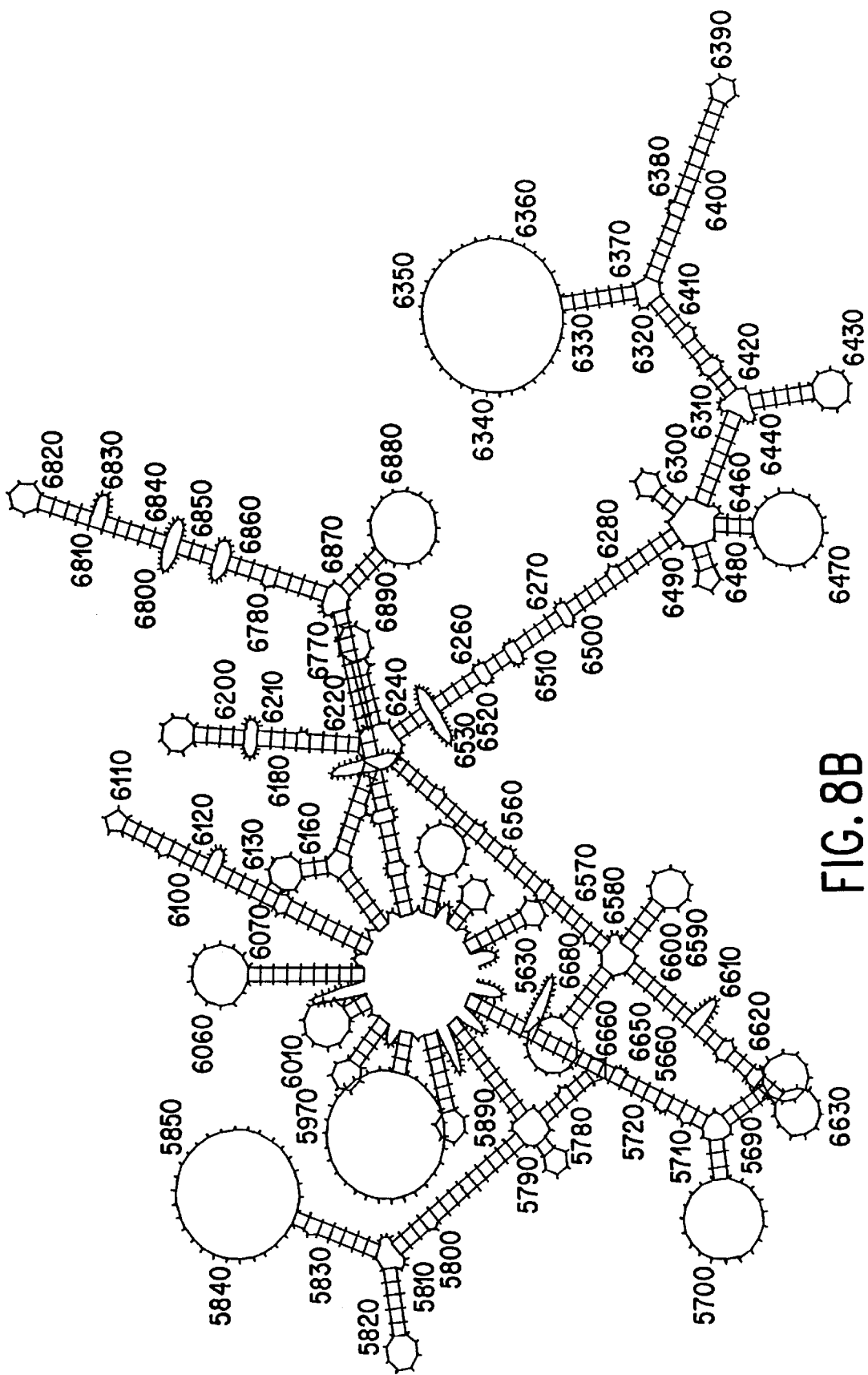
Figure 8C:
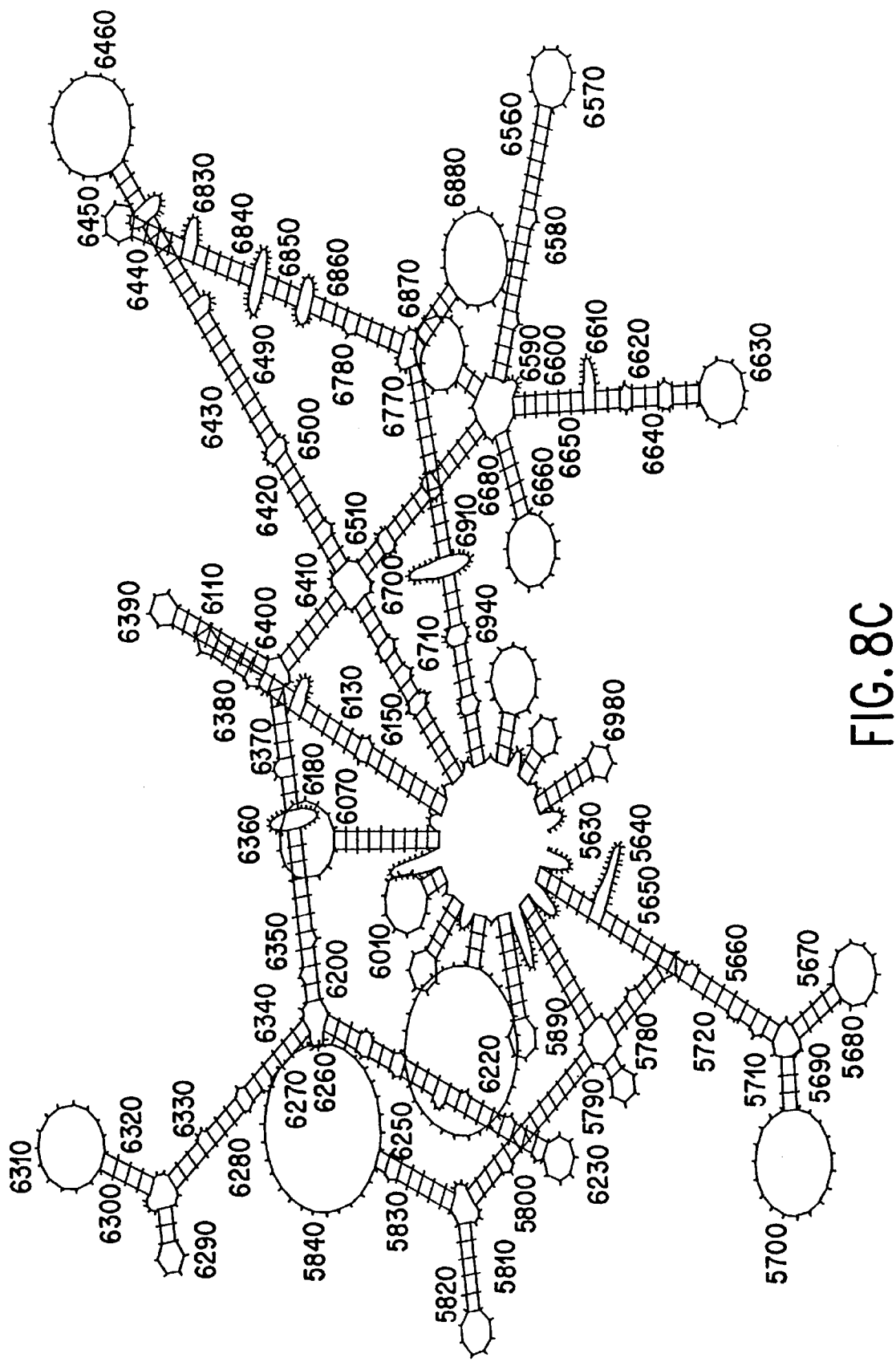
Figure 9A:
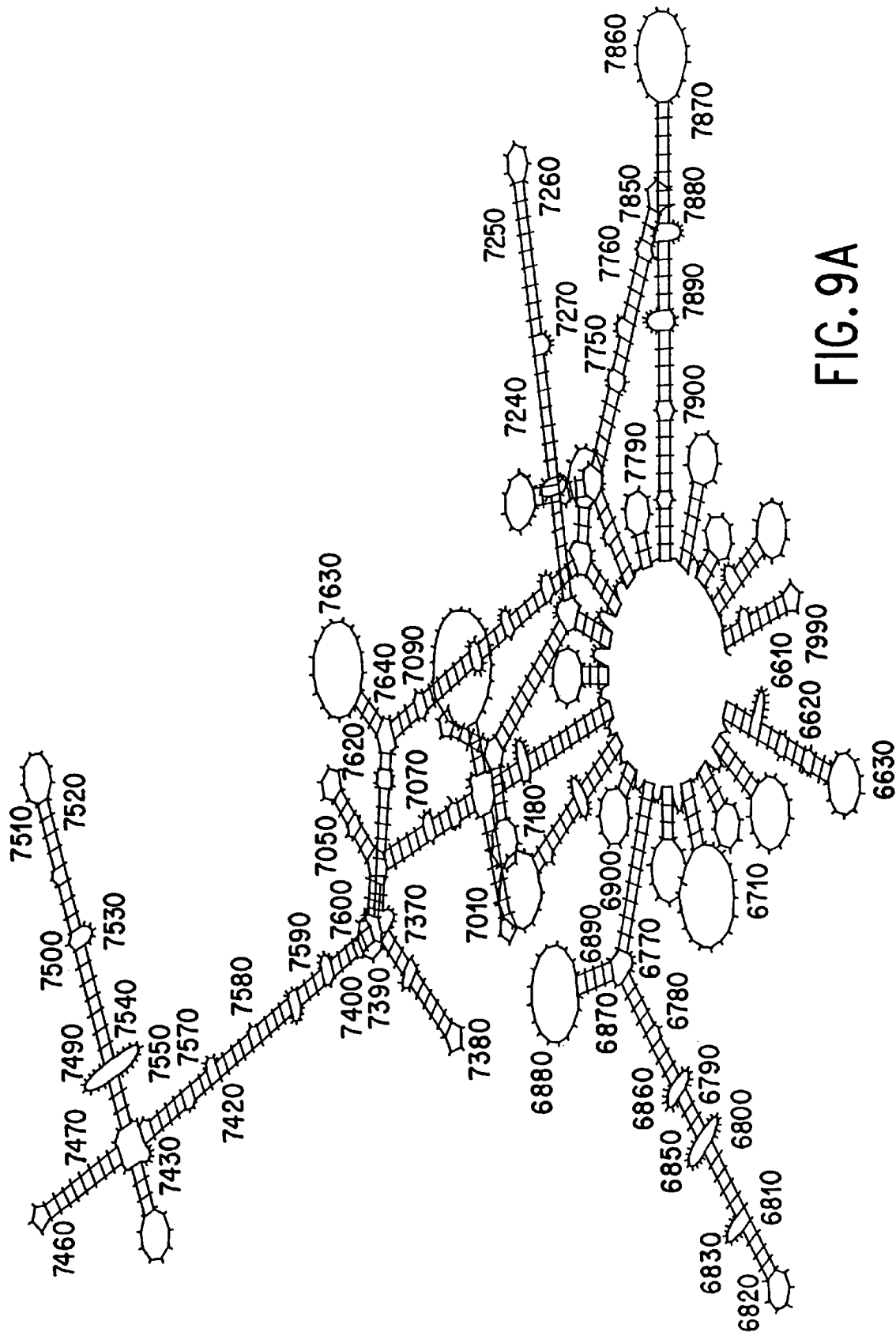
FIGS. 9A–9C. Three alternative squiggle plots of residues 6600–7999 of RSV antigenomic RNA.
Figure 9B:
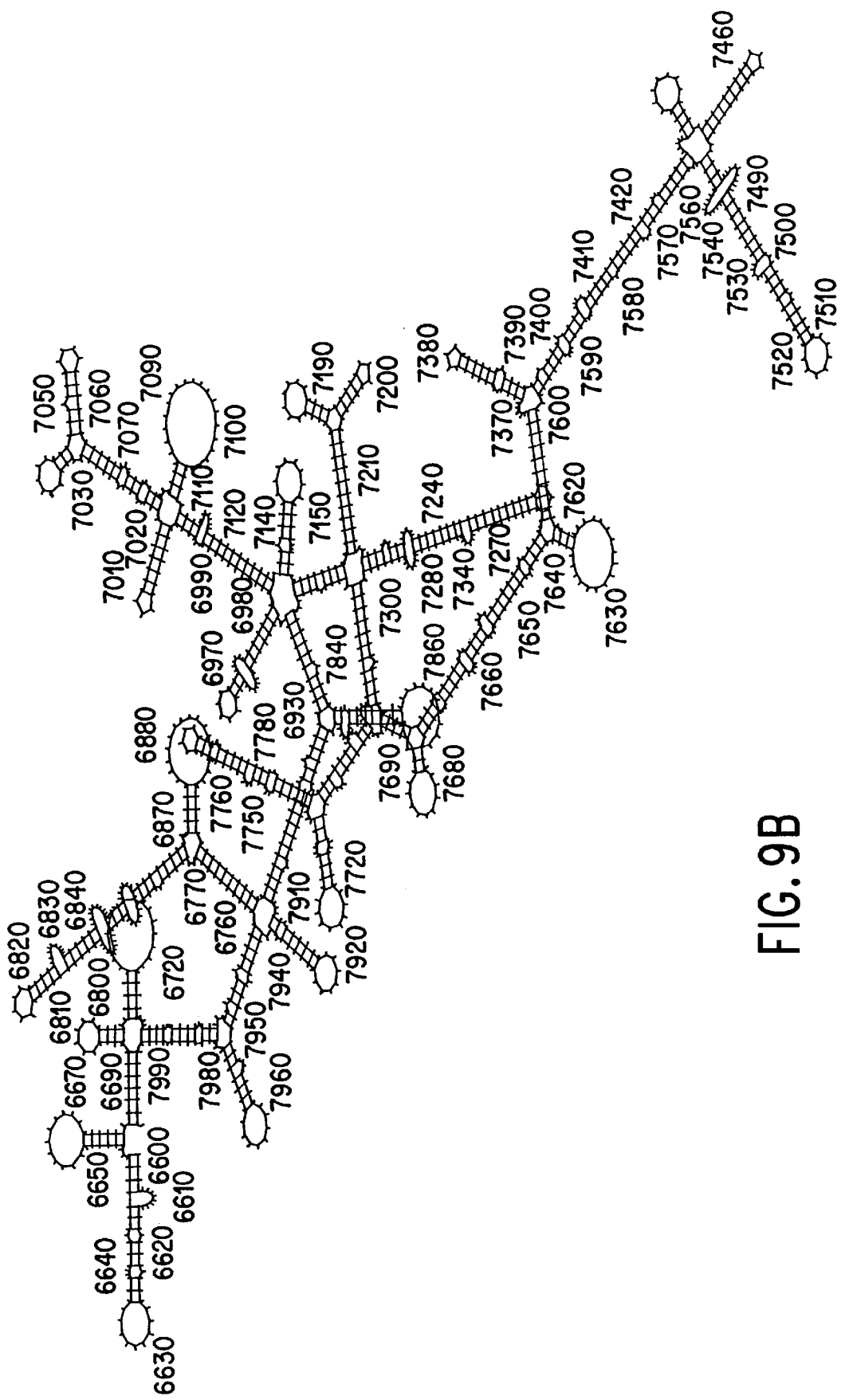
Figure 9C:
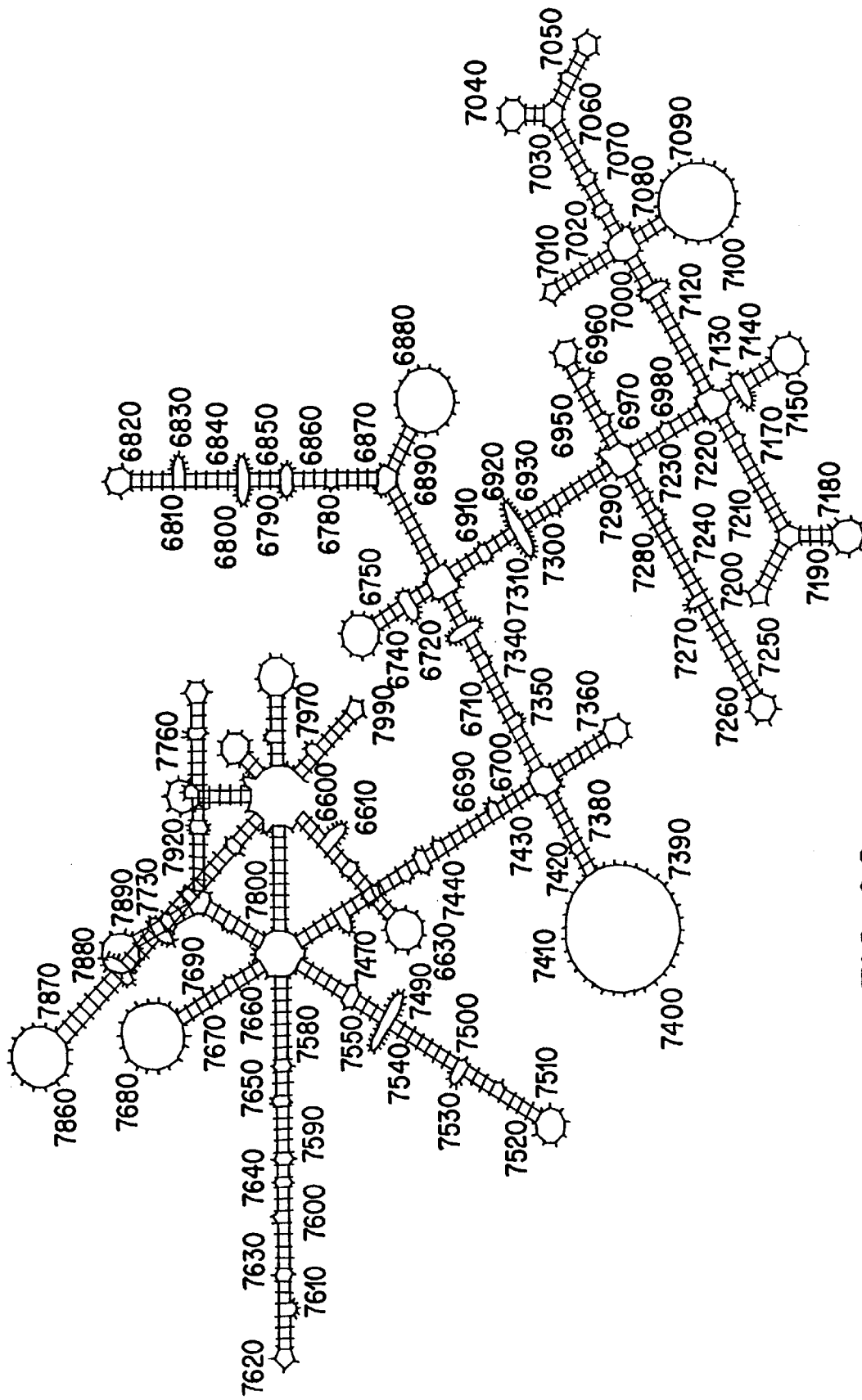
Figure 10:
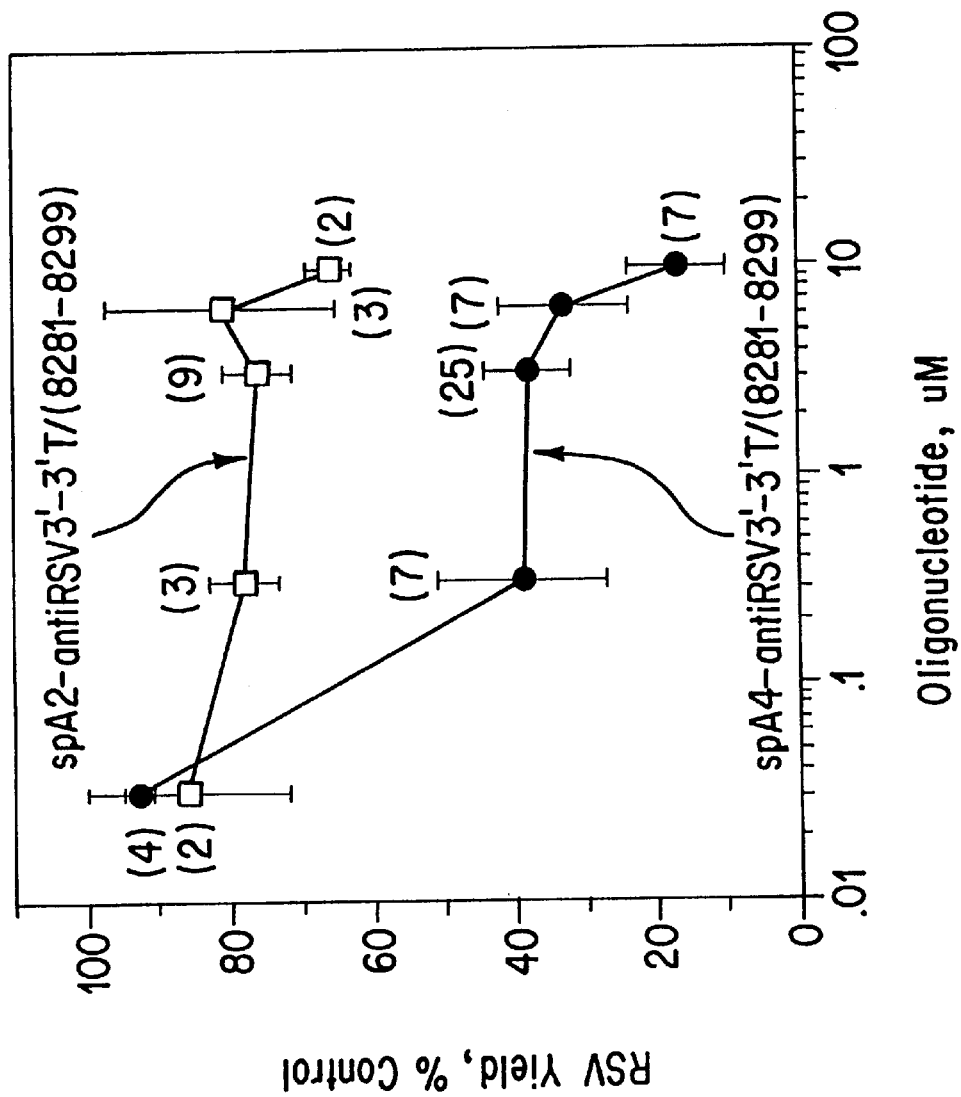
FIG. 10. Comparison of anti-RSV activities of $spA_4$-antiRSV3'-3'T/(8281–8299) and $spA_2$-antiRSV3'-3'T/(8281–8299).

FIG. 3 presents a comparison of spA$_4$-antiRSV3'-3'T/(8281–8299) and spA$_2$-antiRSV3'-3'T/(8281–8299). Only the tetraadenylate is an activator of RNase L, hence the greater potency of the spA$_4$-linked oligonucleotide compared to the spA$_2$-linked oligonucleotide establishes the role of RNase L activity in the protective effects of the present invention.

EXAMPLE 10
BIOCHEMICAL ANALYSIS OF RESULTS
Correlation of antiviral activities and RNA levels after treatment of RSV-infected 9HTE cells with the 2-5A antisense chimeras.

To determine if RSV RNA levels correlated with antiviral activity, RT-PCR analysis was performed on RNA isolated from RSV-infected and uninfected 9HTE cells with and without treatment with spA$_4$-antiRSV3'3'T/(8281–8299) or spA$_4$-antiRSV3'3'A/(8530–8547). An M2 RNA sequence in RSV (from nucleotides 7879 to 8465) was converted to cDNA and amplified by PCR (Materials and Methods). M2 RNA from the RSV-infected cells produced an RT-PCR DNA product that was clearly visible. In contrast, there was no M2 RNA detected from the RSV-infected cells treated with spA$_4$-antiRSV3'3'T/(8281–8299). The chimera directed against the RSV L mRNA and the corresponding sequence in the antigenomic RNA, spA$_4$-antiRSV3'3'A/(8530–8547), had little effect on levels of M2 RNA (17% inhibition). Accordingly, the levels of viral M2 RNA were dramatically reduced in 9HTE cells treated with spA$_4$-antiRSV3'-3'T/(8281–8299) while those treated with a relatively inactive control chimera against the RSV L mRNA, spA$_4$-antiRSV3'-3'A/(8530–8547), had no affect on levels of M2 RNA. Levels of GAPDH transcripts were similar in all of these RNA preparations. These results showing loss of the specific RSV mRNA target are consistent with involvement of RNase L.

EXAMPLE 11
OTHER ACTIVATOR-ANTISENSE COMPLEXES

The secondary structure of the 5' terminus of the RSV antigenomic strand can be more readily disrupted than the internal portions. Thus, the following activator-antisense complexes can be used to practice the invention despite the absence of large loops in modeling of the secondary structure of the antigenomic strand.

spA$_4$-antiRSV3'-3'T/(1-19): (Seq ID NO:7)
  sp5'A2'(p5'A2')$_3$—[(Bu)p]$_2$—(5'ttg tac gca ttt ttt cgc g3'-3't5')

spA$_4$-antiRSV3'-3'T/(51-69): (Seq ID NO:8)
  sp5'A2'(p5'A2')$_3$—[(Bu)p]$_2$—(5'gta ctt atc aaa ttc tta t3'-3't5')

At the 3'-terminus of the RSV genome, there is a block of about 50 nucleotides which is not incorporated into the protein encoding transcript of the 3'-proximal gene but which is transcribed to yield a small RNA species that has been called a "leader RNA." Evidence indicates that the exact 3'-end of the genome is the entry site for the RNA transcriptional machinery and that leader RNA synthesis, which involves termination at a purine-rich sequence at the leader-template-NP-gene boundary, is an obligatory prelude to progression of the transcriptase through the rest of the genome. In addition, since the 3'-end of the genome is where both replicative and transcriptional RNA synthesis initiate, this site provides a site at which the critical switch between the two kinds of RNA synthesis may operate. Finally, the 3'-terminus of the RSV genome is rich in uridylate residues which may be more readily susceptible to cleavage by the 2-5A-dependent RNase.

These functions of the 3'-terminus of the genomic strand can be disrupted more readily than other portions of the genomic strand. Thus the following activator-antisense complexes, which bind to the genomic strand can be used to practice the invention.

spA$_4$-antiRSVGe3'-3'T/(1-18): (Seq ID NO:9)
  sp5'A2'(p5'A2')$_3$—[(Bu)p]$_2$—(5'acg cga aaa aat gcg tac3'-3't5')

spA$_4$-antiRSVGe3'-3'T/(84-101) (Seq ID NO:10):
  sp5'A2'(p5'A2')$_3$—[(Bu)p]$_2$—(5'ctc cct tgg tta gag atg3'-3't5')

spA$_4$-antiRSVGe3'-3'T/(369-386) (Seq ID NO:11):
  sp5'A2'(p5'A2')$_3$—[(Bu)p]$_2$—(5'gaa atg atg gaa tta aca3'-3't5')

EXAMPLE 12
COMPARATIVE DATA OF spA$_4$-antiRSV3'3'T/(8281–8299)

A comparison of the efficacies of spA$_4$-antiRSV3'3'T/(8281–8299) treatement and conventional ribarvirin treatement can be obtained by determining the RSV-inhibitory concentration and the cytotoxic concentration of each compound. Cultures of the human laryngeal carcinoma cell line HEp-2 and the murine renal cell line MA-104 were established and infected with an MOI=0.005. Cultures were fed twice daily. Treatment with either ribavirin or spA$_4$-antiRSV3'3'T/(8281–8299) was begun simlutaneously with infection and continued for four days. Treatment was then withdrawn and the test read on day 5. The effects of treatment on RSV infection were reported as 1) an EC$_{50}$, the concentration at which there was a 50% reduction in the observable cytopathic effects of infection and 2) an EC$_{90}$, the concentration at which there was a 90% reduction in viral production. The cytotoxic concentration, the IC$_{50}$ was taken as the concentration that resulted in a 50% reduction in cell number. Therapuetic efficacy is estimated by the Selectivity Index, which is the ratio of IC$_{50}$/EC$_{50}$.

The results are shown in Tables 5 and 6. Table 5 shows that in HEp-2 cells spA$_4$-antiRSV3'3'T/(8281–8299) had an EC$_{50}$ of 0.3 $\mu$M; ribarvirin had an EC$_{50}$ of 4 $\mu$M. The IC$_{50}$s were >10 $\mu$M and 41 $\mu$M, respectively. Thus, spA$_4$-antiRSV3'3'T/(8281–8299) had an SI more than three fold higher than ribavirin.

Table 6 shows the analogous results concerning MA-104 cells. The SI of spA$_4$-antiRSV3'3'T/(8281–8299) and ribavirin were found to be >500 and about 200, respectively.

REFERENCES

Beigelman, L., Matulic-Adamic, J., et al., Synthesis and biological activities of a phosphorodithioate analog of 2-5A. Nucleic Acid Research 23:3989–94.
Balotta, C, Lusso, P., Crowley, R, Gallo, RC, Franchini, G. 1993. Antisense phosphorothioate oligodeoxynucleotides targeted to the vpr gene inhibit human immunodeficiency virus type 1 replication in primary human macrophages. J. Virology, 67: 4409–4414.
Chebath, J., Benech, P., Revel, M and Vigneron, M. 1987. Constitutive expression of (2'-5') oligo A synthetase confers resistance to picornavirus infection. Nature 330, 587–588.
Cirino, NM, Panuska, JR, Villani, A, Taraf, H, Rebert, NA, Merolla, R, Tsivitse, P, Gilbert, IA. 1993. Restricted replication of respiratory syncytial virus in human alveolar macrophages. J Gen Virol 74:1527–1537.
Floyd-Smith, G, Slattery, E. and Lengyel, P. 1981. Interferon action: RNA cleavage pattern of a (2'-5') oligoadenylate-dependent endonuclease. Science 212: 1020–1032.
Freier, SM, Kienzek, R, Jaegar, JA, Sugimoto, N, Caruthers, MH, Neilson, T, and Turner, DH. 1986. Improved free-energy parameters for predictions of RNA duplex stability. 1989. Proc Natl Acad Sci USA 83:9373–9377.
Froelich, E.A. 1994. SPI Pharmaceuticals, Inc. - Company Report, Pershing Division - Donaldson, Lufkin & Jenrette.
Goodchild, J, Agrawal, S, Civeira, MP, Sarin, PS, Sun, D, Zamecnik, PC. 1988. Inhibition of human immunodeficiency virus replication by antisense oligodeoxynucleotides. Proc. Natl. Acad. Sci. USA. 85: 5507–5511.
Gribaudo, G, Lernbo, D, Cavallo, G, Landolfo, S, and Lengyel, P. 1991. Interferon action: binding of viral RNA to the 40-kilodalton 2'-5'oligoadenylate synthetase in interferon-treated HeLa cells infected with encelphalomyocarditis virus. J Virol 65, 1748–1757.
Gruenert, DC, Basbaum, CB, Welsh, MJ, Li, M, Finkbeiner, WE, Nadel, JA. 1988. Characterization of human tracheal epithelial cells transformed by an origin defective simian virus 40. Proc Nat Acad Sci, USA. 85: 5951–5955.
Hassel, B, Zhou, A, Maran, A, Silverman, RH. 1993. A dominant negative mutant of 2-5A-dependent RNase suppresses antiproliferative and antiviral effects of interferon, The EMBO Journal 12, 3297–3304.
Heilman, C. 1994. RFA: "Mechanism of RSV vaccine immunopotentiation". N.I.A.I.D., N.I.H., Bethesda, MD.
Lesiak, K.; Khamnei, S.; Torrence, P. F. 1993. 2',5'-Oligoadenylate-antisense chimeras-synthesis and properties. Bioconjugate Chem, 4:467–472.
Letsinger, RL, Zhang, G, Sun, DK, Ikeuchi, T, Sarin, PS. 1989. Cholesteryl-conjugated oligonucleotides: Synthesis, properties, and activity as inhibitors of replication of human immunodeficiency virus in cell culture. Proc Natl Acad Sci 86: 6553–6556.
Maran, A, Maitra, RK, Kumar, A, Dong, B, Xiao, W, Li, G, Williams, BRG, Torrence, PF, Silverman, RH. 1994. Blockage of NF-kB signaling by selective ablation of an mRNA target by 2-5A-antisense chimeras. Science 265:789–792.
Maitra, RK, Li, G, Xiao, W, Dong, B, Torrence, PF, and Silyerman, RH. 1995. Catalytic cleavage of an RNA target by 2-5A-antisense and 2-5A dependent RNase. J. Biol.Chem., 270: 15071–15075.
McIntosh, K, and Chanock, RM. 1990. Respiratory syncytial virus. In Virology, 2nd edition. Edited by BN Fields, DM Knipe et al., Raven Press, Ltd, New York, pp. 1045–1072
Merolla, R, Rebert, NA, Tsivitse, P, Hoffmann, SP, Panuska, JR. 1995. Respiratory syncytial virus replication in human lung epithelial cells: inhibition by tumor necrosis factor-a and interferon-a8247. Am J Rsp and Crit Care Med.
Midulla, F, Villani, A, Panuska, JR, Dab, I, Kolls, JK, Merolla, R, Ronchetti, R. 1993. Concise Communication: Respiratory syncytial virus lung infection in infants: Immunoregulatory role of infected alveolar macrophages. J Inf Dis 168: 1515–1519.
Panuska, JR, Hertz MI, Taraf, H, Villani, A, Cirino, NM. 1992. Respiratory syncytial virus infection of alveolar macrophages in adult transplant patients. Am Rev Resp Dis 145: 934–939.
Panuska, JR, Merolla, R, Rebert, NA, Hoffmann, SP, Tsivitse, P, Cirino, NM, Silverman, RH, Rankin, JA. 1995. Respiratory syncytial virus induces interleukin 10 by human aveolar macrophages: suppression of early cytokine production and implications for incomplete immunity. submitted to J Clin Invest).
Rysiecki, G, Gewert, DR, Williams, BRG. 1989. Constitutive expression of a 2',5'-oligoadenylate synthetase cDNA results in increased antiviral activity and growth suppression. J Interferon Res 9, 649–657.
Salser, W. 1977. Globin mRNA sequences: analysis of base pairing and evolutionary implications. Cold Spring Harbor Symposium on Quantitative Biology 42:985–1002.

REFERENCES

Silverman, RH. 1994. Fascination with 2-5A-Dependent RNase: A unique enzyme that functions in interferon action. J Interferon Res, 14:101–104.

Swiderski, PM, Bertrand, EL, and Kaplan, BE (1994) Polystyrene reverse-phase ion-pair chomatography of chimeric ribozymes. Analytical Biochemistry, 216: 83–88.

Torrence, PF, Maitra, RK, Lesiak, K, Khamnei, S, Zhou, A, and Silverman, RH . 1993. Targeting RNA for degradation with a 2',5'-oligoadenylate-antisense chimera. Proc. Natl Acad Sci USA, 90: 1300–1304.

Wreschner, DH, James, TC, Silverman, RH, and Kerr, IM. 1981. Ribosomal RNA cleavage, nuclease activation and 2-5A(ppp(A2'p)nA) in interferon-treated cells. Nucleic Acids Res. 9, 1571–1581.

Wreschner, DH, McCauley, JW, Skehei, JJ, and Kerr, IM. 1981. Interferon action-sequence specificity of the ppp(A2'p)nA-dependent ribonuclease. Nature 289, 414–417.

Xiao, W, Li, G, Lesiak, K, Dong, B, Silverman RH, and Torrence, PF. 1994. Synthesis of a 5'-thiophosphate analogue of 2-5A, a phosphatase resistant activator of the 2-5A dependent ribonuclease. Bioorganic & Med. Chem. Letts: 4, 2609–2614, 1994.

Zamecnik, PC, Goodchild, J, Taguchi, Y, Sarin, PS. 1986, Inhibition of replication and expression of human T-cell lymphotropic virus type III in cultured cells by exogenous synthetic oligonucleotides complementary to viral RNA. Proc Natl Acad Sci USA. 83: 4143–4146.

Zisson, A. 1993. Shaman Pharmaceuticals, Inc. - Company Report. Hambrecht & Quest Institutional Research - Company Report.

Zuker, M. 1989. Computer prediction of RNA structure. Methods in Enzymology 180:262–288.

TABLE 1

Modified Procedure for the Synthesis of Core (2',5')-Oligoadenylate/antisense Chimeras

| synthesis region (sequence edit) | coupling time (seconds) | coupling reagents & concentration | trityl mode |
|---|---|---|---|
| oligomer antisense (DNA antisense) | 15 | 0.1M monomer in acetonitrile | Trityl ON |
| linker | 300 | 0.1M linker in acetonitrile | Trityl ON |
| (2',5')oligoadenylate | 606 | 0.1M (2',5')Ado$^{Bz}$ in acetonitrile | Triyl ON |
| Phosphorylation | 60 | 0.1M P$^{III}$ reagent in acetonitrile | Trityl OFF |

TABLE 2

Synthesis Procedure for 5'-Terminal Phosphorylation

| Step | Solvent/reagent | Time | Volume |
|---|---|---|---|
| 1. coupling | 0.2M phosphorylation reagent in tetrazole/acetonitrile | 3 min. | 0.15 mL |
| 2. washing | acetonitrile | | 3 mL |
| 3. drying | argon | 3 min. | |
| 4. oxidation | 0.1M I2 in lutidine:THF:water (20:80:1) | 0.75 min. | 1 mL |
| 5. washing | acetonitrile | | 3 mL |
| 6. drying | argon | 3 min. | |
| 7. detritylation | 3% TCA in CH$_2$Cl$_2$ | 1.5 min. | 1 mL |
| 8. washing | 2% Py in acetonitrile | | 1 mL |
| 9. washing | acetonitrile | | 3 mL |

TABLE 3

Antiviral activities of chimeric antisense against RSV L polymerase RNA translation start site.

| | | % Inhibition oF RSV replication | | |
|---|---|---|---|---|
| Oligo/(site in RSV RNA) | Structure of Compounds [oligonucleotide]/treatment): | 3.3 μM | 6.6 μM | 9.9 μM |
| A$_4$-antiRSV3'-3'C/(8490–8509) (SEQ ID NO:12) | A2'p(A2'p)$_3$-[(Bu)p]$_2$-(5'aat ggg atc cat ttt gtc c3'-3'c5') | | 20 (1) | 28.3 (3) |
| pA$_4$-antiRSV/(8490–8509) (SEQ ID NO:13) | pA2'p(A2'p)$_3$-[(Bu)p]$_2$-(5'aat ggg atc cat ttt gtc cc3') | 3 (2) | 38.8 (4) | 64.8 (5) |
| pA$_4$-3'antiRSV5'/(8490–8509) (SEQ ID NO:14) | pA2'p(A2'p)$_3$-[(Bu)p]$_2$-(3'ccc tgt ttt acc tag ggt aa5') | | | 69 (1) |
| pA$_4$-antiRSV3'-3'C/(8490–8509) (SEQ ID NO:15) | pA2'p(A2'p)$_3$-[(Bu)p]$_2$-(5'aat ggg atc cat ttt gtc c3'-3'c5') | 2 (1) | 64.3 (3) | 74 (2) |
| spA4-antiRSV/(8490–8509) (SEQ ID NO:16) | spA2'p(A2'p)$_3$-[(Bu)p]$_2$-(5'aat ggg atc cat ttt gtc cc3') | 16.5 (2) | 71 (1) | 94 (1) |

Antiviral activity as determined by virus plaque assay at 36 hrs post-infection. In parentheses, are the number of times the experiments were done to produce the data. Results shown are the average of the percent inhibition data from 2 to 7 experiments, except for single experiment data; Percent inhibition is defined as-[(infectious virusparticles produced in oligonucleotide treated cells)/(infectious virus particles produced in untreated cells)] × 100. M.O.I. was 2.0 p.f.u. per cell.

Chimeric 2-5A-antisense oligonucleotides are abbreviated according to the following convention employed herein for added clarity. The 2-5A domain of the chimera is indicated in bold-face capitalized type; i.e., pA2'p(A2'p)3. The linker moiety is abbreviated as [(Bu)p]$_2$ which stands for two 1,4-butanediol-molecules linked throughphosphodiester bonds to each other and the 2-5A and antisense domains of the chimera, i.e., -[(Bu)p]$_2$. The antisense oligonucleotide is represented in lower case bold-face type in triplet repeats with normal 3',5' phosphodiester linkages in the polarity shown; i.e., (3'ccc tgt ttt acc tag ggt aa5'). Exceptions include theinversion of polarity for the entire chain or for the terminal 3'-nucleotide, both of which are clearly indicated. When the 5'-monophosphate of the 2-5A domain of the chimera was modified to the 5'-thiophosphate, the abbrevation used is spA2'p(A2'p)$_3$.

TABLE 4

Antiviral activities of stabilized chimeric antisense against different sites in RSV M2 and L mRNAs.

| Oligo/(site in RSV RNA) | Structure of Compounds [oligonucleotide]/treatment): | % Inhibition oF RSV replication | | |
|---|---|---|---|---|
| | | 3.3 μM | 6.6 μM | 9.9 μM |
| spA$_4$-antiRSV3'-3'N Series: | | | | |
| spA$_4$-antiRSV3'-3'A/(8530–8547) (SEQ ID NO: 17) | spA2'p(A2'p)$_3$-[(Bu)p]$_2$-(5'cta tcg gtt aga taa ac3'-3'a5') | 2.5 (1) | | |
| spA$_4$-antiRSV3'-3'G/(8599–8618) (SEQ ID NO: 18) | spA2'p(A2'p)$_3$-[(Bu)p]$_2$-(5'gat aag gac cat tga ata t3'-3'g5') | 44 (1) | | |
| spA$_4$-antiRSV3'-3'C/(8561–8578) (SEQ ID NO: 19) | spA2'p(A2'p)$_3$-[(Bu)p]$_2$-(5'ctc tga gaa aga gat aa3'-3'c5') | 57 (1) | | |
| spA$_4$-antiRSV3'-3'T/(8261–8279) (SEQ ID NO: 20) | spA2'p(A2'p)$_3$-[(Bu)p]$_2$-(5'gat tga aat ata gtg tgt3'-3't5') | 78 (2) | 87 (1) | 87 (1) |
| spA$_4$-antiRSV3'-3'A/(8251–8270) (SEQ ID NO: 21) | spA2'p(A2'p)$_3$-[(Bu)p]$_2$-(5'ata gtg tgt tct ttt gat t3'-3'a5') | 86.7 (2) | 92 (1) | |
| spA$_4$-antiRSV3'-3'T/(8281–8299) (SEQ ID NO: 22) | spA2'p(A2'p)$_3$-[(Bu)p]$_2$-(5'atg gtt att tgg gtt gtt3'-3't5') | 91.3 (3) | 97 (1) | 99.6 (1) | see legend to Table 3.

TABLE 5

ANTIVIRAL ACTIVITY of spA4-antiRSV3'-3'T/(8281)

Hep-2 Cells
Neutral Red

| Compound | EC$_{50}$ | IC$_{50}$ | SI |
|---|---|---|---|
| spA4-anhRSV3'-3'T/(8281) | 0.3 μM | >10 μM | >33 |
| Ribavirin | 4 μM | 41 μM | 10 | determined with RSV strain A2, MOI = 0.005

Fresh medium and oligo or ribavirin added twice daliy for 4 d and test read on d 5.

EC$_{50}$ effective concentration to reduce RSV-induced CPE by 50%.

IC$_{50}$ 50% inhibitory concentration for cytotoxicity to cells (visual and dye uptake as determined in rapidly dividing cells as opposed to stationary cells used for viral assays.

SI selctivity index = IC$_{50}$/EC$_{50}$

TABLE 6

ANTIVIRAL ACTIVITY of spA4-antiRSV3'-3'T/(8281)

MA-104 Cells
Visual CPE and Virus Yield Reduction

| Compound | EC$_{50}$ | EC$_{90}$ | IC$_{50}$ | SI |
|---|---|---|---|---|
| spA4-antiRSV3'-3'T/(8281) | 0.02 μM | 0.02 μM | >10 μM | >500 |
| Ribavirin | 1 μM | 7 μM | 210 μM | 210 | as determined with RSV strain A2, MOI = 0.005

Fresh medium and oligo or ribavirin added twice daily for 4 d and test read on d 5.

EC$_{50}$ effective concentration to reduce RSV-induced CPE by 50%.

EC$_{90}$ effective concentration to reduce RSV yield by 90%.

IC$_{50}$ 50% inhibitory concentration for cytotoxicity to cells (visual and dye uptake as determined in rapidly dividing cells as opposed to station ary cells used for viral assays.)

SI selectivity index = IC$_{50}$/EC$_{50}$

We claim:

1. A chimeric molecule comprising:
   (a) an antisense oligonucleotide in which the oligonucleotide is complementary to a portion of the antigenomic RNA strand of a strain of a Respiratory Syncytial Virus (RSV) spanning residues 617 to 663 of SEQ ID NO: 23; residues 718 to 772 of SEQ ID NO: 23; residues 2490 to 2530 of SEQ ID NO: 23, residues 3212 to 3247 of SEQ ID NO: 23; residues 5240 to 5288 of SEQ ID NO: 23 or residues 8251 to 8299 of SEQ ID NO: 23 of the RSV strain A2 genome; and
   (b) an oligonucleotide activator of RNase L attached to the antisense oligonucleotide by a linker.

2. The chimeric molecule of claim 1 wherein said chimeric molecule further comprises a modification to the 3' terminus of the oligonucleotide which protects the oligonucleotide from exonucleases.

3. The chimeric molecule of claim 1 which further comprises additional adenylate molecules attached to the 3' terminus of the oligonucleotide.

4. The chimeric molecule of claim 1 in which the oligonucleotide activator is selected from the group consisting of sp5'A2'(p5'A2')$_2$—O—, sp5'A2'(p5'A2')$_3$—O—, p5'A2'(p5'A2')$_2$—O—, and p5'A2'(p5'A2')$_3$—O—.

5. The chimeric molecule of claim 1 in which the first end is the 5' terminus, and the 3' terminal hydroxyl of the antisense oligonucleotide is blocked by a blocker selected from the group consisting of a -p3'N5' nucleotide, a p-O-alkylamine, a p-O-hydroxyalkylamine, a sp-O-alkylamine, a sp-O-hydroxyalkylamine, ethyl and methyl.

6. The chimeric molecule of claim 1 in which the antisense oligonucleotide is selected from the group consisting of residues 8251–8270 (SEQ ID NO. 21), 8261–8279 (SEQ ID NO. 20) and 8281–8299 (SEQ ID NO. 22), numbered in the 5'→3' direction.

7. The chimeric molecule of claim 1 in which the antisense oligonucleotide contains one or more phospho- moieties selected from the group consisting of phosphorothioate, methylphosphonate and methylphosphonothioate.

* * * * *